US010981997B1

(12) United States Patent
Weidanz et al.

(10) Patent No.: US 10,981,997 B1
(45) Date of Patent: Apr. 20, 2021

(54) ANTIBODIES TARGETING A COMPLEX COMPRISING NON-CLASSICAL HLA-I AND NEOANTIGEN AND THEIR METHODS OF USE

(71) Applicant: AbeXXa Biologics, Inc., Arlington, TX (US)

(72) Inventors: Jon Weidanz, Arlington, TX (US); Katherine Upchurch-Ange, Arlington, TX (US)

(73) Assignee: ABEXXA BIOLOGICS, INC., Arlington, TX (US)

( * ) Notice: Subject to any disclaimer, the term of this patent is extended or adjusted under 35 U.S.C. 154(b) by 0 days.

(21) Appl. No.: 16/926,355

(22) Filed: Jul. 10, 2020

Related U.S. Application Data

(60) Provisional application No. 63/032,886, filed on Jun. 1, 2020.

(51) Int. Cl.
*C07K 16/28* (2006.01)
*A61P 35/00* (2006.01)

(52) U.S. Cl.
CPC .......... *C07K 16/2833* (2013.01); *A61P 35/00* (2018.01); *C07K 2317/32* (2013.01); *C07K 2317/50* (2013.01); *C07K 2317/565* (2013.01); *C07K 2317/62* (2013.01); *C07K 2317/64* (2013.01)

(58) Field of Classification Search
CPC ............... C07K 16/2833; C07K 16/00–468
See application file for complete search history.

(56) References Cited

U.S. PATENT DOCUMENTS

| 8,168,427 | B2 | 5/2012 | Sahin et al. |
| 9,206,257 | B2 | 12/2015 | Ho et al. |
| 9,770,038 | B2 * | 9/2017 | Liu ..................... C07K 16/1278 |
| 2014/0010825 | A1 | 1/2014 | Ravindranath et al. |
| 2019/0071502 | A1 * | 3/2019 | Weidanz ............. C07K 16/081 |
| 2020/0291128 | A1 * | 9/2020 | Weidanz ............ C07K 16/2866 |

FOREIGN PATENT DOCUMENTS

| WO | 2016062851 A1 | 4/2016 |
| WO | 2018005556 A1 | 1/2018 |
| WO | 2020023548 A1 | 1/2020 |

OTHER PUBLICATIONS

Gornalusse, G.G., et al. "HLA-E-expressing pluripotent stem cells escape allogeneic responses and lysis by NK cells", Nat Biotechnol. Aug. 2017, 35(8): 765-772.
PCT/US2019/043108 International Search Report dated Oct. 30, 2019.
PCT/US2019/043108 Written Opinion of the International Searching Authority dated Oct. 30, 2019.

* cited by examiner

*Primary Examiner* — Jessica H Roark
(74) *Attorney, Agent, or Firm* — Goodwin Procter LLP

(57) ABSTRACT

Provided herein are antibodies that selectively bind to complex comprising a non-classical HLA-I (e.g. HLA-E) and a neoantigen having variable heavy chain domains (VH), variable light chain domains (VL), and complementarity determining regions (CDRs) as disclosed herein, as well as methods and uses thereof.

13 Claims, 32 Drawing Sheets

Specification includes a Sequence Listing.

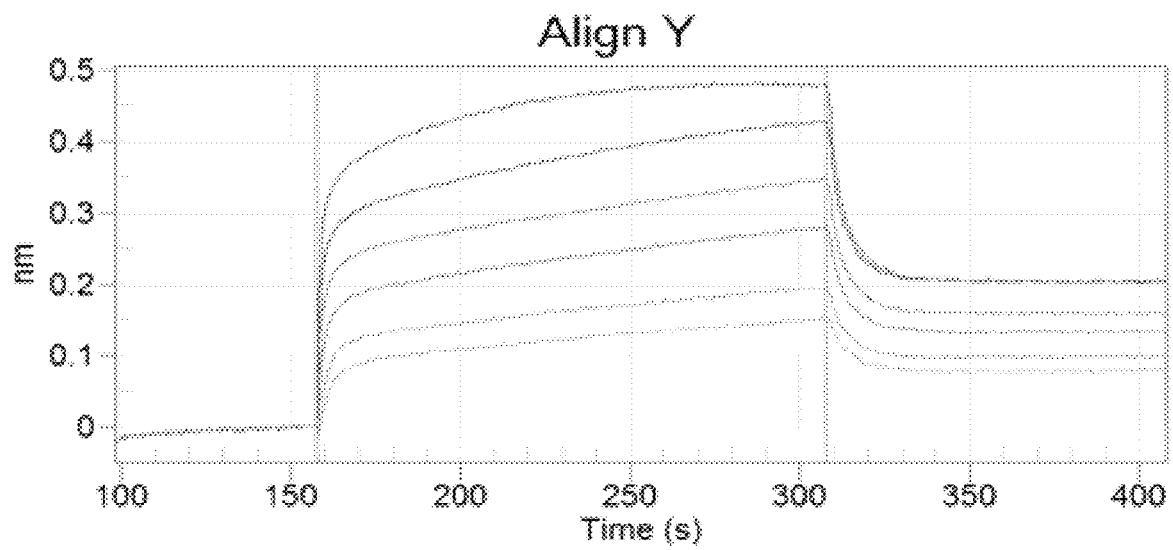
FIG. 1C
| Clone | $K_D$ | Error | $K_{on}$ | $K_{off}$ |
|---|---|---|---|---|
| Clone 1 | 4.11E-07 | 3.05E-08 | 1.48E+05 | 6.6E-02 |
FIG. 1D
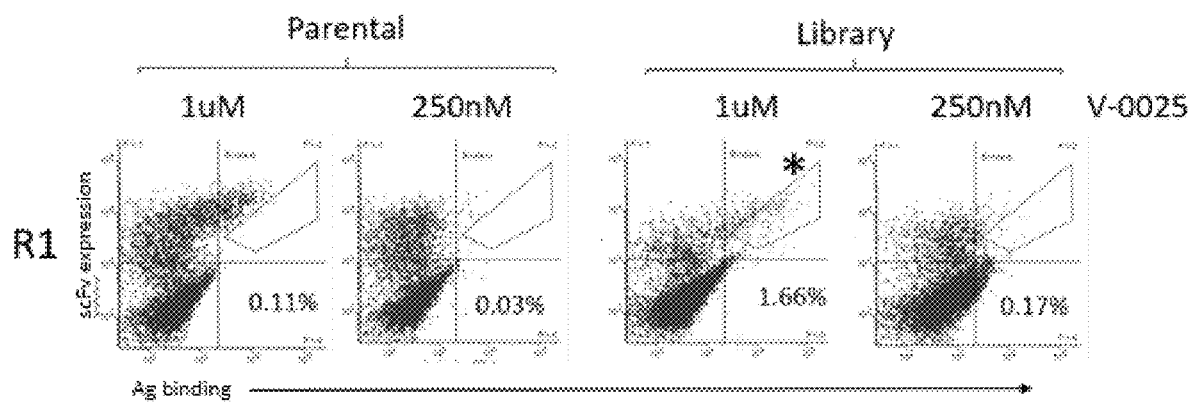
FIG. 2A

SEQUENCE LISTING

```
<160> NUMBER OF SEQ ID NOS: 33

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Ile Ser Ser Tyr
1               5

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Ser
1
```

```
<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Ala Ala Ala Tyr Pro Ser Leu
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Ser Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Ala Tyr Gly Gly Gly Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Lys Gly Leu Ser Asn Phe Asp Tyr
1               5

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

-continued

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Ala Tyr Pro Ser
                 85                  90                  95

Leu Phe Gly Gln Gly Thr Lys Val Glu Ile Lys
            100                 105

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ala Tyr Gly Gly Ala Thr Ala Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Leu Ser Asn Phe Asp Tyr Trp Gly Gln Gly Thr Leu Val
            100                 105                 110

Thr Val Ser Ser
        115

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Gly Ala Val Thr Thr Ser Asn Tyr
 1               5

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Thr Asn
 1

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 11

Ala Leu Trp Tyr Ser Asn Leu Trp Val
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Thr Phe Asn Thr Tyr Ala
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Arg Ser Lys Tyr Asn Asn Tyr Ala Thr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Arg His Gly Asn Phe Gly Asn Ser Tyr Val Ser Trp Phe Ala Tyr
1               5                   10                  15

<210> SEQ ID NO 15
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
```

<210> SEQ ID NO 16
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 17

<400> SEQUENCE: 17

000

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Met Ala Pro Arg Thr Leu Phe Leu
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Tyr Lys Asp Asp Asp Asp Lys
1               5

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 20

Gly Lys Pro Gly Ser Gly Lys Pro Gly Ser Gly Lys Pro Gly Ser Gly
1               5                   10                  15

Lys Pro Gly Ser
            20

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Met Ala Pro Arg Thr Leu Ile Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Met Ala Pro Arg Thr Leu Val Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Thr Ala Pro Arg Thr Leu Leu Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Met Ala Pro Arg Thr Leu Val Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Met Ala Pro Gln Ala Leu Leu Leu
1               5
```

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Met Ala Pro Arg Ala Leu Leu Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Met Ala Pro Arg Thr Leu Leu Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Met Ala Pro Arg Thr Leu Thr Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Met Ala Pro Arg Thr Val Leu Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Met Pro Pro Arg Thr Leu Leu Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 31

Val Thr Ala Pro Arg Thr Val Leu Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Met Arg Pro Val Ser Arg Val Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ala Arg Leu Pro Pro Leu Leu
1               5
```

US 10,981,997 B1

ANTIBODIES TARGETING A COMPLEX COMPRISING NON-CLASSICAL HLA-I AND NEOANTIGEN AND THEIR METHODS OF USE

CROSS-REFERENCE

This application claims the benefit of U.S. Provisional Application No. 63/032,886, filed on Jun. 1, 2020, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 31, 2020, is named ABX006_SL.txt and is 11,197 bytes in size.

SUMMARY

Disclosed herein, in certain embodiments, are monoclonal antibodies or an antigen-binding fragments thereof, comprising a light chain variable domain (VL) comprising an amino acid sequence at least 80% identical to an amino acid sequence set forth as SEQ ID NO: 7. Disclosed herein, in certain embodiments, are monoclonal antibodies or antigen-binding fragments thereof, comprising a light chain variable domain (VL) comprising an amino acid sequence at least 90% identical to an amino acid sequence set forth as SEQ ID NO: 7. Disclosed herein, in certain embodiments, are monoclonal antibodies or antigen-binding fragments thereof, comprising a light chain variable domain (VL) comprising an amino acid sequence at least 95% identical to an amino acid sequence set forth as SEQ ID NO: 7. Disclosed herein, in certain embodiments, are monoclonal antibodies or antigen-binding fragments thereof, comprising a light chain variable domain (VL) comprising an amino acid sequence at least 99% identical to an amino acid sequence set forth as SEQ ID NO: 7. Disclosed herein, in certain embodiments, are monoclonal antibodies or antigen-binding fragments thereof, comprising a light chain variable domain (VL) comprising an amino acid sequence 100% identical to an amino acid sequence set forth as SEQ ID NO: 7. In some embodiments, the monoclonal antibodies or antigen-binding fragments thereof comprise a heavy chain variable domain (VH) comprising an amino acid sequence at least 80% identical to an amino acid sequence set forth as SEQ ID NO: 8. In some embodiments, the monoclonal antibodies or antigen-binding fragments thereof comprise a heavy chain variable domain (VH) comprising an amino acid sequence at least 90% identical to an amino acid sequence set forth as SEQ ID NO: 8. In some embodiments, the monoclonal antibodies or antigen-binding fragments thereof comprise a heavy chain variable domain (VH) comprising an amino acid sequence at least 95% identical to an amino acid sequence set forth as SEQ ID NO: 8. In some embodiments, the monoclonal antibodies or antigen-binding fragments thereof comprise a heavy chain variable domain (VH) comprising an amino acid sequence at least 99% identical to an amino acid sequence set forth as SEQ ID NO: 8. In some embodiments, the monoclonal antibodies or antigen-binding fragments thereof comprise a heavy chain variable domain (VH) comprising an amino acid sequence 100% identical to an amino acid sequence set forth as SEQ ID NO: 8. In some embodiments, the monoclonal antibodies or antigen-binding fragments thereof selectively bind to a complex comprising an HLA-E and a neoantigen. In some embodiments, the monoclonal antibodies or antigen-binding fragments thereof do not have a binding affinity to the HLA-E alone. In some embodiments, the monoclonal antibodies or antigen-binding fragments thereof do not have a binding affinity to the neoantigen alone. In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL). In some embodiments, the HLA-E is HLA-E*0101 or HLA-E*0103. In some embodiments, the antibodies selectively bind to the complex comprising: (a) the HLA-E*0101 and the neoantigen; (b) the HLA-E*0103 and the neoantigen; or (c) the HLA-E*0101 and the neoantigen, and the HLA-E*0103 and the neoantigen. In some embodiments, the monoclonal antibodies or antigen-binding fragments thereof are murine antibodies, chimeric antibodies, camelid antibodies, humanized antibodies, or human antibodies. In some embodiments, the monoclonal antibodies or antigen-binding fragments thereof are TCR-like antibodies. In some embodiments, the monoclonal antibodies or antigen-binding fragments thereof are multispecific antibodies. In some embodiments, the monoclonal antibodies or antigen-binding fragments thereof are bispecific antibodies. In some embodiments, the monoclonal antibodies or antigen-binding fragments thereof are bispecific T cell engagers (BiTE). In some embodiments, the BiTE binds to a CD3 protein associated with a T cell receptor (TCR). In some embodiments, the BiTE further comprises a light chain variable domain (VL) comprising an amino acid sequence at least 80% identical to an amino acid sequence set forth as SEQ ID NO: 15. In some embodiments, the BiTE further comprises a heavy chain variable domain (VH) comprising an amino acid sequence at least 80% identical to an amino acid sequence set forth as SEQ ID NO: 16. In some embodiments, the monoclonal antibodies or antigen-binding fragments thereof are multifunctional antibodies. In some embodiments, the monoclonal antibodies or antigen-binding fragments thereof antibody further comprise a conjugated therapeutic moiety. In some embodiments, the selective binding of the antibodies to the complex comprising the HLA-E and the neoantigen induces an immune response in a cell. In some embodiments, the immune response comprises activation of (i) NK cells, (ii) T cells, or (iii) NK cells and T cells. In some embodiments, the T cell is a CD4+ T cell or a CD8+ T cell. In some embodiments, the immune response comprises activation of cytotoxic T cells (CTLs). In some embodiments, the cell is a cancer cell.

Disclosed herein, in certain embodiments, are monoclonal antibodies or antigen-binding fragments thereof, comprising a heavy chain variable domain (VH) comprising an amino acid sequence at least 80% identical to an amino acid sequence set forth as SEQ ID NO: 8. Disclosed herein, in certain embodiments, are monoclonal antibodies or antigen-binding fragments thereof, comprising a heavy chain variable domain (VH) comprising an amino acid sequence at least 90% identical to an amino acid sequence set forth as SEQ ID NO: 8. Disclosed herein, in certain embodiments, are monoclonal antibodies or antigen-binding fragments thereof, comprising a heavy chain variable domain (VH) comprising an amino acid sequence at least 95% identical to an amino acid sequence set forth as SEQ ID NO: 8. Disclosed herein, in certain embodiments, are monoclonal antibodies or antigen-binding fragments thereof, comprising a heavy chain variable domain (VH) comprising an amino acid sequence at least 99% identical to an amino acid sequence set forth as SEQ ID NO: 8. Disclosed herein, in certain embodiments, are monoclonal antibodies or antigen-binding fragments thereof, comprising a heavy chain variable domain (VH) comprising an amino acid sequence 100% identical to an amino acid sequence set forth as SEQ ID NO: 8. In some embodiments, the monoclonal antibodies or antigen-binding fragments thereof comprise a light chain variable domain (VL) comprising an amino acid sequence at least 80% identical to an amino acid sequence set forth as SEQ ID NO: 7. In some embodiments, the monoclonal antibodies or antigen-binding fragments thereof comprise a light chain variable domain (VL) comprising an amino acid sequence at least 90% identical to an amino acid sequence set forth as SEQ ID NO: 7. In some embodiments, the monoclonal antibodies or antigen-binding fragments thereof comprise a light chain variable domain (VL) comprising an amino acid sequence at least 95% identical to an amino acid sequence set forth as SEQ ID NO: 7. In some embodiments, the monoclonal antibodies or antigen-binding fragments thereof comprise a light chain variable domain (VL) comprising an amino acid sequence at least 99% identical to an amino acid sequence set forth as SEQ ID NO: 7. In some embodiments, the monoclonal antibodies or antigen-binding fragments thereof comprise a light chain variable domain (VL) comprising an amino acid sequence 100% identical to an amino acid sequence set forth as SEQ ID NO: 7. In some embodiments, the monoclonal antibodies or antigen-binding fragments thereof selectively binds to a complex comprising an HLA-E and a neoantigen. In some embodiments, the monoclonal antibodies or antigen-binding fragments thereof do not have a binding affinity to the HLA-E alone. In some embodiments, the monoclonal antibodies or antigen-binding fragments thereof do not have a binding affinity to the neoantigen alone. In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL). In some embodiments, the HLA-E is HLA-E*0101 or HLA-E*0103. In some embodiments, the antibodies selectively binds to the complex comprising: (a) the HLA-E*0101 and the neoantigen; (b) the HLA-E*0103 and the neoantigen; or (c) the HLA-E*0101 and the neoantigen, and the HLA-E*0103 and the neoantigen. In some embodiments, the monoclonal antibodies or antigen-binding fragments thereof are murine antibodies, chimeric antibodies, camelid antibodies, humanized antibodies, or human antibodies. In some embodiments, the monoclonal antibodies or antigen-binding fragments thereof are TCR-like antibodies. In some embodiments, the monoclonal antibodies or antigen-binding fragments thereof are multispecific antibodies. In some embodiments, the monoclonal antibodies or antigen-binding fragments thereof are bispecific antibodies. In some embodiments, the monoclonal antibodies or antigen-binding fragments thereof are bispecific T cell engagers (BiTE). In some embodiments, the BiTE binds to a CD3 protein associated with a T cell receptor (TCR). In some embodiments, the BiTE further comprises a light chain variable domain (VL) comprising an amino acid sequence at least 80% identical to an amino acid sequence set forth as SEQ ID NO: 15. In some embodiments, the BiTE further comprises a heavy chain variable domain (VH) comprising an amino acid sequence at least 80% identical to an amino acid sequence set forth as SEQ ID NO: 16. In some embodiments, the monoclonal antibodies or antigen-binding fragments thereof are multifunctional antibodies. In some embodiments, the monoclonal antibodies or antigen-binding fragments thereof antibody further comprise a conjugated therapeutic moiety. In some embodiments, the selective binding of the antibody to the complex comprising the HLA-E and the neoantigen induces an immune response in a cell. In some embodiments, the immune response comprises activation of (i) NK cells, (ii) T cells, or (iii) NK cells and T cells. In some embodiments, the T cell is a CD4+ T cell or a CD8+ T cell. In some embodiments, the immune response comprises activation of cytotoxic T cells (CTLs). In some embodiments, the cell is a cancer cell.

Disclosed herein, in certain embodiments, are monoclonal antibodies or antigen-binding fragments thereof, comprising a light chain complementarity determining region (CDR) having an amino acid sequence at least 80% identical to at least one of the amino acid sequences set forth as SEQ ID NOS: 1-3. Disclosed herein, in certain embodiments, are monoclonal antibodies or antigen-binding fragments thereof, comprising a light chain complementarity determining region (CDR) having an amino acid sequence at least 90% identical to at least one of the amino acid sequences set forth as SEQ ID NOS: 1-3. Disclosed herein, in certain embodiments, are monoclonal antibodies or antigen-binding fragments thereof, comprising a light chain complementarity determining region (CDR) having an amino acid sequence at least 95% identical to at least one of the amino acid sequences set forth as SEQ ID NOS: 1-3. Disclosed herein, in certain embodiments, are monoclonal antibodies or antigen-binding fragments thereof, comprising a light chain complementarity determining region (CDR) having an amino acid sequence at least 99% identical to at least one of the amino acid sequences set forth as SEQ ID NOS: 1-3. Disclosed herein, in certain embodiments, are monoclonal antibodies or antigen-binding fragments thereof, comprising a light chain complementarity determining region (CDR) having an amino acid sequence 100% identical to at least one of the amino acid sequences set forth as SEQ ID NOS: 1-3. In some embodiments, the monoclonal antibodies or antigen-binding fragments thereof comprise a heavy chain complementarity determining region (CDR) having an amino acid sequence at least 80% identical to at least one of the amino acid sequences set forth as SEQ ID NOS: 4-6. In some embodiments, the monoclonal antibodies or antigen-binding fragments thereof comprise a heavy chain complementarity determining region (CDR) having an amino acid sequence at least 90% identical to at least one of the amino acid sequences set forth as SEQ ID NOS: 4-6. In some embodiments, the monoclonal antibodies or antigen-binding fragments thereof comprise a heavy chain complementarity determining region (CDR) having an amino acid sequence at least 95% identical to at least one of the amino acid sequences set forth as SEQ ID NOS: 4-6. In some embodiments, the monoclonal antibodies or antigen-binding fragments thereof comprise a heavy chain complementarity determining region (CDR) having an amino acid sequence at least 99% identical to at least one of the amino acid sequences set forth as SEQ ID NOS: 4-6. In some embodiments, the monoclonal antibodies or antigen-binding fragments thereof comprise a heavy chain complementarity determining region (CDR) having an amino acid sequence 100% identical to at least one of the amino acid sequences set forth as SEQ ID NOS: 4-6. In some embodiments, the monoclonal antibodies or antigen-binding fragments thereof comprise a light chain variable domain (VL) comprising an amino acid sequence at least 80% identical to an amino acid sequence set forth as SEQ ID NO: 7. In some embodiments, the monoclonal antibodies or antigen-binding fragments thereof comprise a heavy chain variable domain (VH) comprising an amino acid sequence at least 80% identical to an amino acid sequence set forth as SEQ ID NO: 8. In some embodiments, the monoclonal antibodies or antigen-binding fragments thereof selectively binds to a complex comprising an HLA-E and a neoantigen. In some embodiments, the monoclonal antibodies or antigen-binding fragments thereof do not have a binding affinity to the HLA-E alone. In some embodiments, the monoclonal antibodies or antigen-binding fragments thereof do not have a binding affinity to the neoantigen alone. In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL). In some embodiments, the HLA-E is HLA-E*0101 or HLA-E*0103. In some embodiments, the antibodies selectively binds to the complex comprising: the HLA-E*0101 and the neoantigen; the HLA-E*0103 and the neoantigen; or the HLA-E*0101 and the neoantigen, and the HLA-E*0103 and the neoantigen. In some embodiments, the monoclonal antibodies or antigen-binding fragments thereof are murine antibodies, chimeric antibodies, camelid antibodies, humanized antibodies, or human antibodies. In some embodiments, the monoclonal antibodies or antigen-binding fragments thereof are TCR-like antibodies. In some embodiments, the monoclonal antibodies or antigen-binding fragments thereof are multispecific antibodies. In some embodiments, the monoclonal antibodies or antigen-binding fragments thereof are bispecific antibodies. In some embodiments, the monoclonal antibodies or antigen-binding fragments thereof are bispecific T cell engagers (BiTE). In some embodiments, the BiTE binds to a CD3 protein associated with a T cell receptor (TCR). In some embodiments, the BiTE further comprises a light chain complementarity determining region (CDR) having an amino acid sequence at least 80% identical to at least one of the amino acid sequences set forth as SEQ ID NOS: 9-11. In some embodiments, the BiTE further comprises a heavy chain complementarity determining region (CDR) having an amino acid sequence at least 80% identical to at least one of the amino acid sequences set forth as SEQ ID NOS: 12-14. In some embodiments, the BiTE further comprises a light chain variable domain (VL) comprising an amino acid sequence at least 80% identical to an amino acid sequence set forth as SEQ ID NO: 15. In some embodiments, the BiTE further comprises a heavy chain variable domain (VH) comprising an amino acid sequence at least 80% identical to an amino acid sequence set forth as SEQ ID NO: 16. In some embodiments, the monoclonal antibodies or antigen-binding fragments thereof are multifunctional antibodies. In some embodiments, the monoclonal antibodies or antigen-binding fragments thereof antibody further comprise a conjugated therapeutic moiety. In some embodiments, the selective binding of the antibody to the complex comprising the HLA-E and the neoantigen induces an immune response in a cell. In some embodiments, the immune response comprises activation of (i) NK cells, (ii) T cells, or (iii) NK cells and T cells. In some embodiments, the T cell is a CD4+ T cell or a CD8+ T cell. In some embodiments, the immune response comprises activation of cytotoxic T cells (CTLs). In some embodiments, the cell is a cancer cell.

Disclosed herein, in certain embodiments, are monoclonal antibodies or antigen-binding fragments thereof, comprising a heavy chain complementarity determining region (CDR) having an amino acid sequence at least 80% identical to at least one of the amino acid sequences set forth as SEQ ID NOS: 4-6. Disclosed herein, in certain embodiments, are monoclonal antibodies or antigen-binding fragments thereof, comprising a heavy chain complementarity determining region (CDR) having an amino acid sequence at least 90% identical to at least one of the amino acid sequences set forth as SEQ ID NOS: 4-6. Disclosed herein, in certain embodiments, are monoclonal antibodies or antigen-binding fragments thereof, comprising a heavy chain complementarity determining region (CDR) having an amino acid sequence at least 95% identical to at least one of the amino acid sequences set forth as SEQ ID NOS: 4-6. Disclosed herein, in certain embodiments, are monoclonal antibodies or antigen-binding fragments thereof, comprising a heavy chain complementarity determining region (CDR) having an amino acid sequence at least 99% identical to at least one of the amino acid sequences set forth as SEQ ID NOS: 4-6. Disclosed herein, in certain embodiments, are monoclonal antibodies or antigen-binding fragments thereof, comprising a heavy chain complementarity determining region (CDR) having an amino acid sequence 100% identical to at least one of the amino acid sequences set forth as SEQ ID NOS: 4-6. In some embodiments, the monoclonal antibody or antigen-binding fragment comprises a light chain complementarity determining region (CDR) having an amino acid sequence at least 80% identical to at least one of the amino acid sequences set forth as SEQ ID NOS: 1-3. In some embodiments, the monoclonal antibody or antigen-binding fragment comprises a light chain complementarity determining region (CDR) having an amino acid sequence at least 90% identical to at least one of the amino acid sequences set forth as SEQ ID NOS: 1-3. In some embodiments, the monoclonal antibody or antigen-binding fragment comprises a light chain complementarity determining region (CDR) having an amino acid sequence at least 95% identical to at least one of the amino acid sequences set forth as SEQ ID NOS: 1-3. In some embodiments, the monoclonal antibody or antigen-binding fragment comprises a light chain complementarity determining region (CDR) having an amino acid sequence at least 99% identical to at least one of the amino acid sequences set forth as SEQ ID NOS: 1-3. In some embodiments, the monoclonal antibody or antigen-binding fragment comprises a light chain complementarity determining region (CDR) having an amino acid sequence 100% identical to at least one of the amino acid sequences set forth as SEQ ID NOS: 1-3. In some embodiments, the monoclonal antibodies or antigen-binding fragments thereof comprise a heavy chain variable domain (VH) comprising an amino acid sequence at least 80% identical to an amino acid sequence set forth as SEQ ID NO: 8. In some embodiments, the monoclonal antibodies or antigen-binding fragments thereof comprise a light chain variable domain (VL) comprising an amino acid sequence at least 80% identical to an amino acid sequence set forth as SEQ ID NO: 7. In some embodiments, the monoclonal antibodies or antigen-binding fragments thereof selectively binds to a complex comprising an HLA-E and a neoantigen. In some embodiments, the monoclonal antibodies or antigen-binding fragments thereof do not have a binding affinity to the HLA-E alone. In some embodiments, the monoclonal antibodies or antigen-binding fragments thereof do not have a binding affinity to the neoantigen alone. In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL). In some embodiments, the HLA-E is HLA-E*0101 or HLA-E*0103. In some embodiments, the antibodies selectively bind to the complex comprising: (a) the HLA-E*0101 and the neoantigen; (b) the HLA-E*0103 and the neoantigen; or (c) the HLA-E*0101 and the neoantigen, and the HLA-E*0103 and the neoantigen. In some embodiments, the monoclonal antibodies or antigen-binding fragments thereof are murine antibodies, chimeric antibodies, camelid antibodies, humanized antibodies, or human antibodies. In some embodiments, the monoclonal antibodies or antigen-binding fragments thereof are TCR-like antibodies. In some embodiments, the monoclonal antibodies or antigen-binding fragments thereof are multispecific antibodies. In some embodiments, the monoclonal antibodies or antigen-binding fragments thereof are bispecific antibodies. In some embodiments, the monoclonal antibodies or antigen-binding fragments thereof are bispecific T cell engagers (BiTE). In some embodiments, the BiTE binds to a CD3 protein associated with a T cell receptor (TCR). In some embodiments, the BiTE further comprises a light chain complementarity determining region (CDR) having an amino acid sequence at least 80% identical to at least one of the amino acid sequences set forth as SEQ ID NOS: 9-11. In some embodiments, the BiTE further comprises a heavy chain complementarity determining region (CDR) having an amino acid sequence at least 80% identical to at least one of the amino acid sequences set forth as SEQ ID NOS: 12-14. In some embodiments, the BiTE further comprises a light chain variable domain (VL) comprising an amino acid sequence at least 80% identical to an amino acid sequence set forth as SEQ ID NO: 15. In some embodiments, the BiTE further comprises a heavy chain variable domain (VH) comprising an amino acid sequence at least 80% identical to an amino acid sequence set forth as SEQ ID NO: 16. In some embodiments, the monoclonal antibodies or antigen-binding fragments thereof are multifunctional antibodies. In some embodiments, the monoclonal antibodies or antigen-binding fragments thereof antibody further comprise a conjugated therapeutic moiety. In some embodiments, the selective binding of the antibody to the complex comprising the HLA-E and the neoantigen induces an immune response in a cell. In some embodiments, the immune response comprises activation of (i) NK cells, (ii) T cells, or (iii) NK cells and T cells. In some embodiments, the cell is a CD4+ T cell or a CD8+ T cell. In some embodiments, the immune response comprises activation of cytotoxic T cells (CTLs). In some embodiments, the cell is a cancer cell.

Disclosed herein, in certain embodiments, are bispecific antibodies or an antigen-binding fragment thereof, comprising: a light chain complementarity determining region (CDR) having an amino acid sequence at least 80% identical to at least one of the amino acid sequences set forth as SEQ ID NOS: 1-3; or a heavy chain complementarity determining region (CDR) having an amino acid sequence at least 80% identical to at least one of the amino acid sequences set forth as SEQ ID NOS: 4-6; and a light chain complementarity determining region (CDR) having an amino acid sequence at least 80% identical to at least one of the amino acid sequences set forth as SEQ ID NOS: 9-11; or a heavy chain complementarity determining region (CDR) having an amino acid sequence at least 80% identical to at least one of the amino acid sequences set forth as SEQ ID NOS: 12-14. In some embodiments, the bispecific antibodies comprise: (a) a light chain variable domain (VL) comprising an amino acid sequence at least 80% identical to an amino acid sequence set forth as SEQ ID NO: 7; or a heavy chain variable domain (VH) comprising an amino acid sequence at least 80% identical to an amino acid sequence set forth as SEQ ID NO: 8; and (b) a light chain variable domain (VL) comprising an amino acid sequence at least 80% identical to an amino acid sequence set forth as SEQ ID NO: 15; or a heavy chain variable domain (VH) comprising an amino acid sequence at least 80% identical to an amino acid sequence set forth as SEQ ID NO: 16. Disclosed herein, in certain embodiments, are bispecific antibodies or an antigen-binding fragment thereof, comprising: a light chain complementarity determining region (CDR) having an amino acid sequence at least 80% identical to at least one of the amino acid sequences set forth as SEQ ID NOS: 1-3; and a heavy chain complementarity determining region (CDR) having an amino acid sequence at least 80% identical to at least one of the amino acid sequences set forth as SEQ ID NOS: 4-6; and a light chain complementarity determining region (CDR) having an amino acid sequence at least 80% identical to at least one of the amino acid sequences set forth as SEQ ID NOS: 9-11; and a heavy chain complementarity determining region (CDR) having an amino acid sequence at least 80% identical to at least one of the amino acid sequences set forth as SEQ ID NOS: 12-14. In some embodiments, the bispecific antibodies comprise: (a) a light chain variable domain (VL) comprising an amino acid sequence at least 80% identical to an amino acid sequence set forth as SEQ ID NO: 7; and a heavy chain variable domain (VH) comprising an amino acid sequence at least 80% identical to an amino acid sequence set forth as SEQ ID NO: 8; and (b) a light chain variable domain (VL) comprising an amino acid sequence at least 80% identical to an amino acid sequence set forth as SEQ ID NO: 15; and a heavy chain variable domain (VH) comprising an amino acid sequence at least 80% identical to an amino acid sequence set forth as SEQ ID NO: 16. In some embodiments, the bispecific antibodies selectively bind to a complex comprising an HLA-E and a neoantigen. In some embodiments, the bispecific antibodies do not have a binding affinity to the HLA-E alone. In some embodiments, the bispecific antibodies do not have a binding affinity to the neoantigen alone. In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL). In some embodiments, the HLA-E is HLA-E*0101 or HLA-E*0103. In some embodiments, the antibodies selectively binds to the complex comprising: the HLA-E*0101 and the neoantigen; the HLA-E*0103 and the neoantigen; or the HLA-E*0101 and the neoantigen, and the HLA-E*0103 and the neoantigen. In some embodiments, the monoclonal antibodies or antigen-binding fragments thereof are murine antibodies, chimeric antibodies, camelid antibodies, humanized antibodies, or human antibodies. In some embodiments, the monoclonal antibodies or antigen-binding fragments thereof are bispecific T cell engagers (BiTE). In some embodiments, the BiTE binds to a CD3 protein associated with a T cell receptor (TCR). In some embodiments, the monoclonal antibodies or antigen-binding fragments thereof are multifunctional antibodies. In some embodiments, the monoclonal antibodies or antigen-binding fragments thereof antibody further comprise a conjugated therapeutic moiety. In some embodiments, the selective binding of the antibody to the complex comprising the HLA-E and the neoantigen induces an immune response in a cell. In some embodiments, the immune response comprises activation of (i) NK cells, (ii) T cells, or (iii) NK cells and T cells. In some embodiments, the T cell is a CD4+ T cell or a CD8+ T cell. In some embodiments, the immune response comprises activation of cytotoxic T cells (CTLs). In some embodiments, the cell is a cancer cell.

Disclosed herein, in certain embodiments, are pharmaceutical compositions comprising: (a) a monoclonal antibody or an antigen-binding fragment thereof disclosed herein or a bispecific antibody or an antigen-binding fragment thereof disclosed herein; and (b) a pharmaceutically acceptable carrier or excipient.

Disclosed herein, in certain embodiments, are methods of treating cancer in an individual in need thereof, comprising administering to the individual an effective amount of a monoclonal antibody or an antigen-binding fragment thereof comprising a light chain complementarity determining region (CDR) having an amino acid sequence at least 80% identical to at least one of the amino acid sequences set forth as SEQ ID NOS: 1-3. Disclosed herein, in certain embodiments, are methods of treating cancer in an individual in need thereof, comprising administering to the individual an effective amount of a monoclonal antibody or an antigen-binding fragment thereof comprising a heavy chain complementarity determining region (CDR) having an amino acid sequence at least 80% identical to at least one of the amino acid sequences set forth as SEQ ID NOS: 4-6. In some embodiments, the monoclonal antibodies or antigen-binding fragments thereof comprise (a) a light chain complementarity determining region (CDR) having an amino acid sequence at least 80% identical to at least one of the amino acid sequences set forth as SEQ ID NOS: 1-3; and (b) a heavy chain complementarity determining region (CDR) having an amino acid sequence at least 80% identical to at least one of the amino acid sequences set forth as SEQ ID NOS: 4-6. In some embodiments, the monoclonal antibodies or antigen-binding fragments thereof comprise (a) a light chain complementarity determining region (CDR) having an amino acid sequence at least 90% identical to at least one of the amino acid sequences set forth as SEQ ID NOS: 1-3; and (b) a heavy chain complementarity determining region (CDR) having an amino acid sequence at least 90% identical to at least one of the amino acid sequences set forth as SEQ ID NOS: 4-6. In some embodiments, the monoclonal antibodies or antigen-binding fragments thereof comprise (a) a light chain complementarity determining region (CDR) having an amino acid sequence at least 95% identical to at least one of the amino acid sequences set forth as SEQ ID NOS: 1-3; and (b) a heavy chain complementarity determining region (CDR) having an amino acid sequence at least 95% identical to at least one of the amino acid sequences set forth as SEQ ID NOS: 4-6. In some embodiments, the monoclonal antibodies or antigen-binding fragments thereof comprise (a) a light chain complementarity determining region (CDR) having an amino acid sequence at least 99% identical to at least one of the amino acid sequences set forth as SEQ ID NOS: 1-3; and (b) a heavy chain complementarity determining region (CDR) having an amino acid sequence at least 99% identical to at least one of the amino acid sequences set forth as SEQ ID NOS: 4-6. In some embodiments, the monoclonal antibodies or antigen-binding fragments thereof comprise (a) a light chain complementarity determining region (CDR) having an amino acid sequence 100% identical to at least one of the amino acid sequences set forth as SEQ ID NOS: 1-3; and (b) a heavy chain complementarity determining region (CDR) having an amino acid sequence 100% identical to at least one of the amino acid sequences set forth as SEQ ID NOS: 4-6. In some embodiments, the monoclonal antibodies or antigen-binding fragments thereof comprise a light chain variable domain (VL) comprising an amino acid sequence at least 80% identical to an amino acid sequence set forth as SEQ ID NO: 7. In some embodiments, the monoclonal antibodies or antigen-binding fragments thereof comprise a heavy chain variable domain (VH) comprising an amino acid sequence at least 80% identical to an amino acid sequence set forth as SEQ ID NO: 8. In some embodiments, the monoclonal antibodies or antigen-binding fragments thereof selectively binds to a complex comprising an HLA-E and a neoantigen. In some embodiments, the monoclonal antibodies or antigen-binding fragments thereof do not have a binding affinity to the HLA-E alone. In some embodiments, the monoclonal antibodies or antigen-binding fragments thereof do not have a binding affinity to the neoantigen alone. In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL). In some embodiments, the HLA-E is HLA-E*0101 or HLA-E*0103. In some embodiments, the antibodies selectively binds to the complex comprising: the HLA-E*0101 and the neoantigen; the HLA-E*0103 and the neoantigen; or the HLA-E*0101 and the neoantigen, and the HLA-E*0103 and the neoantigen. In some embodiments, the monoclonal antibodies or antigen-binding fragments thereof are murine antibodies, chimeric antibodies, camelid antibodies, humanized antibodies, or human antibodies. In some embodiments, the monoclonal antibodies or antigen-binding fragments thereof are TCR-like antibodies. In some embodiments, the monoclonal antibodies or antigen-binding fragments thereof are multispecific antibodies. In some embodiments, the monoclonal antibodies or antigen-binding fragments thereof are bispecific antibodies. In some embodiments, the monoclonal antibodies or antigen-binding fragments thereof are bispecific T cell engagers (BiTE). In some embodiments, the BiTE binds to a CD3 protein associated with a T cell receptor (TCR). In some embodiments, the BiTE further comprises a light chain complementarity determining region (CDR) having an amino acid sequence at least 80% identical to at least one of the amino acid sequences set forth as SEQ ID NOS: 9-11. In some embodiments, the BiTE further comprises a heavy chain complementarity determining region (CDR) having an amino acid sequence at least 80% identical to at least one of the amino acid sequences set forth as SEQ ID NOS: 12-14. In some embodiments, the BiTE further comprises a light chain variable domain (VL) comprising an amino acid sequence at least 80% identical to an amino acid sequence set forth as SEQ ID NO: 15. In some embodiments, the BiTE further comprises a heavy chain variable domain (VH) comprising an amino acid sequence at least 80% identical to an amino acid sequence set forth as SEQ ID NO: 16. In some embodiments, the monoclonal antibodies or antigen-binding fragments thereof are multifunctional antibodies. In some embodiments, the monoclonal antibodies or antigen-binding fragments thereof antibody further comprise a conjugated therapeutic moiety. In some embodiments, the selective binding of the antibody to the complex comprising the HLA-E and the neoantigen induces an immune response in a cell. In some embodiments, the immune response comprises activation of (i) NK cells, (ii) T cells, or (iii) NK cells and T cells. In some embodiments, the T cell is a CD4+ T cell or a CD8+ T cell. In some embodiments, the immune response comprises activation of cytotoxic T cells (CTLs). In some embodiments, the cancer is breast cancer, kidney cancer, lung cancer, ovarian cancer, colorectal cancer, pancreatic cancer, choriocarcinoma, non-small cell lung carcinoma (NSCLC), gastric cancer, cervical cancer, or head and neck cancer. In some embodiments, the cancer is a myeloima, leukemia or lymphoma. In some embodiments, the cancer is acute myeloid leukemia (AML), multiple myeloma, or a myelodysplastic syndrome. In some embodiments, the cancer is a B cell malignancy. In some embodiments, the cancer is mantel cell lymphoma.

Disclosed herein, in certain embodiments, are methods of treating cancer in an individual in need thereof, comprising administering to the individual an effective amount of a bispecific antibody or an antigen-binding fragment thereof, comprising: a light chain complementarity determining region (CDR) having an amino acid sequence at least 80% identical to at least one of the amino acid sequences set forth as SEQ ID NOS: 1-3; or a heavy chain complementarity determining region (CDR) having an amino acid sequence at least 80% identical to at least one of the amino acid sequences set forth as SEQ ID NOS: 4-6; and a light chain complementarity determining region (CDR) having an amino acid sequence at least 80% identical to at least one of the amino acid sequences set forth as SEQ ID NOS: 9-11; or a heavy chain complementarity determining region (CDR) having an amino acid sequence at least 80% identical to at least one of the amino acid sequences set forth as SEQ ID NOS: 12-14. In some embodiments, the bispecific antibodies comprise: a light chain variable domain (VL) comprising an amino acid sequence at least 80% identical to an amino acid sequence set forth as SEQ ID NO: 7; or a heavy chain variable domain (VH) comprising an amino acid sequence at least 80% identical to an amino acid sequence set forth as SEQ ID NO: 8; and a light chain variable domain (VL) comprising an amino acid sequence at least 80% identical to an amino acid sequence set forth as SEQ ID NO: 15; or a heavy chain variable domain (VH) comprising an amino acid sequence at least 80% identical to an amino acid sequence set forth as SEQ ID NO: 16. Disclosed herein, in certain embodiments, are methods of treating cancer in an individual in need thereof, comprising administering to the individual an effective amount of a bispecific antibody or an antigen-binding fragment thereof, comprising: a light chain complementarity determining region (CDR) having an amino acid sequence at least 80% identical to at least one of the amino acid sequences set forth as SEQ ID NOS: 1-3; and a heavy chain complementarity determining region (CDR) having an amino acid sequence at least 80% identical to at least one of the amino acid sequences set forth as SEQ ID NOS: 4-6; and a light chain complementarity determining region (CDR) having an amino acid sequence at least 80% identical to at least one of the amino acid sequences set forth as SEQ ID NOS: 9-11; and a heavy chain complementarity determining region (CDR) having an amino acid sequence at least 80% identical to at least one of the amino acid sequences set forth as SEQ ID NOS: 12-14. In some embodiments, the bispecific antibodies comprise: a light chain variable domain (VL) comprising an amino acid sequence at least 80% identical to an amino acid sequence set forth as SEQ ID NO: 7; and a heavy chain variable domain (VH) comprising an amino acid sequence at least 80% identical to an amino acid sequence set forth as SEQ ID NO: 8; and a light chain variable domain (VL) comprising an amino acid sequence at least 80% identical to an amino acid sequence set forth as SEQ ID NO: 15; and a heavy chain variable domain (VH) comprising an amino acid sequence at least 80% identical to an amino acid sequence set forth as SEQ ID NO: 16. In some embodiments, the bispecific antibody or antigen-binding fragment thereof selectively binds to a complex comprising an HLA-E and a neoantigen. In some embodiments, the bispecific antibody or antigen-binding fragment thereof does not have a binding affinity to the HLA-E alone. In some embodiments, the bispecific antibody or antigen-binding fragment thereof does not have a binding affinity to the neoantigen alone. In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL). In some embodiments, the HLA-E is HLA-E*0101 or HLA-E*0103. In some embodiments, the bispecific antibodies selectively bind to the complex comprising: the HLA-E*0101 and the neoantigen; the HLA-E*0103 and the neoantigen; or the HLA-E*0101 and the neoantigen, and the HLA-E*0103 and the neoantigen. In some embodiments, the bispecific antibody or antigen-binding fragment thereof is a murine antibody, a chimeric antibody, a camelid antibody, a humanized antibody, or a human antibody. In some embodiments, the bispecific antibody or antigen-binding fragment thereof is a TCR-like antibody. In some embodiments, the bispecific antibody or antigen-binding fragment thereof is a bispecific T cell engager (BiTE). In some embodiments, the BiTE binds to a CD3 protein associated with a T cell receptor (TCR). In some embodiments, the bispecific antibody or antigen-binding fragment thereof is a multifunctional antibody. In some embodiments, the bispecific antibody or antigen-binding fragment thereof antibody further comprise a conjugated therapeutic moiety. In some embodiments, the selective binding of the antibody to the complex comprising the HLA-E and the neoantigen induces an immune response in a cell. In some embodiments, the immune response comprises activation of (i) NK cells, (ii) T cells, or (iii) NK cells and T cells. In some embodiments, the T cell is a CD4+ T cell or a CD8+ T cell. In some embodiments, the immune response comprises activation of cytotoxic T cells (CTLs). In some embodiments, the bispecific antibody is administered at a therapeutically effective amount. In some embodiments, the cancer is breast cancer, kidney cancer, lung cancer, ovarian cancer, colorectal cancer, pancreatic cancer, choriocarcinoma, non-small cell lung carcinoma (NSCLC), gastric cancer, cervical cancer, or head and neck cancer. In some embodiments, the cancer is a myeloima, leukemia or lymphoma. In some embodiments, the cancer is acute myeloid leukemia (AML), multiple myeloma, or a myelodysplastic syndrome. In some embodiments, the cancer is a B cell malignancy. In some embodiments, the cancer is mantel cell lymphoma.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A-FIG. 1D exemplifies identification and affinity characterization of clone R4 clone 1 (R4c1) against V-0025. (FIG. 1A) Phage and (FIG. 1B) monoclonal soluble ELISA. Antigen is at 1 µg/ml. (FIG. 1C) Binding affinity sensorgram and (FIG. 1D) kinetic data.

FIG. 2A-FIG. 2D are exemplary overview of sorting schematic for the isolation of affinity matured clones from R4c1 FIG. 2A-FIG. 2C exemplify cell sorting plots showing each round of sorting for the first round of affinity maturation. The 'star' indicates the sorted population. For the R4 sort (FIG. 2D), Koff was utilized with V-0025 at 10 nM using R4c1-IgG1 at 1 μM for the various timepoints as the antibody sink.

FIG. 3A-FIG. 3D exemplify binding profile to target antigen (V-0025) at 100 nM. FIG. 3E-FIG. 3G exemplify binding profile of the clone, R2A_1, to target (V-0025) at 10 nM and to additional peptide/HLA-E antigens at 100 nM.

FIG. 5A exemplifies binding to target (V-0025) by parent clone (R4 clone 1) and the starting affinity maturation library (R0) and first round sorted library (R1). FIG. 5B exemplifies Koff of R1 affinity maturation library. Target (V-0025) is at 10 nM, with R2A_1-hIgG1 as antibody sink at 1 μM for 15 minutes up to 90 minutes.

FIG. 9E shows target V-0025 used at 0.25 μg/mL while ABX0011 and HLA-E were titrated from 2 μg/mL down to 3.8 pg/mL ($3.8\times10^{-6}$ μg/mL). Thermostability of ABX0011 (FIG. 9F) was assessed by ELISA. ABX0011 binding to HLA-E/VMAPRTLFL (SEQ ID NO: 18) was evaluated after antibody was incubated in mouse serum at 37° C. for 7 to 14 days. Selectivity of binding (FIG. 9G) of clone 3D12 and ABX0011 to unpulsed and peptide-pulsed K562.E cells. K562.E cells were pulsed with 20 mM of peptide for 2 hrs followed by staining with antibody at 1 μg/mL. Further assessment of ABX0011 binding selectivity was performed using ABX0012 (ABX0011 with mouse IgG1) with related and unrelated peptides. HLA-E (FIG. 9H) and ABX0012 (FIG. 9I) staining on peptide-pulsed and unpulsed K562.E cells. The limit of detection for ABX0011 was determined with target V-0025 peptide pulsed K562.E (FIG. 9J). Controls were unpulsed K562.E cells and parent K562 (lack HLA-E expression) and K562.E cells pulsed with irrelevant peptides (V-0034, V-0044, V-0046 and P-0550). Epitope mapping for ABX0011 was carried out using K562.E cells pulsed with alanine substituted V-0025 peptides (FIG. 9K).

(FIG. 10A) Binding to IFNγ-stimulated JEG3 wild type (WT, top panel), $E^{ko}$ (middle panel) and Tap-$1^{ko}$ (bottom panel). (FIG. 10B) Binding to huPBMC and (FIG. 10C) to huVEC.

FIG. 17A shows specific redirected T-cell lysis of K562.E cells pulsed with V-0025 target peptide by ABX0030. Some lysis activity was observed for K562.E (unpulsed) cells when ABX0030 was used at 10,000 pM (highest concentration). CD8+ T cell CD25 and CD107a expression was also quantified to determine whether ABX0030 could non-specifically activate T cells. (FIG. 17B and FIG. 17C) ABX0030 exhibited minimal activation of CD8+ T-cells in the presence of K562.E unpulsed cells (no target).

FIG. 18A shows a dose-dependent effect (10000 to 80 pM) of ABX0030 to redirect CD8+ T-cell lysis of THP-1 cells. ABX0030 activated CD8+ T-cells in presence of THP-1 cells.

FIG. 18B shows ABX0030 dose-dependent effect on the frequency of CD25+CD8+ T-cells. Additional markers demonstrating ABX0030 effect on CD8+ T-cells in presence of THP-1 cells are an increase in frequency of CD107+CD8+ T-cells (FIG. 18C), and increases in the frequency of perforin (FIG. 18D) and IFNg (FIG. 18E) positive CD8+ T-cells.

DETAILED DESCRIPTION

Figure 1A:
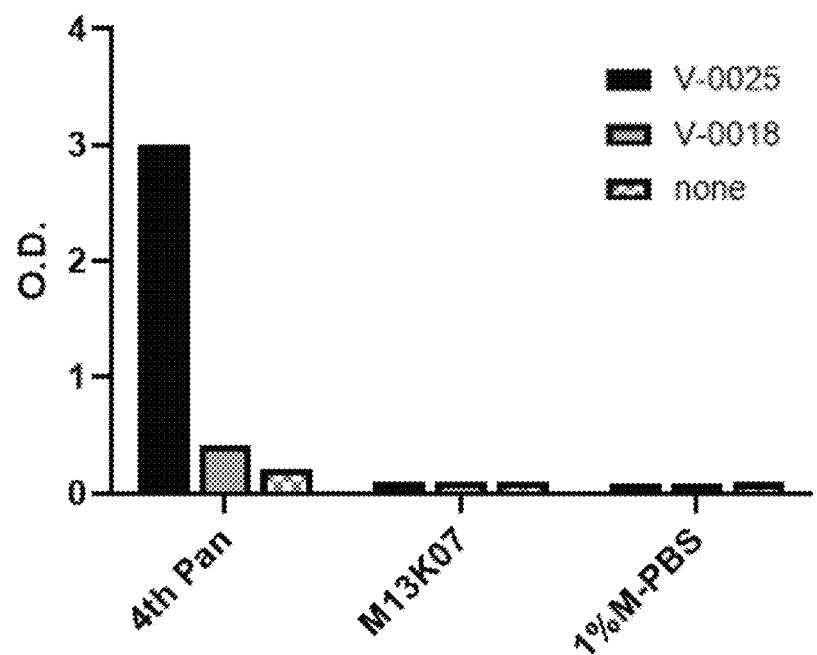

Disclosed herein, in certain embodiments, are antibodies comprising at least one heavy chain comprising a heavy chain variable domain (VH) and at least one light chain comprising a light chain variable domain (VL). Each VH and VL comprises three complementarity determining regions (CDR). In some embodiments, the antibodies are bispecific antibodies. In some embodiments, the bispecific antibodies are bispecific T cell engagers (BiTEs). In some embodiments, the bispecific antibodies bind to a CD3 protein associated with a T cell receptor (TCR). Further disclosed herein, in certain embodiments, are methods of treating a cancer by administering an antibody that selectively binds to a complex comprising a non-classical HLA-I (e.g. HLA-E) and a neoantigen. In some embodiments, the antibodies that selectively bind to a complex comprising a non-classical HLA-I (e.g. HLA-E) and a neoantigen modulate immune response against cancer cells, thereby treating cancer. In some embodiments, the antibodies are bispecific antibodies.

Traditional approaches to the treatment of cancers have included surgery, radiation, chemotherapy and hormone therapy. However, such therapies have not proven effective by themselves. Development of alternate remedies for preventing and/or treating cancer is crucial. More recently immunotherapy and gene therapy approaches utilizing antibodies and T-lymphocytes have emerged as new and promising methods for treating cancer.

Major histocompatibility complex (MHC) molecules, designated human leukocyte antigen (HLA) in humans, play a critical role in the body's recognition of disease and the resulting immune response to cancer and invading antigens. The HLA gene family is divided into two subgroups namely HLA Class I (HLA-I) and HLA Class II (HLA-II), with HLA-I further divided into classical HLA-I and non-classical HLA-I. Each HLA molecule forms a complex with one peptide from within the cell. On cancer cells, some of the peptide/HLA complexes are uniquely presented which enables the immune system to recognize and kill these cells. Cells decorated with these unique peptide/HLA complexes are recognized and killed by the cytotoxic T cells (CTLs). Cancer cells show a downregulation in classical HLA-I expression but an upregulation in non-classical HLA-I expression (e.g. HLA-E). Thus, the upregulated uniquely presented non-classical HLA-I-peptide complexes on cancer cells are novel targets for developing innovative immunotherapies for treatment of cancer.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. The section headings used herein are for organizational purposes only and are not to be construed as limiting the subject matter described.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

As used herein, the term "MHC" refers to the Major Histocompatibility Complex, which is a set of gene loci specifying major histocompatibility antigens. The term "HLA" as used herein refer to Human Leukocyte Antigens, which are the histocompatibility antigens found in humans. As used herein, "HLA" is the human form of "MHC" and the terms are used interchangeably.

As used herein "antibody" refers to a glycoprotein which exhibits binding specificity to a specific antigen. Antibodies herein also include "antigen binding portion" or fragments of the antibody that are capable of binding to the antigen. The term includes, but is not limited to, polyclonal, monoclonal, monospecific, multispecific (e.g., bispecific antibodies), natural, humanized, human, chimeric, synthetic, recombinant, hybrid, mutated, grafted, antibody fragments (e.g., a portion of a full-length antibody, generally the antigen binding or variable region thereof, e.g., Fab, Fab', F(ab')2, and Fv fragments), and in vitro generated antibodies so long as they exhibit the desired biological activity. The term also includes single chain antibodies, e.g., single chain Fv (sFv or scFv) antibodies, in which a variable heavy and a variable light chain are joined together (directly or through a peptide linker) to form a continuous polypeptide.

As used herein "CDR" refers to an immunoglobulin (Ig) hypervariable domain. A CDR is defined by any suitable manner. In some embodiments, CDRs can be defined in accordance with any of the Chothia numbering schemes, the Kabat numbering scheme, a combination of Kabat and Chothia, the AbM definition, the contact definition, and/or a combination of the Kabat, Chothia, AbM, and/or contact definitions; and may produce different results.

As used herein, the term "selectively binds" in the context of any binding agent, e.g., an antibody, refers to a binding agent that binds specifically to an antigen or epitope, such as with a high affinity, and does not significantly bind other unrelated antigens or epitopes.

As used herein the term "neoantigen" or "neopeptide" are used interchangeably and refer to a peptide differentially expressed by a diseased or stressed cell (e.g. cancer cell) compared to a healthy cell.

The terms "recipient", "individual", "subject", "host", and "patient", are used interchangeably herein and in some cases, refer to any mammalian subject for whom diagnosis, treatment, or therapy is desired, particularly humans. None of these terms require the supervision of medical personnel.

As used herein, the terms "treatment," "treating," and the like, in some cases, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with diseases (e.g. cancer). The term "therapeutic effect" refers to the reduction, elimination, or prevention of the disease, symptoms of the disease, or side effects of the disease in the subject.

A "therapeutically effective amount" in some cases means the amount that, when administered to a subject for treating a disease, is sufficient to effect treatment for that disease.

"Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO: Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

Major Histocompatibility Complex (MHC) or Human Leukocyte Antigens (HLA)

Major histocompatibility complexes (MHC), also termed Human Leukocyte Antigens (HLA) in humans are glycoproteins expressed on the surface of nucleated cells that act as proteomic scanning chips by providing insight into the status of cellular health. They continuously sample peptides from normal host cellular proteins, cancer cells, inflamed cells and bacterial, viral and parasite infected cells and present short peptides on the surface of cells for recognition by T lymphocytes. Presented peptides can also be derived from proteins that are out of frame or from sequences embedded in the introns, or from proteins whose translation is initiated at codons other than the conventional methionine codon, ATG.

There are two classes of MHCs in mice and humans, namely MHC I and MHC II. WIC I comprises classical and non-classical MHC I sub-groups.

Classical MHC I or HLA-I

Classical WIC I molecules include HLA-A, HLA-B and HLA-C in humans and H-2-K, H-2-D, H-2-B and H-2-L in mice. Classical MHC I molecules are highly polymorphic with more than 2,735 alleles of HLA-A, 3,455 alleles of HLA-B and 2,259 alleles of HLA-C. Classical MHC I is expressed on the surface of all nucleated cells and present peptides to CD8 T lymphocytes. 30% of the proteins in the cellular machinery are rapidly degraded and are primary substrates for classical WIC I antigen presentation.

For peptide to be presented by classical MHC I molecules, proteins are first processed through the conventional processing route (ubiquitin proteasome system) which begins with protein degradation in the proteasome and Transporter associated protein (TAP) dependent transport of peptides into the endoplasmic reticulum (ER) and ends with the loading of peptides into the HLA peptide binding pocket. The proteins that contribute to the conventional processing route are collectively known as antigen processing machinery (APM) and include the proteasome, TAP complex, tapasin, endoplasmic reticulum amino peptidase (ERAAP), binding immunoglobulin protein (BiP), clanexin and calreticulin. Cells lacking either proteasome subunits, TAP1/2, ErP57 or calreticulin have reduced numbers of classical MHC I molecules on their surface.

Non-Classical MHC I or HLA-I

Non-classical MHC I molecules include HLA-E, HLA-F and HLA-G, and have limited polymorphisms. They play a role in regulating innate and adaptive immune responses. Non-classical MHC I molecules present peptides generated by both the conventional processing route and the alternative processing route in health and disease states, and represent a novel set of markers for targeting in disease states (e.g. cancer).

HLA-E

The non-classical MHC class I molecule, HLA-E is non-polymorphic. In nature, 13 HLA-E alleles have been identified with only two functional variants, namely HLAE*0101 and HLA-E*0103. The difference between HLA-E*0101 (HLA-E$^{107R}$) and *0103 (HLA-E$^{107G}$) is a single amino acid difference at position 107 which is outside the peptide binding pocket. Similar to the classical MHC I molecules, HLA-E is expressed in all cells with a nucleus, however at usually lower levels. HLA-E molecule expression in cells and tissues is generally increased during stress and disease. As such, HLA-E is differentially expressed on stressed or diseased cell (e.g. cancer cell) compared to on a healthy cell.

In healthy cells, HLA-E presents peptides derived from classical MHC molecules and the non-classical HLA-G molecule to either inhibit or stimulate the activity of NK cells and a subset of CD8 T cells through engaging the receptor CD94/NKG2. Depending on the particular peptide presented by HLA-E, the HLA-E complex engages either CD94/NKG2A or CD94/NKG2C to inhibit or activate NK cells and a subset of CD8 T cells, respectively.

Another signal peptide that has characteristics in common with signal peptides generated from classical HLA-I molecules is the signal peptide generated from non-classical HLA-G. HLA-G expression under normal physiologic conditions is tightly regulated, with limited expression found in relatively few tissues and cells in the body. HLA-G plays a key role as an immune tolerant molecule and its expression is observed in cancer tissue/cells. Moreover, the signal peptide from HLA-G is processed by the conventional antigen processing pathway and delivered to the endoplasmic reticulum by the peptide transporter TAP. In some embodiments, the signal peptide is VMAPRTLFL (SEQ ID NO: 18).

HLA-E Expression and Peptide Presentation in Cancer Cells

Cells deficient in one or more components of the APM load peptides into MHC class I molecules via alternative processing routes which are independent of the APM-dependent conventional processing route. APM-deficient cells not only have reduced numbers of classical MHC I molecules on their surface, but also show an increase in the cell surface density of HLA-E molecules as well as an increase in the repertoire of peptides presented. The alternative processing routes are constitutively turned on and produce peptides in both healthy and diseased cells. These peptides, however, are not presented by healthy cells; instead they are only presented in diseased or stressed cells. As such, the different peptide repertoires generated by APM-defective cells, also known as "T-cell epitopes associated with impaired peptide processing" (TEIPP), represent novel targets unique to cancer cells, and represent ideal targets for therapeutic development in the treatment of cancer.

In a stressed or diseased state (e.g. cancer), the stressed or diseased cell (e.g. a cancer cell) differentially expresses a complex comprising an HLA-E and a peptide derived from the non-classical HLA-G molecule. The complex comprising an HLA-E and a peptide derived from the non-classical HLA-G molecule is differentially expressed on the stressed or diseased cell compared to a healthy cell. Targeting this complex induces an immune response against the cell expressing the complex.

MHC II or HLA-H

MHC II molecules in humans include HLA-DM, HLA-DO, HLA-DP, HLA-DQ and HLA-DR and include H-2 I-A and H-2 I-E in mice. MHC II expression is more restricted to B cells, dendritic cells, macrophages, activated T cells and thymic epithelial cells and MHC II molecules present peptides to CD4 lymphocytes.

Antibodies that Target a Complex Comprising a Non-Classical HLA-I (e.g. HLA-E) and a Neoantigen Disclosed herein, in certain embodiments, are antibodies that target a complex comprising a non-classical HLA-I (e.g. HLA-E) and a neoantigen. In some embodiments, the antibodies comprise at least one heavy chain comprising a heavy chain variable domain (VH) and at least one light chain comprising a light chain variable domain (VL). Each VH and VL comprises three complementarity determining regions (CDR). The amino acid sequences of the VH and VL and the CDRs determine the antigen binding specificity and antigen binding strength of the antibody. The amino acid sequences of the VH and VL and the CDRs are summarized in Table 1.

TABLE 1

Antibodies

Human monoclonal antibody sequences that bind a complex comprising HLA-E and classical HLA signal peptides (ABX-0010, 0011, 0030)

| | SEQUENCE | SEQ ID NO: |
|---|---|---|
| Light Chain CDR1 | QSISSY | 1 |
| Light Chain CDR2 | AAS | 2 |
| Light Chain CDR3 | QQAAAYPSL | 3 |
| Heavy Chain CDR1 | GFTFSSYA | 4 |
| Heavy Chain CDR2 | IAYGGGAT | 5 |
| Heavy Chain CDR3 | AKGLSNFDY | 6 |
| Light Chain Variable domain | DIQMTQSPSSLSASVGDRVTITCRASQSISSYLNWYQQ KPGKAPKLLIYAASSLQSGVPSRFSGSGSGTDFTLTISS LQPEDFATYYCQQAAAYPSLFGQGTKVEIK | 7 |
| Heavy Chain Variable domain | EVQLLESGGGLVQPGGSLRLSCAASGFTFSSYAMSWV RQAPGKGLEWVSTIAYGGGATAYADSVKGRFTISRDN SKNTLYLQMNSLRAEDTAVYYCAKGLSNFDYWGQG TLVTVSS | 8 |

Mouse monoclonal antibody sequences binding CD3

| | | |
|---|---|---|
| Light Chain CDR1 | TGAVTTSNY | 9 |
| Light Chain CDR2 | GTN | 10 |
| Light Chain CDR3 | ALWYSNLWV | 11 |
| Heavy Chain CDR1 | GFTFNTYA | 12 |
| Heavy Chain CDR2 | IRSKYNNYAT | 13 |
| Heavy Chain CDR3 | VRHGNFNSYVSWFAYG | 14 |
| Light Chain Variable domain | QAVVTQESALTTSPGETVTLTCRSSTGAVTTSNYANWV QEKPDHLF TGLIGGTNKRAPGVPARFSGSLIGDKAALTI TGAQTEDEAIYFCALWYSNLWVFGGGTKLTVL | 15 |
| Heavy Chain Variable domain | EVQLVESGGGLVQPKGSLKLSCAASGFTFNTYANINW VRQAPGKGLEWVARIRSKYNNYATYYADSVKDRFTIS RDDSQSILYLQMNNLKTEDTAMYYCVRHGNFGNSYV SWFAYWGQGTLVTVSS | 16 |

In some embodiments, the antibodies selectively bind to a complex comprising a non-classical HLA-I (e.g. HLA-E) and a neoantigen. In some embodiments, the antibody does not have a binding affinity to the non-classical HLA-I alone. In some embodiments, the antibody does not have a binding affinity to the neoantigen alone. In some embodiments, the antibody does not have a binding affinity to a complex comprising the non-classical HLA-I and a non-relevant neoantigen.

In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL).

In some embodiments, the non-classical HLA-I is HLA-E, HLA-F, HLA-G, or HLA-H. In some embodiments, the non-classical HLA-I is HLA-E. In some embodiments, the HLA-E is HLA-E*0101. In some embodiments, the HLA-E is HLA-E*0103.

In some embodiments, the antibody selectively binds to the complex comprising the HLA-E and the neoantigen. In some embodiments, the antibody selectively binds to the complex comprising the HLA-E*0101 and the neoantigen. In some embodiments, the antibody selectively binds to the complex comprising the HLA-E*0103 and the neoantigen. In some embodiments, the antibody selectively binds to the complex comprising the HLA-E*0101 and the neoantigen, and to the complex of the HLA-E*0103 and the neoantigen. In some embodiments, the complex comprises the HLA-E and a neoantigen according to SEQ ID NO: 18 (VMAPRTLFL).

In some embodiments, the antibody is a murine antibody. In some embodiments, the antibody is a chimeric antibody. In some embodiments, the antibody is a camelid antibody. In some embodiments, the antibody is a humanized antibody. In some embodiments, the antibody is a human antibody.

In some embodiments, the antibody is a TCR-like antibody. In some embodiments, the antibody is a single domain antibody. In some embodiments, the single domain antibody is a camelid single domain antibody.

In some embodiments, the antibody is a multispecific antibody. In some embodiments, the antibody is a bispecific antibody. In some embodiments, the antibody is a bispecific T cell engager (BiTE). In some embodiments, the BiTE binds to a CD3 protein associated with a T cell receptor (TCR). In some embodiments, the BiTE binds to a CD3ϵ protein associated with a T cell receptor (TCR). In some embodiments, the antibody is a multifunctional antibody.

In some embodiments, the antibody further comprises a conjugated therapeutic moiety. Therapeutic moiety include, but are not limited to, a cytotoxin, a chemotherapeutic drug, an immunosuppressant, and a radioisotope. A cytotoxin or cytotoxic agent includes any agent that is detrimental to (e.g., kills) cells. Examples include, but are not limited to, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable chemotherapeutic agents include, but are not limited to, anti metabolites (e.g., methotrexate, 6-mercaptopurine, 6-thioguanine, cytarabine, fludarabin, 5-fluorouracil, decarbazine, hydroxyurea, azathiprin, gemcitabin and cladribin), alkylating agents (e.g., mechlorethamine, thioepa, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, docetaxel, paclitaxel and vinorelbin). Suitable radioisotopes include, but are not limited to, iodine-131, yttrium-90 or indium-Ill. Further examples of therapeutic moieties are a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In some embodiments, the selective binding of the antibody to the complex comprising the non-classical HLA-I (e.g. HLA-E) and the neoantigen induces an immune response. In some embodiments, the immune response comprises activation of NK cells. In some embodiments, the selective binding of the antibody to the CD3 protein associated with a TCR induces an immune response. In some embodiments, the immune response comprises activation of T cells. In some embodiments, the T cell is a CD8+ T cell. In some embodiments, the immune response comprises activation of cytotoxic T cells (CTLs). In some embodiments, the cell is a cancer cell.

Antibody Variable Domain (VL and VH)

Disclosed herein are antibodies that selectively bind to a complex comprising an HLA-E and a neoantigen, the antibodies having a light chain comprising a light chain variable domain (VL). In some embodiments, antibodies comprise a light chain variable domain (VL) having an amino acid sequence at least about 70% identical to an amino acid sequence set forth as SEQ ID NO: 7. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. In some embodiments, the VL has an amino acid sequence 100% identical to an amino acid sequence set forth as SEQ ID NO: 7.

Further disclosed herein are antibodies that selectively bind to a complex comprising an HLA-E and a neoantigen, the antibodies having a heavy chain comprising a heavy chain variable domain (VH). In some embodiments, antibodies comprise a heavy chain variable domain (VH) having an amino acid sequence at least about 70% identical to an amino acid sequence set forth as SEQ ID NO: 8. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VH has an amino acid sequence 100% identical to an amino acid sequence set forth as SEQ ID NO: 8.

Also disclosed herein are antibodies that selectively bind to a complex comprising an HLA-E and a neoantigen, the antibodies comprising a light chain variable domain (VL) and a heavy chain variable domain (VH). In some embodiments, antibodies comprise a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

Antibody Complementarity Determining Regions (CDR)

Disclosed herein are antibodies that selectively bind to a complex comprising an HLA-E and a neoantigen, the antibodies having a light chain comprising a light chain complementarity determining region (CDR). In some embodiments, antibodies comprise a light chain CDR sequence having an amino acid sequence at least about 70% identical to at least one of the amino acid sequences set forth as SEQ ID NOS: 1-3. In some embodiments, antibodies comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3. In some embodiments, antibodies comprise a light chain CDR sequence having an amino acid sequence 100% identical to at least one of the amino acid sequences set forth as SEQ ID NOS: 1-3.

Further disclosed herein are antibodies that selectively bind to a complex comprising an HLA-E and a neoantigen, the antibodies having a heavy chain comprising a heavy chain complementarity determining region (CDR). In some embodiments, antibodies comprise a heavy chain CDR sequence having an amino acid sequence at least about 70% identical to at least one of the amino acid sequences set forth as SEQ ID NOS: 4-6. In some embodiments, antibodies comprise a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6. In some embodiments, antibodies comprise a heavy chain CDR sequence having an amino acid sequence 100% identical to at least one of the amino acid sequences set forth as SEQ ID NOS: 4-6.

Also disclosed herein are antibodies that selectively bind to a complex comprising an HLA-E and a neoantigen comprise a light chain complementarity determining region (CDR) and a heavy chain complementarity determining region (CDR). In some embodiments, antibodies comprise a light chain CDR sequence having an amino acid sequence at least about 70% identical to at least one of the amino acid sequences set forth as SEQ ID NOS: 1-3 and a heavy chain CDR sequence having an amino acid sequence at least about 70% identical to at least one of the amino acid sequences set forth as SEQ ID NOS: 4-6. In some embodiments, antibodies comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3 and a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6. In some embodiments, antibodies comprise a light chain CDR sequence having an amino acid sequence 100% identical to at least one of the amino acid sequences set forth as SEQ ID NOS: 1-3 and a heavy chain CDR sequence having an amino acid sequence at least about 100% identical to at least one of the amino acid sequences set forth as SEQ ID NOS: 4-6.

In some embodiments, antibodies selectively bind to a complex comprising an HLA-E and a neoantigen comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies that selectively bind to a complex comprising an HLA-E and a neoantigen comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, antibodies comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

In some embodiments, antibodies that selectively bind to a complex comprising an HLA-E and a neoantigen comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, antibodies comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 8'7%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

Bispecific Antibodies

In some embodiments, the antibodies disclosed herein are bispecific antibodies. In some embodiments, the bispecific antibodies are bispecific T cell engagers (BiTEs). In some embodiments, the BiTE binds to a CD3 protein associated with a T cell receptor (TCR). In some embodiments, the BiTE binds to a CD3c protein associated with a T cell receptor (TCR).

In some embodiments, the BiTE comprises an anti-CD3 antibody, or a fragment thereof, such as UCHT1, OKT3, F6A, L2K, muromonab, otelixizumab, teplizumab, visilizumab, CD3-12, MEM-57, 4D10A6, CD3D, or TR66.

In some embodiments, the bispecific antibodies comprise (a) a light chain variable domain (VL) comprising an amino acid sequence at least 70% identical to an amino acid sequence set forth as SEQ ID NO: 7; or a heavy chain variable domain (VH) comprising an amino acid sequence at least 70% identical to an amino acid sequence set forth as SEQ ID NO: 8; and (b) a light chain variable domain (VL) comprising an amino acid sequence at least 70% identical to an amino acid sequence set forth as SEQ ID NO: 15; or a heavy chain variable domain (VH) comprising an amino acid sequence at least 70% identical to an amino acid sequence set forth as SEQ ID NO: 16.

In some embodiments, the bispecific antibodies comprise (a) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7; or a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8; and (b) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15; or a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16.

In some embodiments, the bispecific antibodies comprise (a) a light chain variable domain (VL) comprising an amino acid sequence 100% identical to an amino acid sequence set forth as SEQ ID NO: 7; or a heavy chain variable domain (VH) comprising an amino acid sequence 100% identical to an amino acid sequence set forth as SEQ ID NO: 8; and (b) a light chain variable domain (VL) comprising an amino acid sequence 100% identical to an amino acid sequence set forth as SEQ ID NO: 15; or a heavy chain variable domain (VH) comprising an amino acid sequence 100% identical to an amino acid sequence set forth as SEQ ID NO: 16.

In some embodiments, the bispecific antibodies comprise (a) a light chain variable domain (VL) comprising an amino acid sequence at least 70% identical to an amino acid sequence set forth as SEQ ID NO: 7; and a heavy chain variable domain (VH) comprising an amino acid sequence at least 70% identical to an amino acid sequence set forth as SEQ ID NO: 8; and (b) a light chain variable domain (VL) comprising an amino acid sequence at least 70% identical to an amino acid sequence set forth as SEQ ID NO: 15; and a heavy chain variable domain (VH) comprising an amino acid sequence at least 70% identical to an amino acid sequence set forth as SEQ ID NO: 16.

In some embodiments, the bispecific antibodies comprise (a) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7; and a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8; and (b) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15; and a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16.

In some embodiments, the bispecific antibodies comprise (a) a light chain variable domain (VL) comprising an amino acid sequence 100% identical to an amino acid sequence set forth as SEQ ID NO: 7; and a heavy chain variable domain (VH) comprising an amino acid sequence 100% identical to an amino acid sequence set forth as SEQ ID NO: 8; and (b) a light chain variable domain (VL) comprising an amino acid sequence 100% identical to an amino acid sequence set forth as SEQ ID NO: 15; and a heavy chain variable domain (VH) comprising an amino acid sequence 100% identical to an amino acid sequence set forth as SEQ ID NO: 16.

In some embodiments, the bispecific antibodies comprise (a) a light chain complementarity determining region (CDR) having an amino acid sequence at least 70% identical to at least one of the amino acid sequences set forth as SEQ ID NOS: 1-3; or a heavy chain complementarity determining region (CDR) having an amino acid sequence at least 70% identical to at least one of the amino acid sequences set forth as SEQ ID NOS: 4-6; and (b) a light chain complementarity determining region (CDR) having an amino acid sequence at least 70% identical to at least one of the amino acid sequences set forth as SEQ ID NOS: 9-11; or a heavy chain complementarity determining region (CDR) having an amino acid sequence at least 70% identical to at least one of the amino acid sequences set forth as SEQ ID NOS: 12-14.

In some embodiments, the bispecific antibodies comprise (a) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3; or a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6; and (b) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 9-11; or a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 12-14.

In some embodiments, the bispecific antibodies comprise (a) a light chain complementarity determining region (CDR) having an amino acid sequence 100% identical to at least one of the amino acid sequences set forth as SEQ ID NOS: 1-3; or a heavy chain complementarity determining region (CDR) having an amino acid sequence 100% identical to at least one of the amino acid sequences set forth as SEQ ID NOS: 4-6; and (b) a light chain complementarity determining region (CDR) having an amino acid sequence 100% identical to at least one of the amino acid sequences set forth as SEQ ID NOS: 9-11; or a heavy chain complementarity determining region (CDR) having an amino acid sequence 100% identical to at least one of the amino acid sequences set forth as SEQ ID NOS: 12-14.

In some embodiments, the bispecific antibodies comprise (a) a light chain complementarity determining region (CDR) having an amino acid sequence at least 70% identical to at least one of the amino acid sequences set forth as SEQ ID NOS: 1-3; and a heavy chain complementarity determining region (CDR) having an amino acid sequence at least 70% identical to at least one of the amino acid sequences set forth as SEQ ID NOS: 4-6; and (b) a light chain complementarity determining region (CDR) having an amino acid sequence at least 70% identical to at least one of the amino acid sequences set forth as SEQ ID NOS: 9-11; and a heavy chain complementarity determining region (CDR) having an amino acid sequence at least 70% identical to at least one of the amino acid sequences set forth as SEQ ID NOS: 12-14.

In some embodiments, the bispecific antibodies comprise (a) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3; and a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6; and (b) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 9-11; and a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 12-14.

In some embodiments, the bispecific antibodies comprise (a) a light chain complementarity determining region (CDR) having an amino acid sequence 100% identical to at least one of the amino acid sequences set forth as SEQ ID NOS: 1-3; and a heavy chain complementarity determining region (CDR) having an amino acid sequence 100% identical to at least one of the amino acid sequences set forth as SEQ ID NOS: 4-6; and (b) a light chain complementarity determining region (CDR) having an amino acid sequence 100% identical to at least one of the amino acid sequences set forth as SEQ ID NOS: 9-11; and a heavy chain complementarity determining region (CDR) having an amino acid sequence 100% identical to at least one of the amino acid sequences set forth as SEQ ID NOS: 12-14.

Methods of Treatment

Provided herein are methods of treating cancer in an individual in need thereof comprising administration of an antibody that selectively bind to a complex comprising a non-classical HLA-I (e.g. HLA-E) and a neoantigen as disclosed herein.

In some embodiments, the antibody selectively binds to a complex comprising a non-classical HLA-I (e.g. HLA-E) and a neoantigen. In some embodiments, the antibody does not have a binding affinity to the non-classical HLA-I alone. In some embodiments, the antibody does not have a binding affinity to the neoantigen alone. In some embodiments, the antibody does not have a binding affinity to a complex comprising the non-classical HLA-I and a non-relevant neoantigen.

In some embodiments, the neoantigen is expressed by an antigen processing machinery (APM)-proficient cell. In some embodiments, the neoantigen is expressed by a TAP1/2-proficient cell. In some embodiments, the neoantigen comprises, consists essentially of, or consists of a sequence according to SEQ ID NO: 18 (VMAPRTLFL).

In some embodiments, the non-classical HLA-I is HLA-E, HLA-F, HLA-G, or HLA-H. In some embodiments, the non-classical HLA-I is HLA-E. In some embodiments, the HLA-E is HLA-E*0101. In some embodiments, the HLA-E is HLA-E*0103.

In some embodiments, the antibody selectively binds to the complex comprising the HLA-E and the neoantigen. In some embodiments, the antibody selectively binds to the complex comprising the HLA-E*0101 and the neoantigen. In some embodiments, the antibody selectively binds to the complex comprising the HLA-E*0103 and the neoantigen. In some embodiments, the antibody selectively binds to the complex comprising the HLA-E*0101 and the neoantigen, and to the complex of the HLA-E*0103 and the neoantigen. In some embodiments, the complex comprises the HLA-E and a neoantigen according to SEQ ID NO: 18 (VMAPRTLFL).

In some embodiments, the antibody comprises a light chain variable domain (VL) having an amino acid sequence at least about 70% identical to an amino acid sequence set forth as SEQ ID NO: 7. In some embodiments, the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. In some embodiments, the VL has an amino acid sequence 100% identical to an amino acid sequence set forth as SEQ ID NO: 7.

In some embodiments, the antibody comprises a heavy chain variable domain (VH) having an amino acid sequence at least about 70% identical to an amino acid sequence set forth as SEQ ID NO: 8. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VH has an amino acid sequence 100% identical to an amino acid sequence set forth as SEQ ID NO: 8.

In some embodiments, the antibody comprises a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

In some embodiments, the antibody comprises a light chain CDR sequence having an amino acid sequence at least about 70% identical to at least one of the amino acid sequences set forth as SEQ ID NOS: 1-3. In some embodiments, the antibody comprises a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3. In some embodiments, the antibody comprises a light chain CDR sequence having an amino acid sequence 100% identical to at least one of the amino acid sequences set forth as SEQ ID NOS: 1-3.

In some embodiments, the antibody comprises a heavy chain CDR sequence having an amino acid sequence at least about 70% identical to at least one of the amino acid sequences set forth as SEQ ID NOS: 4-6. In some embodiments, the antibody comprises a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6. In some embodiments, the antibody comprises a heavy chain CDR sequence having an amino acid sequence 100% identical to at least one of the amino acid sequences set forth as SEQ ID NOS: 4-6.

In some embodiments, the antibody comprises a light chain CDR sequence having an amino acid sequence at least about 70% identical to at least one of the amino acid sequences set forth as SEQ ID NOS: 1-3 and a heavy chain CDR sequence having an amino acid sequence at least about 70% identical to at least one of the amino acid sequences set forth as SEQ ID NOS: 4-6. In some embodiments, the antibody comprises a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3 and a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6. In some embodiments, the antibody comprises a light chain CDR sequence having an amino acid sequence 100% identical to at least one of the amino acid sequences set forth as SEQ ID NOS: 1-3 and a heavy chain CDR sequence having an amino acid sequence at least about 100% identical to at least one of the amino acid sequences set forth as SEQ ID NOS: 4-6.

In some embodiments, the antibody comprises an HLA-E and a neoantigen comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, the antibody comprises at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, the antibody comprises at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, the antibody comprises an HLA-E and a neoantigen comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, the antibody comprises at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, the antibody comprises at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

In some embodiments, the antibody comprises an HLA-E and a neoantigen comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, the antibody comprises at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, the antibody comprises at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

In some embodiments, the antibody is a bispecific antibody. In some embodiments, the bispecific antibody comprises (a) a light chain variable domain (VL) comprising an amino acid sequence at least 70% identical to an amino acid sequence set forth as SEQ ID NO: 7; or a heavy chain variable domain (VH) comprising an amino acid sequence at least 70% identical to an amino acid sequence set forth as SEQ ID NO: 8; and (b) a light chain variable domain (VL) comprising an amino acid sequence at least 70% identical to an amino acid sequence set forth as SEQ ID NO: 15; or a heavy chain variable domain (VH) comprising an amino acid sequence at least 70% identical to an amino acid sequence set forth as SEQ ID NO: 16.

In some embodiments, the bispecific antibody comprises (a) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7; or a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8; and (b) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15; or a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16.

In some embodiments, the bispecific antibody comprises (a) a light chain variable domain (VL) comprising an amino acid sequence 100% identical to an amino acid sequence set forth as SEQ ID NO: 7; or a heavy chain variable domain (VH) comprising an amino acid sequence 100% identical to an amino acid sequence set forth as SEQ ID NO: 8; and (b) a light chain variable domain (VL) comprising an amino acid sequence 100% identical to an amino acid sequence set forth as SEQ ID NO: 15; or a heavy chain variable domain (VH) comprising an amino acid sequence 100% identical to an amino acid sequence set forth as SEQ ID NO: 16.

In some embodiments, the bispecific antibody comprises (a) a light chain variable domain (VL) comprising an amino acid sequence at least 70% identical to an amino acid sequence set forth as SEQ ID NO: 7; and a heavy chain variable domain (VH) comprising an amino acid sequence at least 70% identical to an amino acid sequence set forth as SEQ ID NO: 8; and (b) a light chain variable domain (VL) comprising an amino acid sequence at least 70% identical to an amino acid sequence set forth as SEQ ID NO: 15; and a heavy chain variable domain (VH) comprising an amino acid sequence at least 70% identical to an amino acid sequence set forth as SEQ ID NO: 16.

In some embodiments, the bispecific antibody comprises (a) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7; and a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8; and (b) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15; and a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16.

In some embodiments, the bispecific antibody comprises (a) a light chain variable domain (VL) comprising an amino acid sequence 100% identical to an amino acid sequence set forth as SEQ ID NO: 7; and a heavy chain variable domain (VH) comprising an amino acid sequence 100% identical to an amino acid sequence set forth as SEQ ID NO: 8; and (b) a light chain variable domain (VL) comprising an amino acid sequence 100% identical to an amino acid sequence set forth as SEQ ID NO: 15; and a heavy chain variable domain (VH) comprising an amino acid sequence 100% identical to an amino acid sequence set forth as SEQ ID NO: 16.

In some embodiments, the bispecific antibody comprises (a) a light chain complementarity determining region (CDR) having an amino acid sequence at least 70% identical to at least one of the amino acid sequences set forth as SEQ ID NOS: 1-3; or a heavy chain complementarity determining region (CDR) having an amino acid sequence at least 70% identical to at least one of the amino acid sequences set forth as SEQ ID NOS: 4-6; and (b) a light chain complementarity determining region (CDR) having an amino acid sequence at least 70% identical to at least one of the amino acid sequences set forth as SEQ ID NOS: 9-11; or a heavy chain complementarity determining region (CDR) having an amino acid sequence at least 70% identical to at least one of the amino acid sequences set forth as SEQ ID NOS: 12-14.

In some embodiments, the bispecific antibody comprises (a) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3; or a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6; and (b) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 9-11; or a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 12-14.

In some embodiments, the bispecific antibody comprises (a) a light chain complementarity determining region (CDR) having an amino acid sequence 100% identical to at least one of the amino acid sequences set forth as SEQ ID NOS: 1-3; or a heavy chain complementarity determining region (CDR) having an amino acid sequence 100% identical to at least one of the amino acid sequences set forth as SEQ ID NOS: 4-6; and (b) a light chain complementarity determining region (CDR) having an amino acid sequence 100% identical to at least one of the amino acid sequences set forth as SEQ ID NOS: 9-11; or a heavy chain complementarity determining region (CDR) having an amino acid sequence 100% identical to at least one of the amino acid sequences set forth as SEQ ID NOS: 12-14.

In some embodiments, the bispecific antibody comprises (a) a light chain complementarity determining region (CDR) having an amino acid sequence at least 70% identical to at least one of the amino acid sequences set forth as SEQ ID NOS: 1-3; and a heavy chain complementarity determining region (CDR) having an amino acid sequence at least 70% identical to at least one of the amino acid sequences set forth as SEQ ID NOS: 4-6; and (b) a light chain complementarity determining region (CDR) having an amino acid sequence at least 70% identical to at least one of the amino acid sequences set forth as SEQ ID NOS: 9-11; and a heavy chain complementarity determining region (CDR) having an amino acid sequence at least 70% identical to at least one of the amino acid sequences set forth as SEQ ID NOS: 12-14.

In some embodiments, the bispecific antibody comprises (a) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3; and a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6; and (b) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 9-11; and a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 12-14.

In some embodiments, the bispecific antibody comprises (a) a light chain complementarity determining region (CDR) having an amino acid sequence 100% identical to at least one of the amino acid sequences set forth as SEQ ID NOS: 1-3; and a heavy chain complementarity determining region (CDR) having an amino acid sequence 100% identical to at least one of the amino acid sequences set forth as SEQ ID NOS: 4-6; and (b) a light chain complementarity determining region (CDR) having an amino acid sequence 100% identical to at least one of the amino acid sequences set forth as SEQ ID NOS: 9-11; and a heavy chain complementarity determining region (CDR) having an amino acid sequence 100% identical to at least one of the amino acid sequences set forth as SEQ ID NOS: 12-14.

In some embodiments, the antibody is a murine antibody. In some embodiments, the antibody is a chimeric antibody. In some embodiments, the antibody is a camelid antibody. In some embodiments, the antibody is a humanized antibody. In some embodiments, the antibody is a human antibody.

In some embodiments, the antibody is a TCR-like antibody. In some embodiments, the antibody is a single domain antibody. In some embodiments, the single domain antibody is a camelid single domain antibody.

In some embodiments, the antibody is a multispecific antibody. In some embodiments, the antibody is a bispecific antibody. In some embodiments, the antibody is a bispecific T cell engager (BiTE). In some embodiments, the BiTE binds to a CD3 protein associated with a T cell receptor (TCR). In some embodiments, the BiTE binds to a CD3c protein associated with a T cell receptor (TCR). In some embodiments, the antibody is a multifunctional antibody.

In some embodiments, the antibody further comprises a conjugated therapeutic moiety. Therapeutic moiety include, but are not limited to, a cytotoxin, a chemotherapeutic drug, an immunosuppressant, and a radioisotope. A cytotoxin or cytotoxic agent includes any agent that is detrimental to (e.g., kills) cells. Examples include, but are not limited to, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable chemotherapeutic agents include, but are not limited to, anti metabolites (e.g., methotrexate, 6-mercaptopurine, 6-thioguanine, cytarabine, fludarabin, 5-fluorouracil, decarbazine, hydroxyurea, azathiprin, gemcitabin and cladribin), alkylating agents (e.g., mechlorethamine, thioepa, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, docetaxel, paclitaxel and vinorelbin). Suitable radioisotopes include, but are not limited to, iodine-131, yttrium-90 or indium-Ill. Further examples of therapeutic moieties are a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In some embodiments, the selective binding of the antibody to the complex comprising the non-classical HLA-I (e.g. HLA-E) and the neoantigen induces an immune response. In some embodiments, the immune response comprises activation of NK cells. In some embodiments, the selective binding of the antibody to the CD3 protein associated with a TCR induces an immune response. In some embodiments, the immune response comprises activation of T cells. In some embodiments, the T cell is a CD8+ T cell. In some embodiments, the immune response comprises activation of cytotoxic T cells (CTLs).

In some embodiments, the cancer is breast cancer. In some embodiments, the cancer is kidney cancer. In some embodiments, the cancer is lung cancer. In some embodiments, the cancer is ovarian cancer. In some embodiments, the cancer is colorectal cancer. In some embodiments, the cancer is pancreatic cancer. In some embodiments, the cancer is choriocarcinoma. In some embodiments, the cancer is non-small cell lung carcinoma (NSCLC). In some embodiments, the cancer is gastric cancer. In some embodiments, the cancer is cervical cancer. In some embodiments, the cancer is head and neck cancer. In some embodiments, the cancer is a myeloma. In some embodiments, the cancer is a leukemia. In some embodiments, the cancer is a lymphoma. In some embodiments, the cancer is acute myeloid leukemia (AML). In some embodiments, the cancer is multiple myeloma. In some embodiments, the cancer is a myelodysplastic syndrome. In some embodiments, the cancer is a B-cell malignancy. In some embodiments, the cancer is mantel cell lymphoma.

In some embodiments, the cancer cell differentially expresses the neoantigen. In some embodiments, the cancer cell differentially expresses the HLA-E. In some embodiments, the cancer cell differentially expresses the complex comprising the HLA-E and the neoantigen.

Any suitable route of administration is contemplated for use with the methods disclosed herein. In some embodiments, the antibody is administered by intravenous administration. In some embodiments, the antibody is administered by subcutaneous administration. In some embodiments, the antibody is administered locally. In some embodiments, the antibody is administered systemically (e.g., intravenously, intramuscularly, subcutaneously, intradermally, orally, intranasally, sublingually). In some embodiments, the antibody is formulated as a salve, lotion or emulsion. In some embodiments, the antibody is formulated as a solution. In some embodiments, the antibody is formulated for topical, oral, buccal, or nasal administration.

In some embodiments, the individual is monitored prior to administration of the antibody. Symptoms are identified and their severity is assessed. An antibody as described herein is administered alone or in combination with additional treatments, singly or multiply over time as discussed herein or known to one of skill in the art. In some embodiments, the individual is monitored such that the efficacy of the treatment regimen is determined. In some embodiments, a treatment regimen is modified in response to preliminary treatment outcomes, such that treatment dose or frequency or dose and frequency is altered so as to attain a desired level of subject response in light of symptom alleviation, side effect reduction, or a combination of symptom alleviation and side effect reduction.

Pharmaceutical Compositions

Also disclosed herein are pharmaceutical compositions comprising (a) an antibody that selectively bind to a complex comprising a non-classical HLA-I (e.g. HLA-E) and a neoantigen as disclosed herein and (b) a pharmaceutically acceptable carrier or excipient.

In some embodiments, the antibody comprises a light chain variable domain (VL) having an amino acid sequence at least about 70% identical to an amino acid sequence set forth as SEQ ID NO: 7. In some embodiments, the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. In some embodiments, the VL has an amino acid sequence 100% identical to an amino acid sequence set forth as SEQ ID NO: 7.

In some embodiments, the antibody comprises a heavy chain variable domain (VH) having an amino acid sequence at least about 70% identical to an amino acid sequence set forth as SEQ ID NO: 8. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VH has an amino acid sequence 100% identical to an amino acid sequence set forth as SEQ ID NO: 8.

In some embodiments, the antibody comprises a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

In some embodiments, the antibody comprises a light chain CDR sequence having an amino acid sequence at least about 70% identical to at least one of the amino acid sequences set forth as SEQ ID NOS: 1-3. In some embodiments, the antibody comprises a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3. In some embodiments, the antibody comprises a light chain CDR sequence having an amino acid sequence 100% identical to at least one of the amino acid sequences set forth as SEQ ID NOS: 1-3.

In some embodiments, the antibody comprises a heavy chain CDR sequence having an amino acid sequence at least about 70% identical to at least one of the amino acid sequences set forth as SEQ ID NOS: 4-6. In some embodiments, the antibody comprises a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6. In some embodiments, the antibody comprises a heavy chain CDR sequence having an amino acid sequence 100% identical to at least one of the amino acid sequences set forth as SEQ ID NOS: 4-6.

In some embodiments, the antibody comprises a light chain CDR sequence having an amino acid sequence at least about 70% identical to at least one of the amino acid sequences set forth as SEQ ID NOS: 1-3 and a heavy chain CDR sequence having an amino acid sequence at least about 70% identical to at least one of the amino acid sequences set forth as SEQ ID NOS: 4-6. In some embodiments, the antibody comprises a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3 and a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6. In some embodiments, the antibody comprises a light chain CDR sequence having an amino acid sequence 100% identical to at least one of the amino acid sequences set forth as SEQ ID NOS: 1-3 and a heavy chain CDR sequence having an amino acid sequence at least about 100% identical to at least one of the amino acid sequences set forth as SEQ ID NOS: 4-6.

In some embodiments, the antibody comprises an HLA-E and a neoantigen comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, the antibody comprises at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, the antibody comprises at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, the antibody comprises an HLA-E and a neoantigen comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, the antibody comprises at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, the antibody comprises at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

In some embodiments, the antibody comprises an HLA-E and a neoantigen comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, the antibody comprises at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, the antibody comprises at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

In some embodiments, the antibody is a bispecific antibody. In some embodiments, the bispecific antibody comprises (a) a light chain variable domain (VL) comprising an amino acid sequence at least 70% identical to an amino acid sequence set forth as SEQ ID NO: 7; or a heavy chain variable domain (VH) comprising an amino acid sequence at least 70% identical to an amino acid sequence set forth as SEQ ID NO: 8; and (b) a light chain variable domain (VL) comprising an amino acid sequence at least 70% identical to an amino acid sequence set forth as SEQ ID NO: 15; or a heavy chain variable domain (VH) comprising an amino acid sequence at least 70% identical to an amino acid sequence set forth as SEQ ID NO: 16.

In some embodiments, the bispecific antibody comprises (a) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7; or a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8; and (b) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15; or a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16.

In some embodiments, the bispecific antibody comprises (a) a light chain variable domain (VL) comprising an amino acid sequence 100% identical to an amino acid sequence set forth as SEQ ID NO: 7; or a heavy chain variable domain (VH) comprising an amino acid sequence 100% identical to an amino acid sequence set forth as SEQ ID NO: 8; and (b) a light chain variable domain (VL) comprising an amino acid sequence 100% identical to an amino acid sequence set forth as SEQ ID NO: 15; or a heavy chain variable domain (VH) comprising an amino acid sequence 100% identical to an amino acid sequence set forth as SEQ ID NO: 16.

In some embodiments, the bispecific antibody comprises (a) a light chain variable domain (VL) comprising an amino acid sequence at least 70% identical to an amino acid sequence set forth as SEQ ID NO: 7; and a heavy chain variable domain (VH) comprising an amino acid sequence at least 70% identical to an amino acid sequence set forth as SEQ ID NO: 8; and (b) a light chain variable domain (VL) comprising an amino acid sequence at least 70% identical to an amino acid sequence set forth as SEQ ID NO: 15; and a heavy chain variable domain (VH) comprising an amino acid sequence at least 70% identical to an amino acid sequence set forth as SEQ ID NO: 16.

In some embodiments, the bispecific antibody comprises (a) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7; and a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8; and (b) a light chain variable domain (VL) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15; and a heavy chain variable domain (VH) comprising an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16.

In some embodiments, the bispecific antibody comprises (a) a light chain variable domain (VL) comprising an amino acid sequence 100% identical to an amino acid sequence set forth as SEQ ID NO: 7; and a heavy chain variable domain (VH) comprising an amino acid sequence 100% identical to an amino acid sequence set forth as SEQ ID NO: 8; and (b) a light chain variable domain (VL) comprising an amino acid sequence 100% identical to an amino acid sequence set forth as SEQ ID NO: 15; and a heavy chain variable domain (VH) comprising an amino acid sequence 100% identical to an amino acid sequence set forth as SEQ ID NO: 16.

In some embodiments, the bispecific antibody comprises (a) a light chain complementarity determining region (CDR) having an amino acid sequence at least 70% identical to at least one of the amino acid sequences set forth as SEQ ID NOS: 1-3; or a heavy chain complementarity determining region (CDR) having an amino acid sequence at least 70% identical to at least one of the amino acid sequences set forth as SEQ ID NOS: 4-6; and (b) a light chain complementarity determining region (CDR) having an amino acid sequence at least 70% identical to at least one of the amino acid sequences set forth as SEQ ID NOS: 9-11; or a heavy chain complementarity determining region (CDR) having an amino acid sequence at least 70% identical to at least one of the amino acid sequences set forth as SEQ ID NOS: 12-14.

In some embodiments, the bispecific antibody comprises (a) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3; or a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6; and (b) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 9-11; or a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 12-14.

In some embodiments, the bispecific antibody comprises (a) a light chain complementarity determining region (CDR) having an amino acid sequence 100% identical to at least one of the amino acid sequences set forth as SEQ ID NOS: 1-3; or a heavy chain complementarity determining region (CDR) having an amino acid sequence 100% identical to at least one of the amino acid sequences set forth as SEQ ID NOS: 4-6; and (b) a light chain complementarity determining region (CDR) having an amino acid sequence 100% identical to at least one of the amino acid sequences set forth as SEQ ID NOS: 9-11; or a heavy chain complementarity determining region (CDR) having an amino acid sequence 100% identical to at least one of the amino acid sequences set forth as SEQ ID NOS: 12-14.

In some embodiments, the bispecific antibody comprises (a) a light chain complementarity determining region (CDR) having an amino acid sequence at least 70% identical to at least one of the amino acid sequences set forth as SEQ ID NOS: 1-3; and a heavy chain complementarity determining region (CDR) having an amino acid sequence at least 70% identical to at least one of the amino acid sequences set forth as SEQ ID NOS: 4-6; and (b) a light chain complementarity determining region (CDR) having an amino acid sequence at least 70% identical to at least one of the amino acid sequences set forth as SEQ ID NOS: 9-11; and a heavy chain complementarity determining region (CDR) having an amino acid sequence at least 70% identical to at least one of the amino acid sequences set forth as SEQ ID NOS: 12-14.

In some embodiments, the bispecific antibody comprises (a) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3; and a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6; and (b) a light chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 9-11; and a heavy chain complementarity determining region (CDR) having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 12-14.

In some embodiments, the bispecific antibody comprises (a) a light chain complementarity determining region (CDR) having an amino acid sequence 100% identical to at least one of the amino acid sequences set forth as SEQ ID NOS: 1-3; and a heavy chain complementarity determining region (CDR) having an amino acid sequence 100% identical to at least one of the amino acid sequences set forth as SEQ ID NOS: 4-6; and (b) a light chain complementarity determining region (CDR) having an amino acid sequence 100% identical to at least one of the amino acid sequences set forth as SEQ ID NOS: 9-11; and a heavy chain complementarity determining region (CDR) having an amino acid sequence 100% identical to at least one of the amino acid sequences set forth as SEQ ID NOS: 12-14.

In some embodiments, excipients for use with the compositions disclosed herein include maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In some embodiments, the compositions further comprise an additional therapeutic agent. In some embodiments, the therapeutic agent is a chemotherapeutic agent. The chemotherapeutic agents can include, among others, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, vinca alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors.

In some embodiments, the antibody and the therapeutic agent are in the same formulation. In some embodiments, the antibody and the therapeutic agent are in different formulation. In some embodiments, antibody described herein is used prior to the administration of the other therapeutic agent. In some embodiments, antibody described herein is used concurrently with the administration of the other therapeutic agent. In some embodiments, antibody described herein is used subsequent to the administration of the other therapeutic agent.

Pharmaceutical formulations are made to be compatible with a particular local, regional or systemic administration or delivery route. Thus, pharmaceutical formulations include carriers, diluents, or excipients suitable for administration by particular routes. Specific non-limiting examples of routes of administration for compositions herein are parenteral, e.g., intravenous, intra-arterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

Solutions or suspensions used for parenteral application include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. In some embodiments, pH is adjusted with acids or bases, such as hydrochloric acid or sodium hydroxide.

Pharmaceutical formulations for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In some embodiments, the carrier is a solvent or dispersion medium containing, for example, water, ethanol, polyol (for example, glycerol, propylene glycol, and liquid polyetheylene glycol, and the like), or suitable mixtures thereof. Fluidity is maintained, in some embodiments, for example, by the use of a coating such as lecithin, by the maintenance of the required particle size in the case of dispersion, and by the use of surfactants. Antibacterial and antifungal agents include, for example, parabens, chlorobutanol, phenol, ascorbic acid, and thimerosal. Isotonic agents, for example, sugars; polyalcohols such as mannitol or sorbitol; or sodium chloride, in some embodiments, are included in the composition. In some cases, also included is an agent which delays absorption, for example, aluminum monostearate or gelatin prolongs absorption of injectable compositions.

Sterile injectable formulations are prepared by incorporating the active composition in the required amount in an appropriate solvent with one or a combination of above ingredients. Generally, dispersions are prepared by incorporating the active composition into a sterile vehicle containing a basic dispersion medium and any other ingredient. In the case of sterile powders for the preparation of sterile injectable solutions, methods of preparation include, for example, vacuum drying and freeze-drying which yields a powder of the active ingredient plus any additional desired ingredient from a previously prepared solution thereof.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. In some embodiments, transmucosal administration is accomplished through the use of nasal sprays, inhalation devices (e.g., aspirators) or suppositories. For transdermal administration, the active compounds are formulated into ointments, salves, gels, creams or patches.

In some embodiments, the pharmaceutical formulations are prepared with carriers that protect against rapid elimination from the body, such as a controlled release formulation or a time delay material such as glyceryl monostearate or glyceryl stearate. The formulations, in some embodiments, are also delivered using articles of manufacture such as implants and microencapsulated delivery systems to achieve local, regional or systemic delivery or controlled or sustained release.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Generation of Antibodies

Figure 1B:
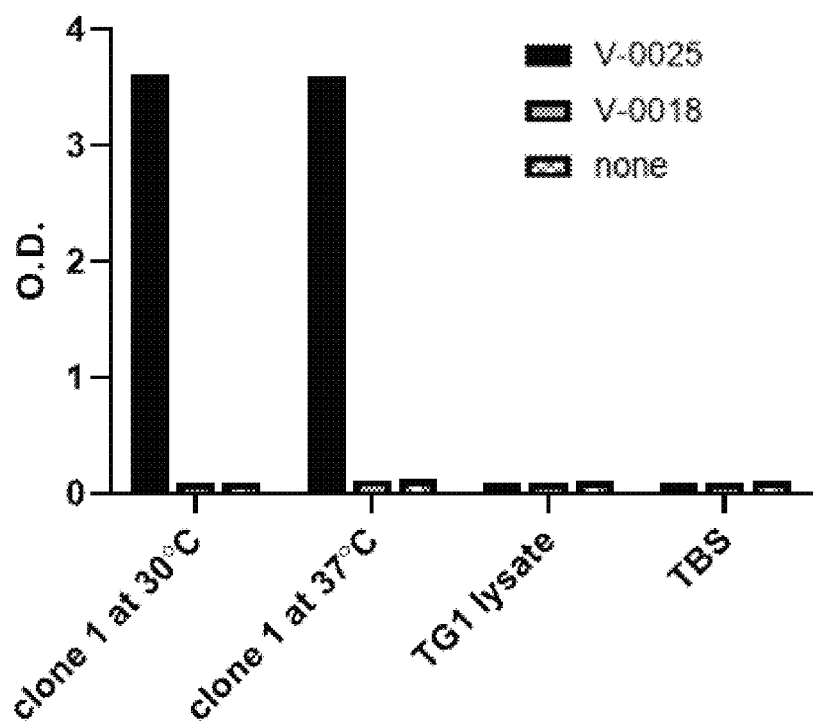

R4 clone 1 (R4c1) was first isolated from a semi-synthetic human antibody phage library. In brief, this was performed as follows. A human scFv antibody phage display library ($1.42 \times 10^9$ clones) constructed by Creative Biolabs (HuScL-2 phage library) was used to screen against HLA-G signal peptide/HLA-E*0103 complex (ABI-V-0025; VMAPRTLFL (SEQ ID NO: 18)). Briefly, 30 µg of a mix of five internal peptide/HLA-A2*0201 complexes (ABI-AV-007-Biot, ABI-AV-0010-Biot, ABI-AV-0014-Biot, ABI-AV-0019 and ABI-AB-0030-Biot) were used for depletion and pre-blocking, followed by enrichment with 50 µg of ABI-V-0025. The enrichment factor of the phage library was $2.73 \times 10^6$ (phage input: $5 \times 10^{11}$, phage output: $1.83 \times 10^5$). This process was repeated for the second round of biopanning, with an enrichment factor of $4.03 \times 10^2$. This process was repeated for the third round of biopanning, but using 20 µg of the complex mix for depletion (enrichment factor $2.31 \times 10^2$). For the fourth round of biopanning, 50 µg of ABI-V-0018 was used for depletion and pre-blocking, followed by enrichment with 50 µg of ABI-V-0025 (enrichment factor 44). From the phage output of the fourth round of biopanning, 40 clones were picked and sequenced, revealing one unique sequence. This clone was designated as R4 clone 1 (R4c1) (FIG. 1A-FIG. 1B). To determine affinity of the R4c1 antibody it was diluted in 0.1% BSA, 0.1% Tween20, PBS dilution/wash buffer and immobilized on the ForteBio Octet Protein A biosensor tip at 20 ug/ml for 50 seconds. Tips were subsequently washed in dilution/wash buffer for 50 seconds. Antibody binding association was measured using six concentrations (serial dilutions starting at 100 ug/ml in dilution/wash buffer) of canonical 0025-E 01:03 monomer complex over the course of 150 seconds immediately followed by dissociation (dilution/wash buffer) for 150 seconds (FIG. 1C). The equilibrium dissociation constant (KD) for clone R4 (clone 1) was determined to be 411 nM (FIG. 1D).

Affinity Maturation of R4c1: Cycle 2:

To increase the binding affinity of clone R4c1 to V-0025, the R4c1 scFv construct was cloned into a yeast vector to create a library of R4c1 mutants by changing two amino acid in the CDRH3 region. In brief, the yeast display library generated used EBY100 yeast competent cells that were prepared for transformation by incubation in 100 mM lithium acetate (LiAc, Sigma) plus 10 mM Dithiothreitol (DTT, Sigma). Electroporation was achieved using a GenePulser (BioRad) with 60 OD prepared yeast per 2 mm cuvette (BioRad) in 10 mM LiAc, with 1 µg of scFv clones and 100 ng of pYES3 (ThermoFisher) altered to include Aga2 after the GAL1 promoter and a Flag (DYKDDDDK) epitope tag (SEQ ID NO: 19) after the scFv. To determine the number of transformants, 100 µL of 1/10, 1/100 and 1/1000 dilutions of transformed yeast were spread on glucose plates minus tryptophan and uracil (D-UT, Teknova). Transformation efficiency was calculated after incubation at 30° C. for 2 days. Random clones were then picked for insertion diversity by PCR. Yeast were grown at 30° C. with shaking at 200 rpm in CM broth with glucose minus tryptophan and uracil (D-UT, Teknova). scFv surface induction was achieved by growing yeast for at least 20 hrs in CM broth with galactose minus tryptophan and uracil (G-UT, Teknova) supplemented with 0.1% raffinose (Sigma) (GR-UT).

Yeast were stained after first blocking with 2% BSA in PBS 0.05% tween (blocking buffer) for 30 minutes to 1 hour at room temperature with rotation. Yeast were than incubated with biotinylated peptide/HLA complex monomers on ice for 30 minutes to 90 minutes, depending on monomer concentration. Secondary labeling was achieved with Streptaivdin PE (ThermoFisher) and DYKDDDDK epitope tag (SEQ ID NO: 19) Alexa Fluor 488 (R&D Systems) on ice for 30 minutes. Samples were acquired using a LSR II flow cytometer (BD Biosciences) or a CytoFLEX S (Beckmen Coulter). Data was prepared using Flowjo Software version 10 or FACSDiva (BD Biosciences).

Screening was achieved by either magnetic-activated cell sorting (MACS) or fluorescence-activated cell sorting (FACS), using at least ten-fold coverage of the library size. For MACS screening, yeast were first blocked with 2% BSA in PBS 0.05% tween (blocking buffer) for 30 minutes to 1 hour at room temperature with rotation. Biotinylated peptide/HLA complex monomers were than incubated on ice for 30 minutes at 1 µM. Secondary labeling was achieved using streptavidin microbeads (Miltenyi Biotec). Labeled yeast were poured over a MACS Column on a MACS Separator (Miltenyi Biotec). Yeast bound to the column were harvested and considered as an enriched population. For FACS screening, yeast were prepared as described in the flow cytometry section. Samples were sorted using a FACS Aria II (BD Bioscience). Sorted yeast were considered an enriched population.

Unique scFv clones were identified by plating. After two days at 30° C., individual colonies were picked and analyzed by PCR. Full-length human IgG1 of the selected clones were produced in Expi293F (ThermoFisher) cells. Briefly, antibody variable regions were subcloned into mammalian expression vectors, with matching human kappa light-chain constant region (pFUSE2ss-CLIg-hK, Invivogen) and human IgG1 constant region (pFUSEss-CHIg-hG1, Invivogen) sequences. Vectors were transfected at a 2:3 light chain:heavy chain ratio. Antibodies were purified with protein A resin (Genscript) and confirmed in reducing and non-reducing conditions by electrophoresis.

Figure 2B:
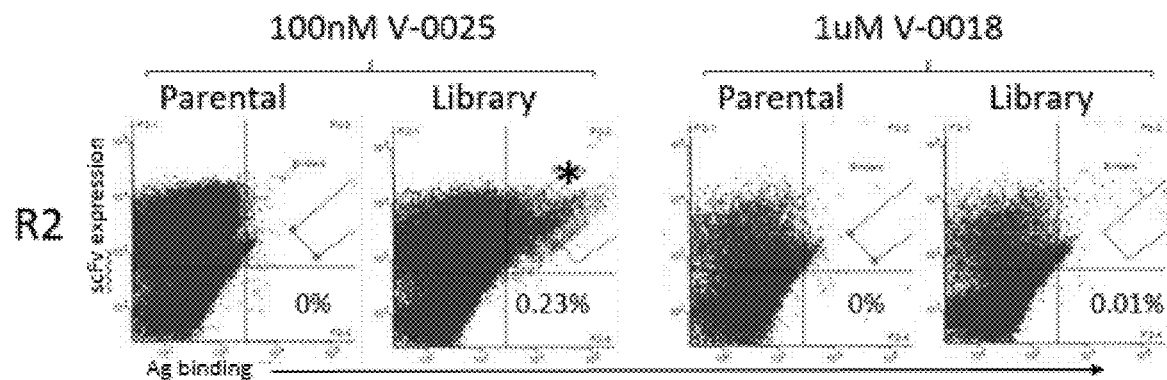
Figure 2C:
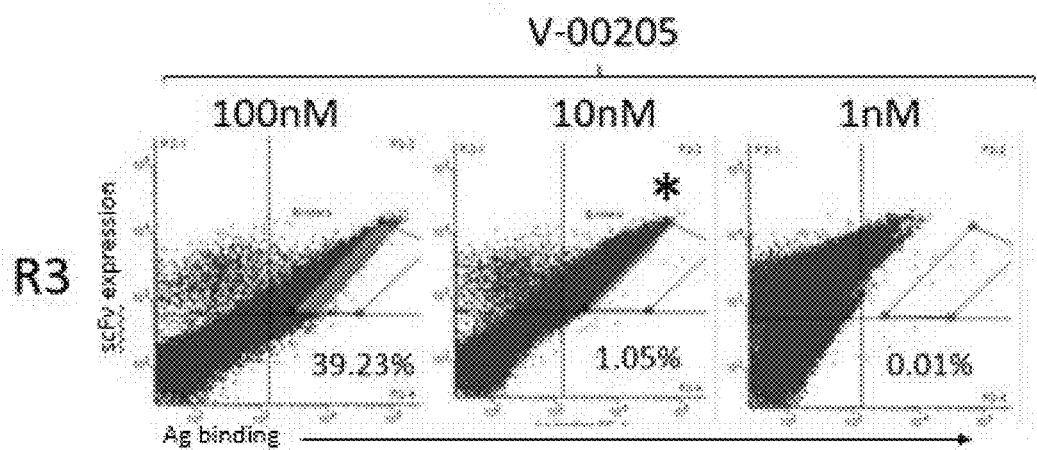
Figure 2D:
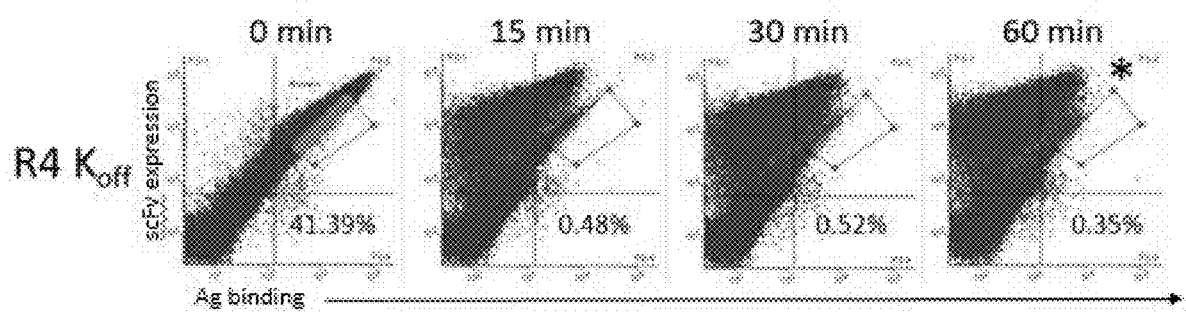
Figure 3A:
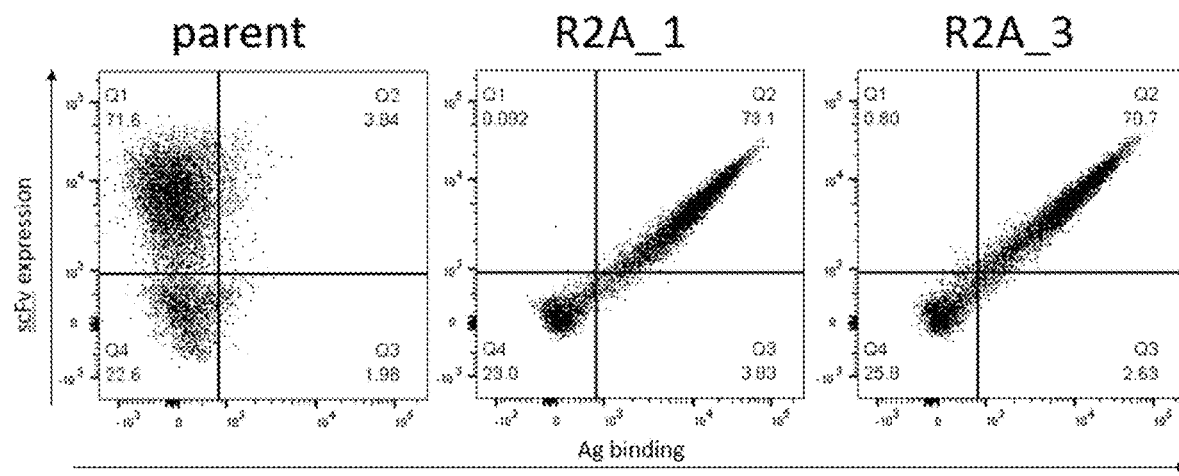
FIG. 3A-FIG. 3G exemplify clones identified from affinity maturation of R4c1.
Figure 3B:
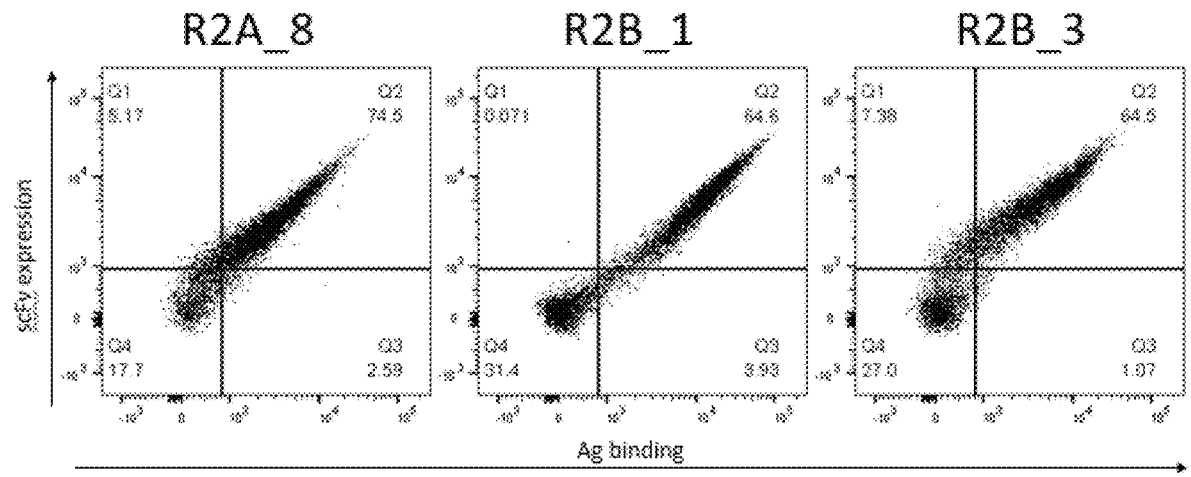
Figure 3C:
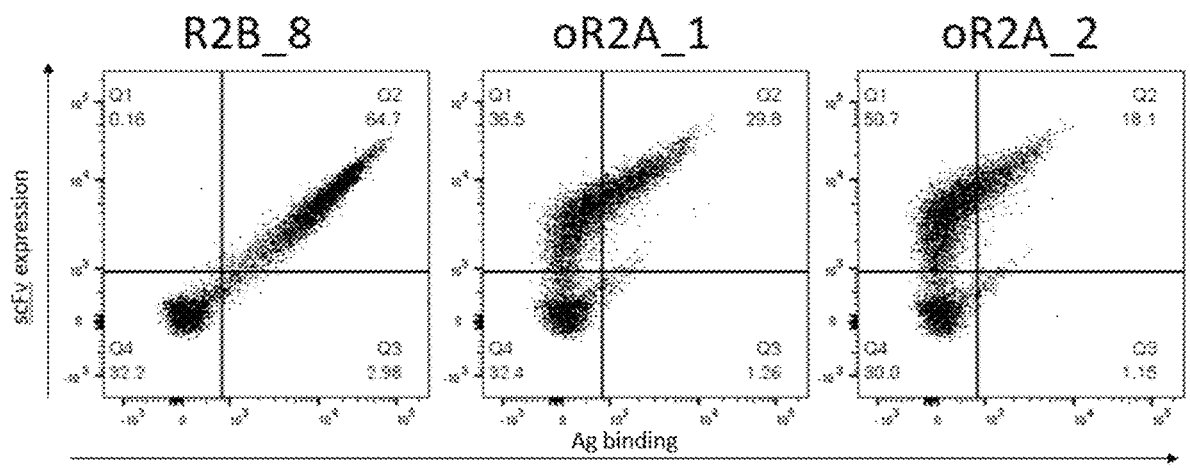
Figure 3D:
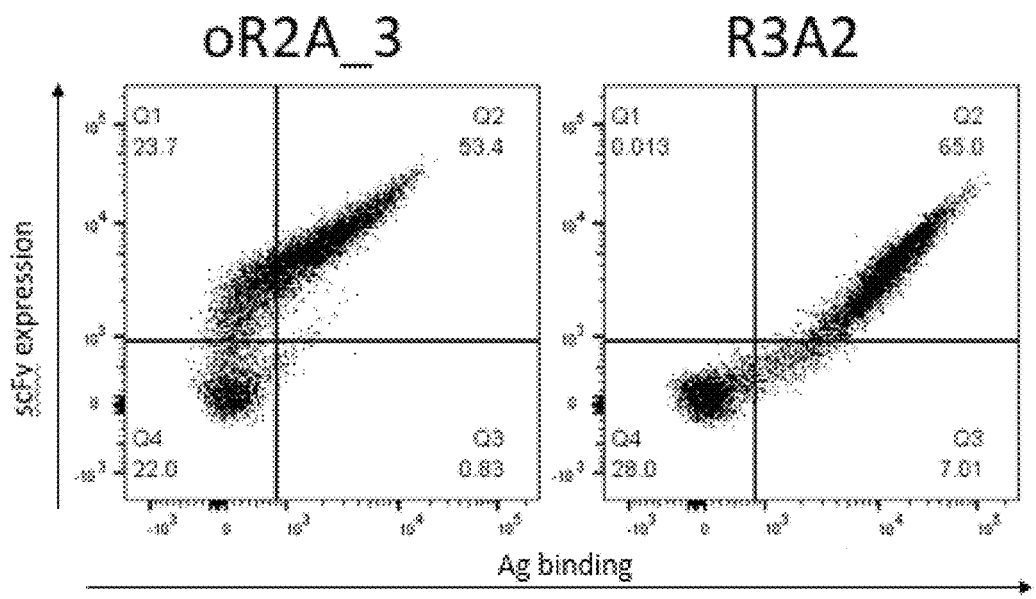
Figure 3E:
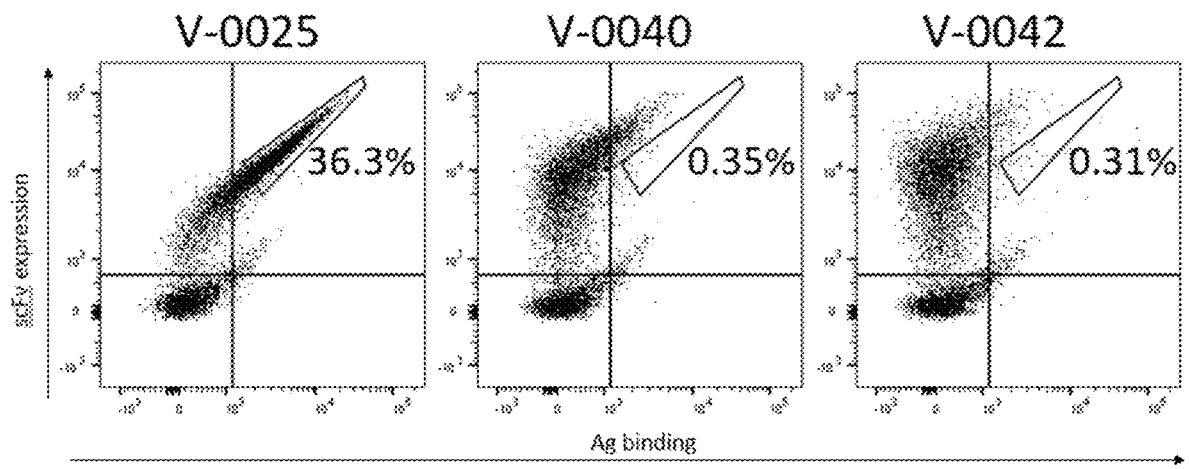
Figure 3F:
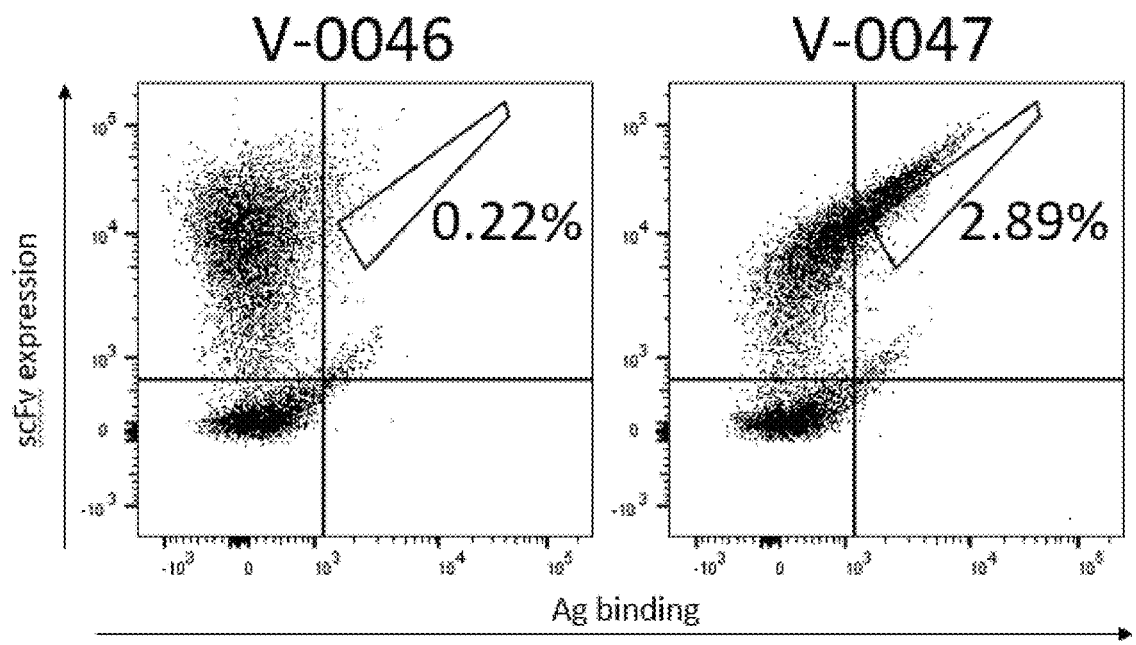
Figure 3G:
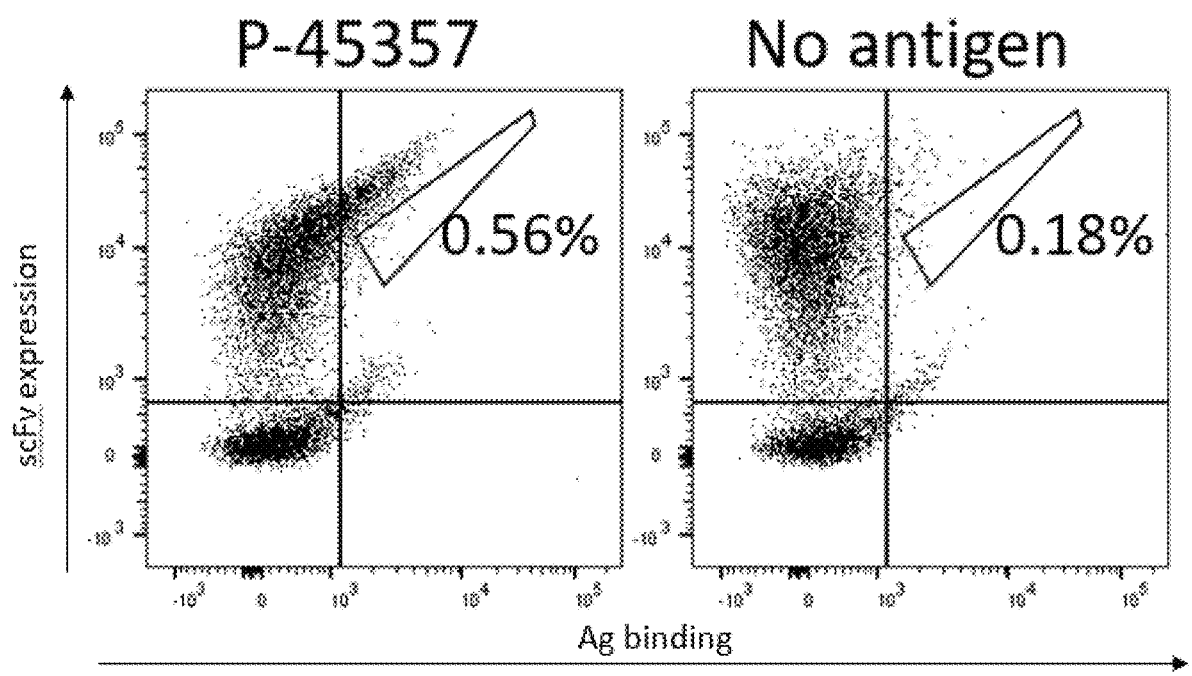

The first round of selection was performed using 1 µM of V-0025. Gating was based on binding by the parent (R4c1); parent exhibited 0.11% to V-0025 while the cycle 2 library exhibited 1.66%, indicating the presence of higher affinity binders (FIG. 2A). Round two sort used 100 nM V-0025. The cycle 2 library showed 0.23% binding while the parent showed 0%; no binding was observed to a negative control (V-0018) (FIG. 2B). The third round of sorting used 10 nM V-0025, with 1.05% binding observed (FIG. 2C). The final round of sorting incorporated a Koff; briefly, V-0025 was incubated for 30 minutes at 100 nM, followed by incubation with R4c1 in full-length hIgG1 format (R4c1-IgG1). R4c1-IgG1 was added at 500 nM for various time points to act as an antibody sink. Thus, a final round of sorting was done using Koff pressure to select for top clones (FIG. 2D). To identify unique clones, individual colonies were picked and sequenced (n=48). Ten unique clones were identified (Table 2) and binding affinity was compared with the parent clone. Of the unique clones, six clones were shown to have at least 100-fold greater binding to V-0025 compared with the parent (FIG. 3A-FIG. 3D). One clone (clone R2A_1), in addition to having increased binding affinity, also exhibited superior selectivity and was selected for additional analysis (FIG. 3E-FIG. 3G).

TABLE 2

Unique clones and sequence modifications

| Index | Name | CDRH3 |
|---|---|---|
| 1 | parent | XXXXXXX |
| 2 | R2A_1 | XLXNXXX |
| 3 | R2A_3 | XHXTXXX |
| 4 | R2A_8 | XHXAXXX |
| 5 | R2B_1 | XHXNXXX |
| 6 | R2B_3 | XHXRXXX |
| 7 | R2B_8 | XHXWXXX |
| 8 | oR2A_1 | XYXTXXX |
| 9 | oR2A_2 | XVXXXXX |
| 10 | oR2A_3 | XLXSXXX |
| 11 | R3A2 | XHXVXXX |

Figure 4:
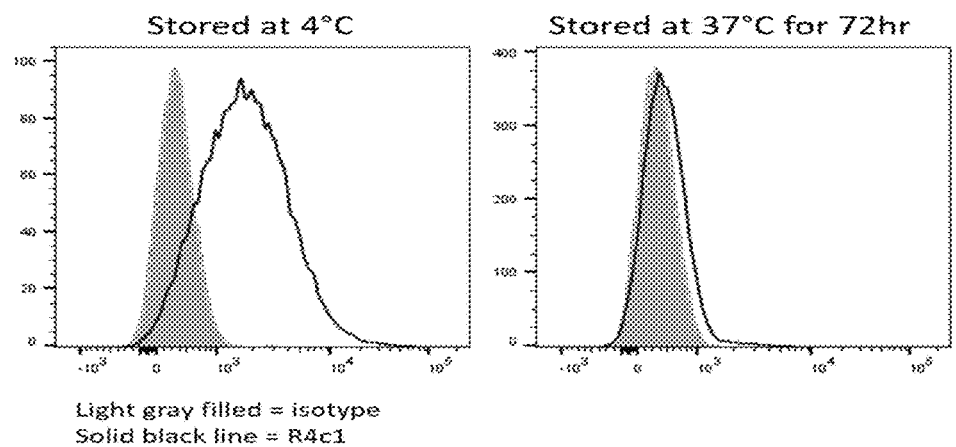
FIG. 4 exemplifies R2A_1 binding to A549-B4 cells.

Characterization of Clone R2A_1:

Clone R2A_1 was converted from scFv to full-length hIgG1 for testing by ELISA and for cell staining. Based on ELISA data, affinity was measured at about 20 nM (data not shown), which represents over 10-fold increase in affinity compared with the parent clone, R4c1. To check antibody stability, binding was compared after storing the antibody at 37° C. for 72 hr. As shown in FIG. 4 binding by R2A_1 to A549-B4 cells was heavily compromised when the antibody had been stored at 37° C. for 72 hr.

Stabilization of Clone R2A_1:

In order to increase the stability of R2A_1, several alterations were made to amino acids in the framework regions of both VH and VL. For the VL, the CDRL2 was modified to match its germline (IGKV1-39). This also removed an N-linked glycosylation site. For the VH, in framework region 1, Gln5 was changed to match germline (Leu5). Also in framework region 1, Met18 was changed to match germline (Leu18). The stabilized clone was referred to as R4c1 H1-L1. The scFv sequence was inserted into yeast for display and compared with the parent (R2A_1). While there was some loss in affinity, there was no alteration in specificity (data not shown).

Figure 5A:
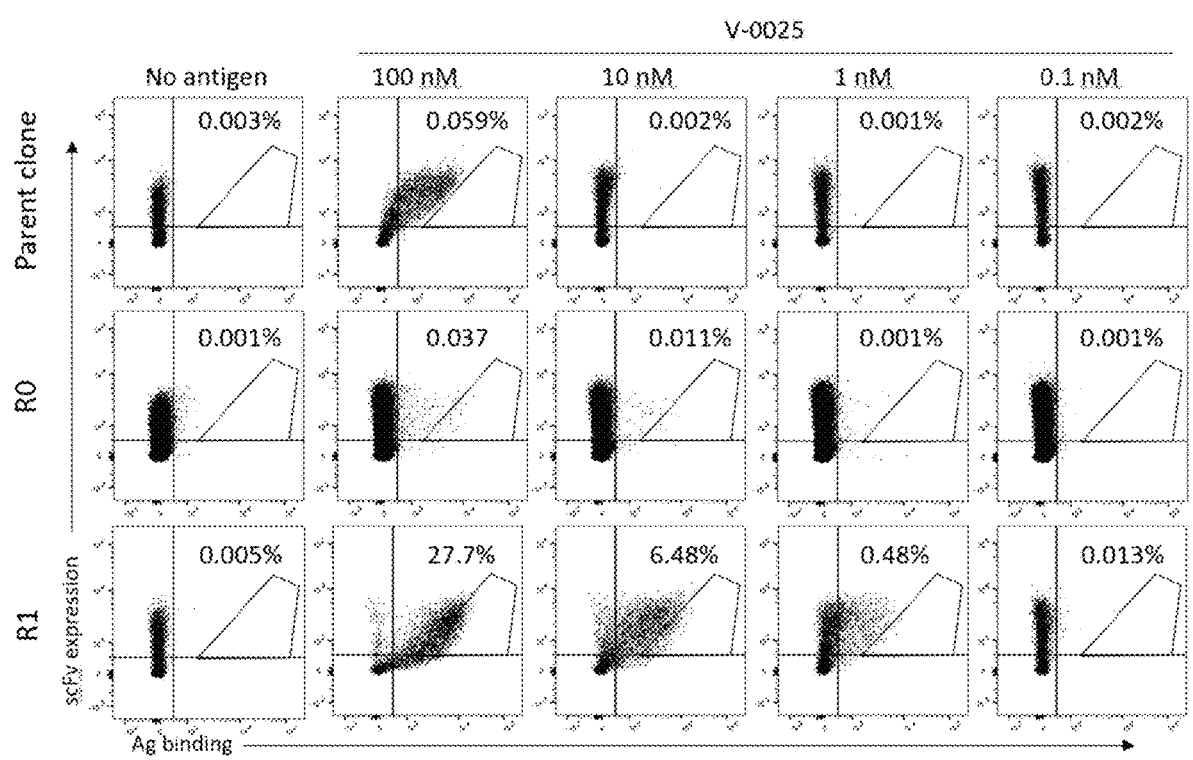
FIG. 5A-FIG. 5B exemplify isolation process for improved clones by affinity maturation of CDRL3 region of R2A_1.
Figure 5B:
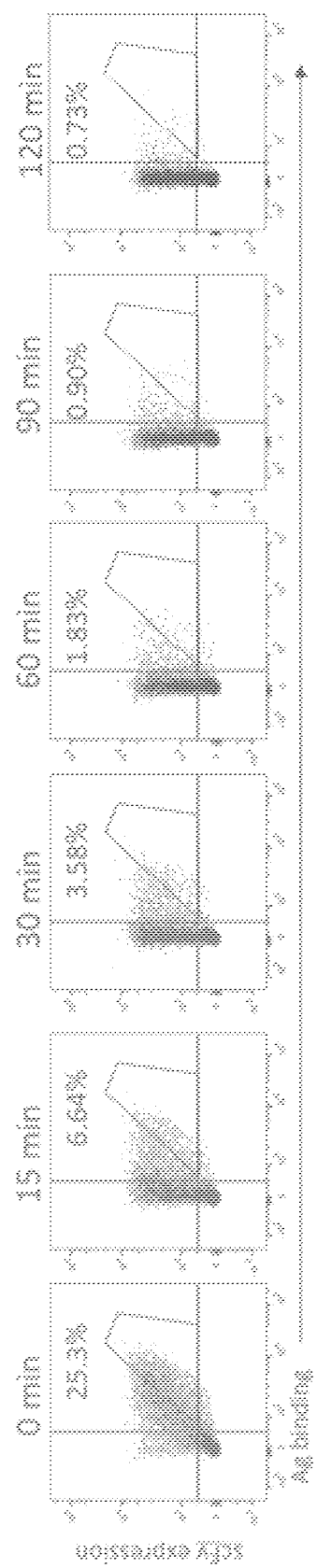
Figure 6A:
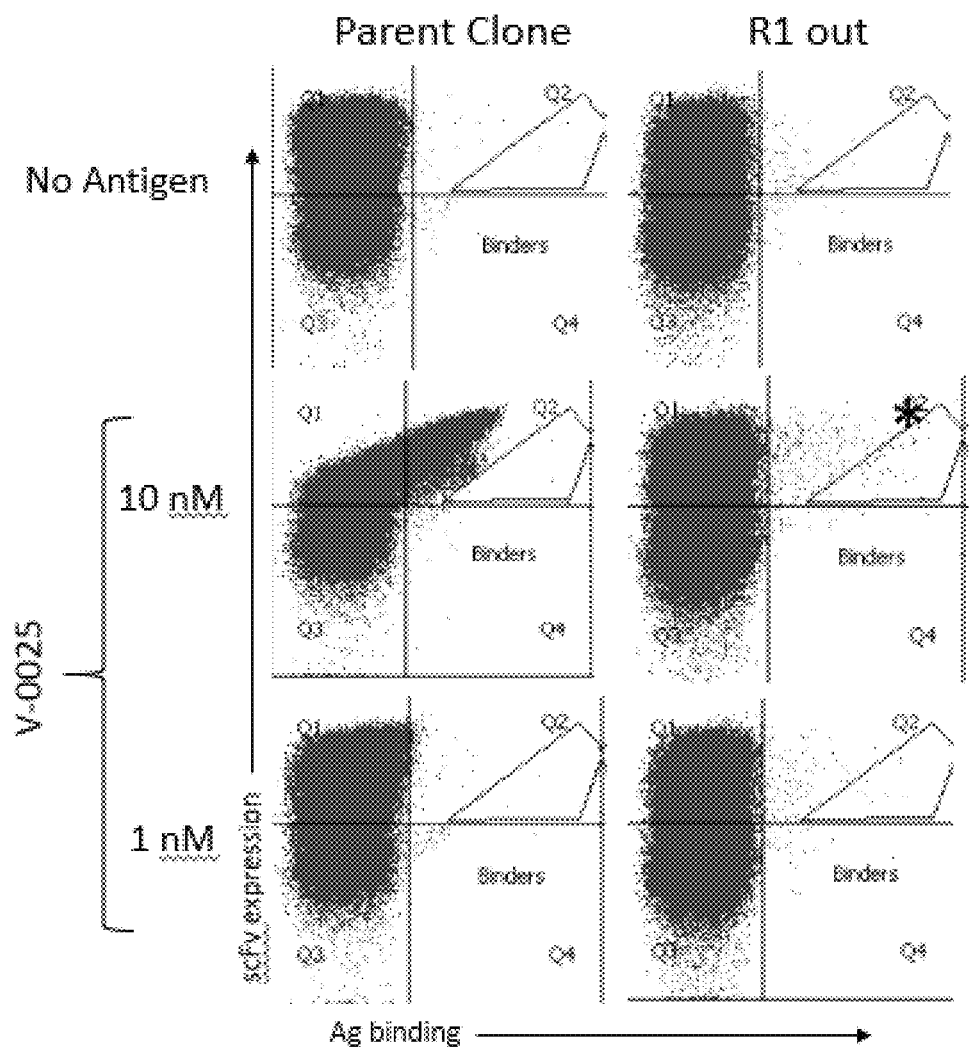
FIG. 6A-FIG. 6B exemplify the sorting schematic for the isolation of clones with greater binding affinity than the parent. Cell sorting plots showing (FIG. 6A) round 1 and (FIG. 6B) round 2 sorting for affinity maturation. The asterisk indicates the sorted population. For the R2 sort, Koff was utilized with V-0025 at 10 nM using R2A_1-IgG1 at 1 μM for 45 minutes as the antibody sink.
Figure 6B:
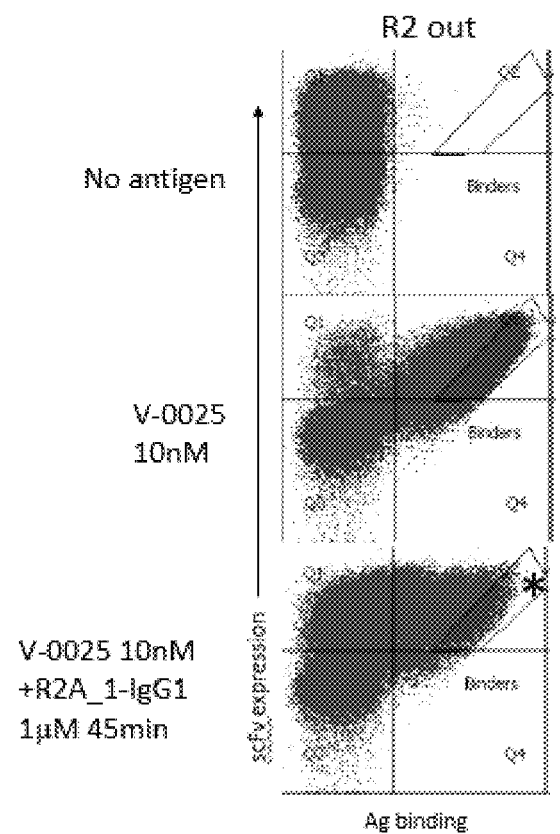
Figure 7:
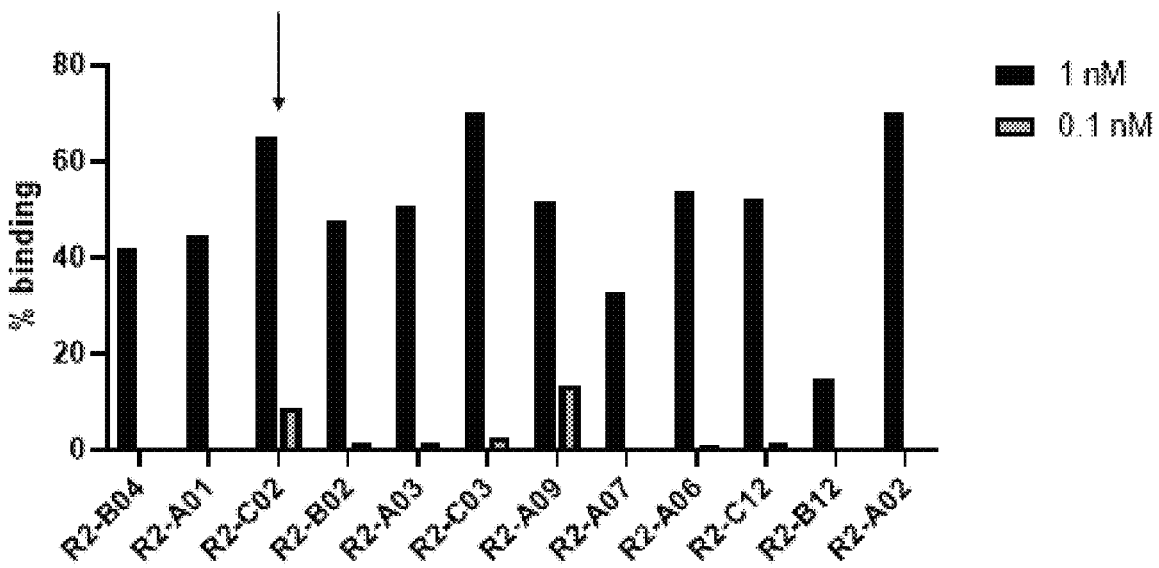
FIG. 7 exemplifies identification of clones from affinity maturation of the CDRL3 region of R2A_1 and binding profile to V-0025 at 1 nM and 0.1 nM. Arrow indicates the top clone.

To generate an antibody with greater affinity and broader specificity, a yeast display library was generated based off of R4c1-H1-L1 and introduced four amino acid mutations in the CDRL3 region, meaning that 44% of the CDRL3 sequence could potentially be altered from the parent. As shown in FIG. 5A (R0), very view clones exhibited binding to target, although there were a select group that had greater binding to target than parent. A sort was done (R1 out) using target at 10 nM with gating made to only select clones with greater binding affinity than the parent (FIG. 6A). The R1 library was checked for binding to target, and a substantial increase was observed in the number of clones binding with improved affinity compared with parent (FIG. 5A, R1). To select for clones with enhanced affinity, the R1 library was subjected to Koff pressure. Briefly, the library was incubated with 10 nM of target. After washing, 1 µM of the parent clone as a full length IgG1 was added for 15 to 120 minutes to act as an antibody sink. Any yeast still showing binding to target indicate a greater Koff compared with the parent clone. As shown in FIG. 5B, yeast clones were observed that maintained binding with target even after 120 minutes in the antibody sink To select for these highly improved clones, a final sort (R2 out) was done using Koff with target at 10 nM and parent clone-IgG1 at 1 µM for 45 minutes as the antibody sink, with sort gate made to collect only the clones with the highest affinity (FIG. 6B). After sorting, individual clones were isolated and sequenced (n=60). 12 unique clones were found (Table 3) and were checked for binding to target at 1 and 0.1 nM (FIG. 7). The top binding clone to target was selected for additional testing (clone R2-C02) (FIG. 7 black arrow).

TABLE 3

Unique clones

| Clone | CDRL3 | % occurrence |
|---|---|---|
| Parent | XXXXXXXXX | |
| R2-B04 | FXXXGXXXQ | 6.25 |
| R2-A01 | XCXXXXXGL | 6.25 |
| R2-C02 | XXXXAXXSL | 6.25 |
| R2-B02 | XXXXAXXSY | 6.25 |
| R2-A03 | XXXXCXXMF | 6.25 |
| R2-C03 | XXXXSXXQF | 6.25 |
| R2-A09 | XXXXSXXQW | 6.25 |
| R2-A07 | XXXXXFWEX | 12.5 |
| R2-A06 | XXXXXXFSP | 25 |
| R2-C12 | XXXXXXXCL | 6.25 |
| R2-B12 | XXXXXXXQF | 6.25 |
| R2-A02 | XXXXXXXSL | 6.25 |

Figure 8A:
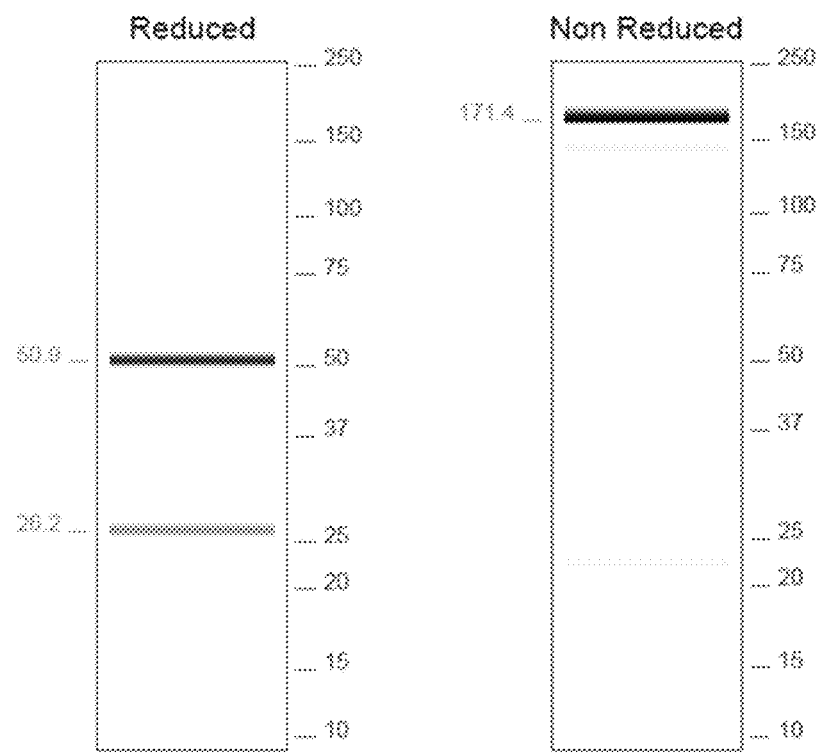
FIG. 8A-FIG. 8B exemplify QC data for the production of ABX0011.
Figure 8B:
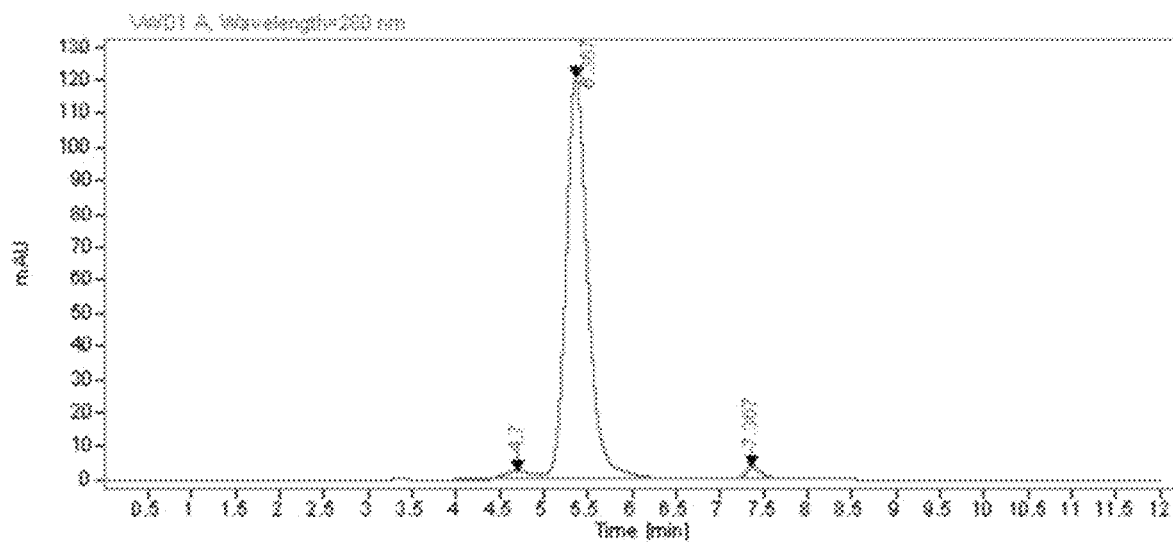
Figure 9A:
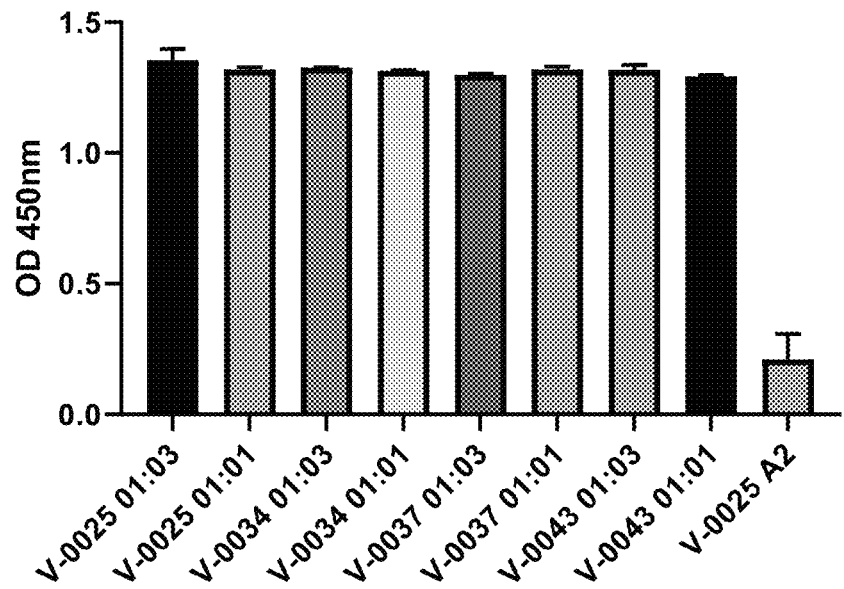
FIG. 9A-FIG. 9K exemplify binding specificity, affinity and stability of ABX0011. Specificity to antigen by ELISA (FIG. 9A) HLA-E (clone 3D12) and (FIG. 9B) ABX0011. For ELISA assays, antibodies were used at 1 mg/ml and HLA-E/peptide antigens were used at 0.5 mg/ml. Monovalent affinity of ABX0011 to target V-0025 was determined using ResoSens label-free instrument (Resonant Sensors, Inc. Arlington, Tex.) (FIG. 9C). The limit of detection for ABX0011 compared to clone 3D12 was assessed by ELISA (FIGS. 9D&E). ABX0011 and HLA-E were used at 1 μg/mL while V-0025 was titrated from 1 μg/mL down to 0.001 μg/mL (Fig. (D).
Figure 9B:
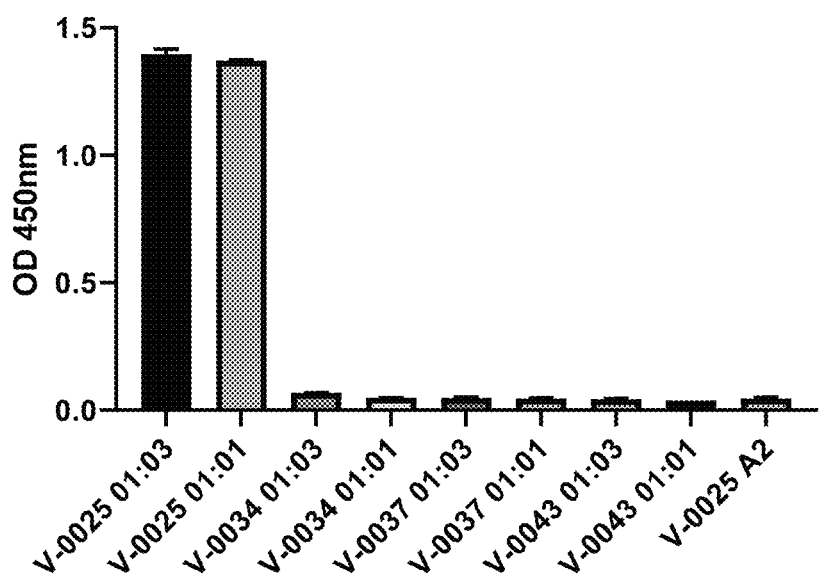

Example 2. Characterization of the Top Clone by ELISA, FACS and Label-Free Technology The top clone identified from yeast display was made as hIgG1 and tested for specificity and affinity. R2-C02 exhibited high affinity and the fine specificity (data not shown). R2-C02 was given the designation ABX0011 (or ABX-11) and produced in CHO cells using a 1-L transient transfection protocol followed by purification by Protein-A affinity chromatography. Sample purity was determined by SDS-PAGE reduced (two bands representing heavy and light chains) and non-reduced (single band at ~150 kD) (FIG. 8A) and by observing a single peak by size exclusion chromatography (FIG. 8B). ABX0011 was first tested against a broad array of peptide/HLA complexes. As shown in FIG. 9A, HLA-E clone 3D12 binds to all HLA-E complexes, including peptide-empty HLA-E. However, ABX0011 only recognized the non-classical HLA, HLA-G signal peptide/HLA-E complex and did not recognize closely related signal peptides from classical HLA (FIG. 9B). Furthermore, it did not recognize any additional peptide/HLA-E complexes, or any peptide/HLA-A2 complexes. For the ELISAs run, highly pure HLA-E 01:03 and HLA-A2 02:01 monomer complexes (diluted in 0.1% BSA, 0.1% Tween20, PBS dilution/wash buffer) were immobilized on neutravidin coated microarray plates at 0.25 ug/ml for one hour at RT. The plate was subsequently washed in dilution/wash buffer 5×. Antibodies diluted to 1 ug/ml in dilution/wash buffer were incubated for one hour at RT and plate was subsequently washed in dilution/wash buffer 5×. Anti-mouse and anti-human HRP conjugate was diluted 1:5000 in dilution/wash buffer and incubated for 30 minutes at RT then subsequently washed 5× in dilution/wash buffer. TMB substrate was added to plate wells and incubated for 15 minutes at 50 ul/well. 1N HCl stop solution was added at 50 µl/well before reading plate at 450 nm absorbance.

To determine whether ABX0011 recognized classical HLA I signal peptide presented by two different phenotypes of HLA-E, namely HLA-E 01:03 and HLA-E 01:01, monomer complexes of each were used in an ELISA as described above. No difference was observed between binding to the HLA-G signal peptide in the two HLA-E alleles; HLA-E*0101 and *0103 (FIG. 9B).

Figure 9C:
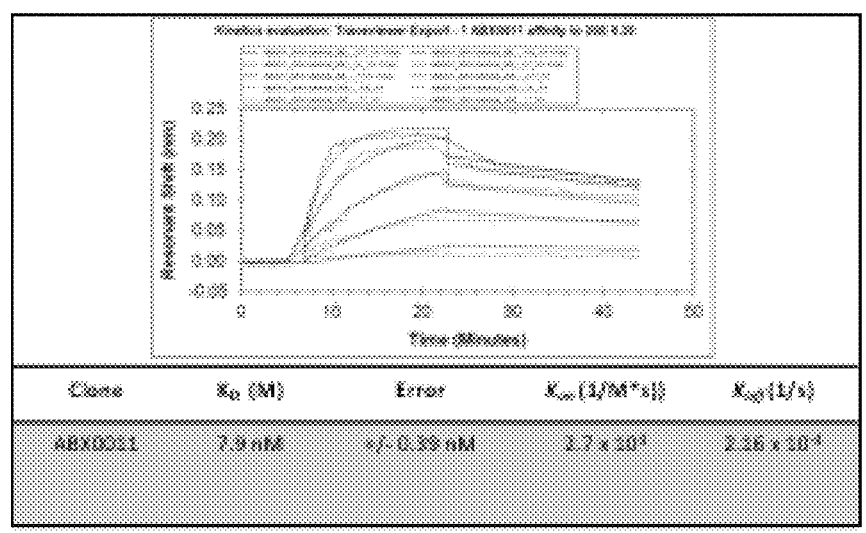

Affinity Determination for ABX0011:

The binding affinity of ABX0011 was determined using label-free technology (Resonant Sensors, Inc., ResoSens instrument). The dissociation equilibrium constant (KD) was found to be 7.9 nM or an improvement of more than 50-fold over the R4c1 clone (FIG. 1D, FIG. 9C). The method for determining the affinity was as follows. Thermofisher Capture Select™ Biotin anti-IgG-Fc (Hu) (diluted PBS buffer) was immobilized on neutravidin coated Bionetic label-free microarray plate at 5 µg/ml until binding reached equilibrium. Plate subsequently was washed 3× with 0.1% BSA, 0.1% Tween20, PBS dilution/wash buffer. ABX0011 (5 µg/ml in dilution/wash buffer) was captured by anti-IgG-Fc until binding reached equilibrium. Plate was subsequently washed in dilution/wash buffer 3×. V-0025 HLA-E 01:03 monomer complex (serial dilutions starting at 5 µg/ml in dilution/wash buffer) was added to wells and allowed to incubate for 20 minutes to determine the binding association and then immediately followed by dissociation (dilution/wash buffer) for approximately 25 minutes. Binding affinity calculated using Tracedrawer kinetic analysis software.

Figure 9D:
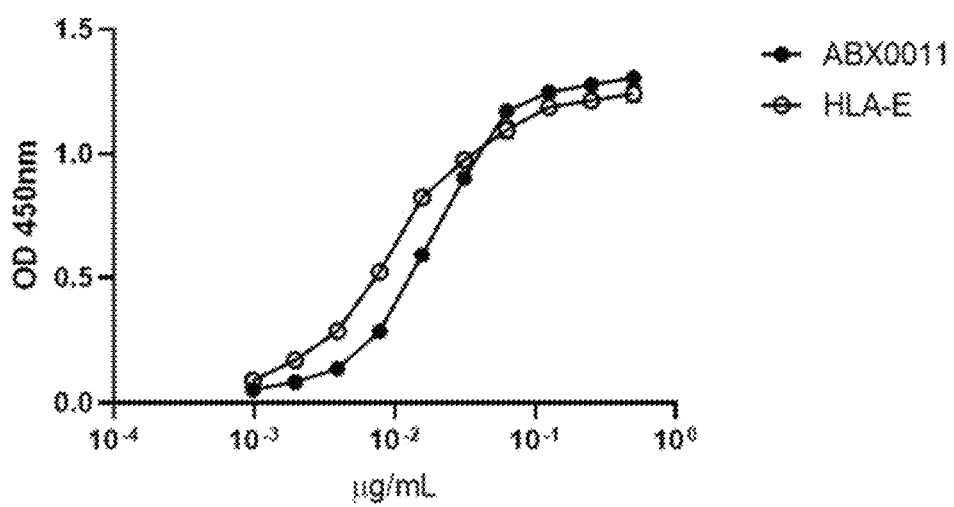
Figure 9E:
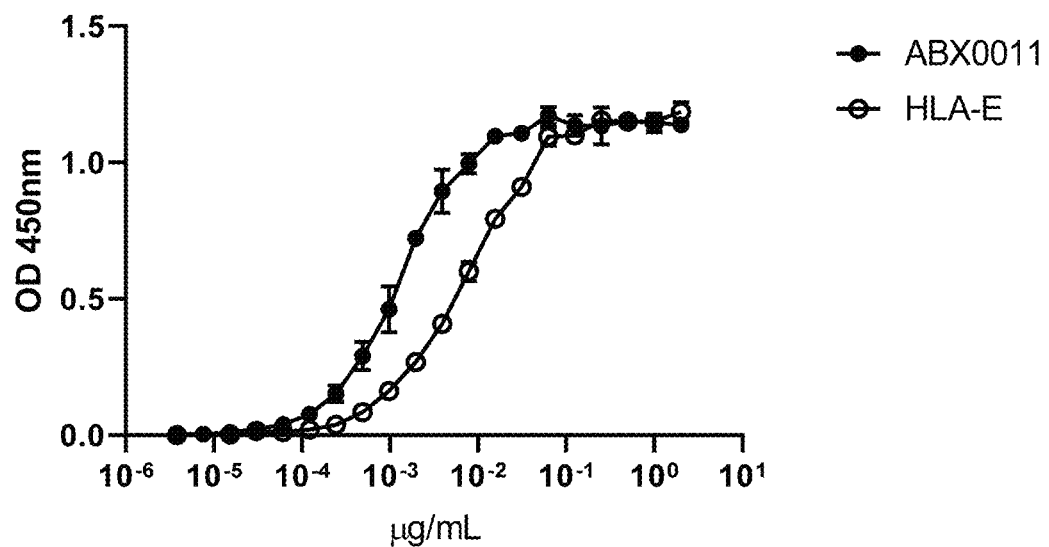
Figure 9F:
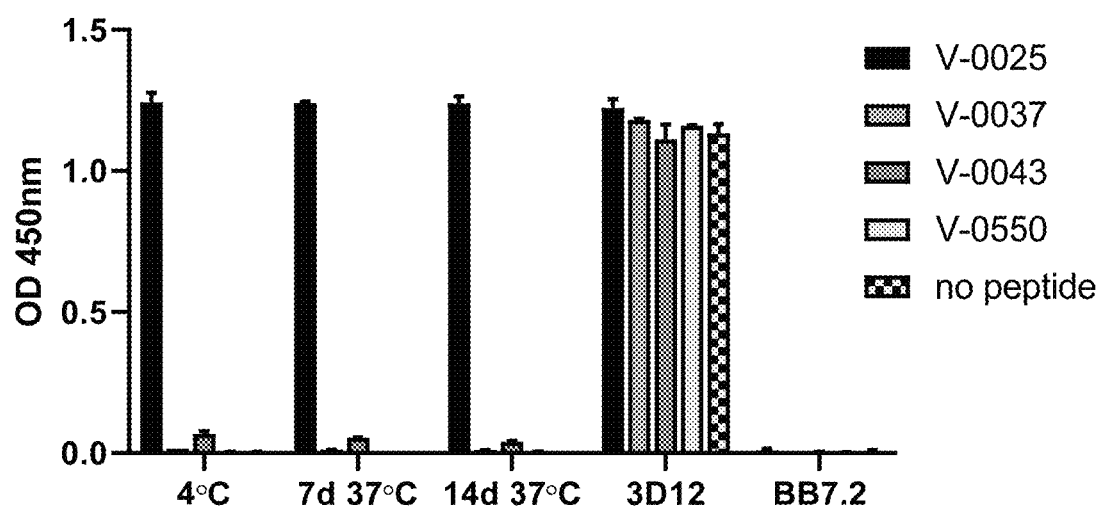

ABX0011 detection sensitivity could be observed by ELISA. In brief, V-0025 HLA-E 01:03 monomer complex (serial dilutions starting at 2 µg/ml in 0.1% BSA, 0.1% Tween20, PBS buffer) was immobilized on neutravidin coated microarray plate for one hour at RT. Plate was subsequently washed in dilution/wash buffer 5×. Antibodies were diluted to 1 µg/ml in dilution/wash buffer and incubated for one hour at RT and subsequently washed in dilution/wash buffer 5×. Anti-mouse and anti-human HRP conjugate was diluted 1:5000 in dilution/wash buffer and incubated for 30 minutes at RT and then subsequently washed 5× in dilution/wash buffer. TMB substrate incubated for 15 minutes at 50 ul/well. 1N HCl stop solution added at 50 µl/well and plate is read at 450 nm. In FIG. 9D, ABX0011 and HLA-E were bound at 1 µg/mL and tested against a titration of the antigen V-0025. Similarly, in FIG. 9E, V-0025 was bound at 0.25 µg/mL and tested against a titration of ABX0011 and HLA-E using a similar ELISA protocol as described for FIG. 9A. To check stability, ABX0011 was left at 37° C. for 7 to 14 days, then checked against ABX0011 stored at 4° C. ABX0011 was diluted to 1 µg/ml in mouse serum incubated at 37° C. for 7 and 14 days (4° C. control was prepared in serum at time of testing) and added to wells with immobilized HLA-E 01:03 monomer complexes and run in an ELISA as described above. As shown in FIG. 9F, binding was not altered, indicating good stability of ABX0011.

Figure 9G:
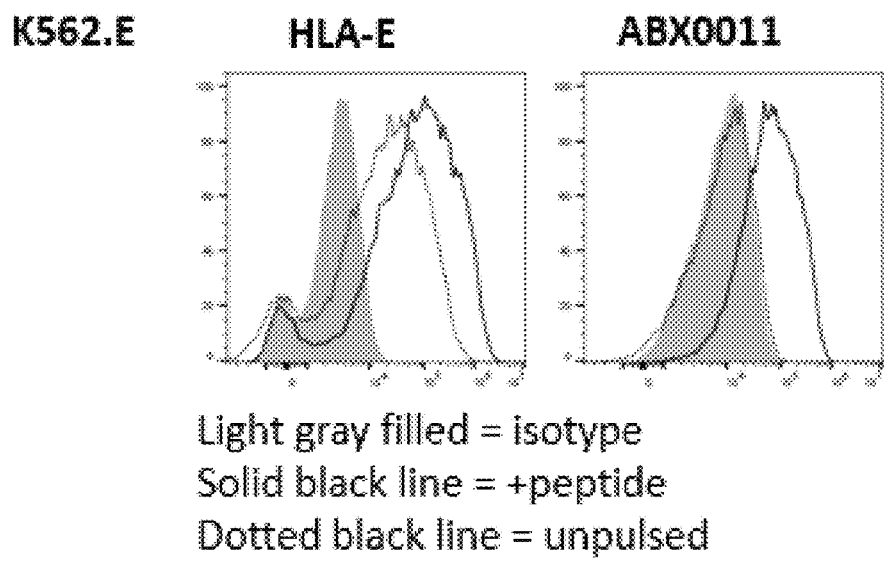
Figure 9H:
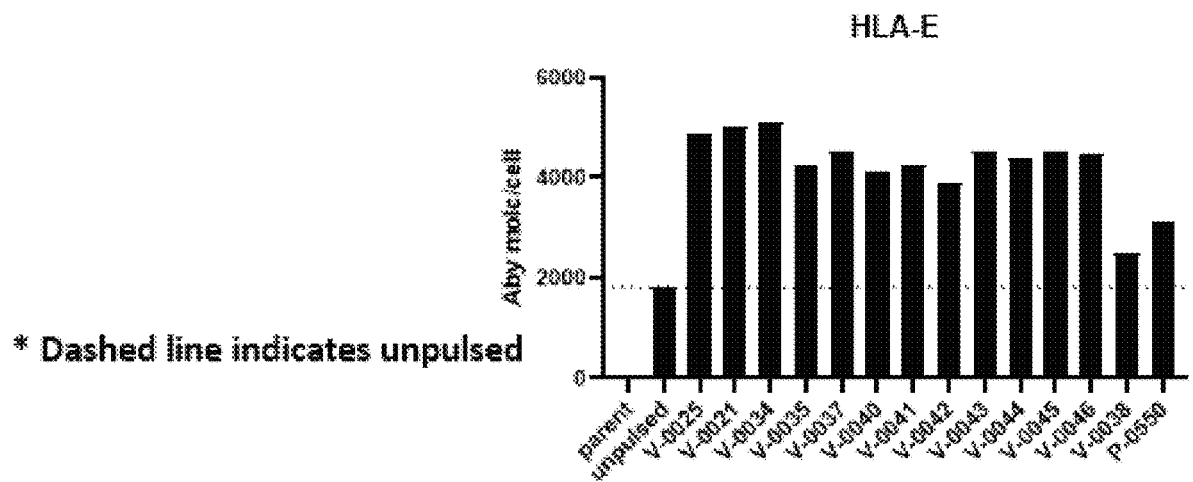
Figure 9I:
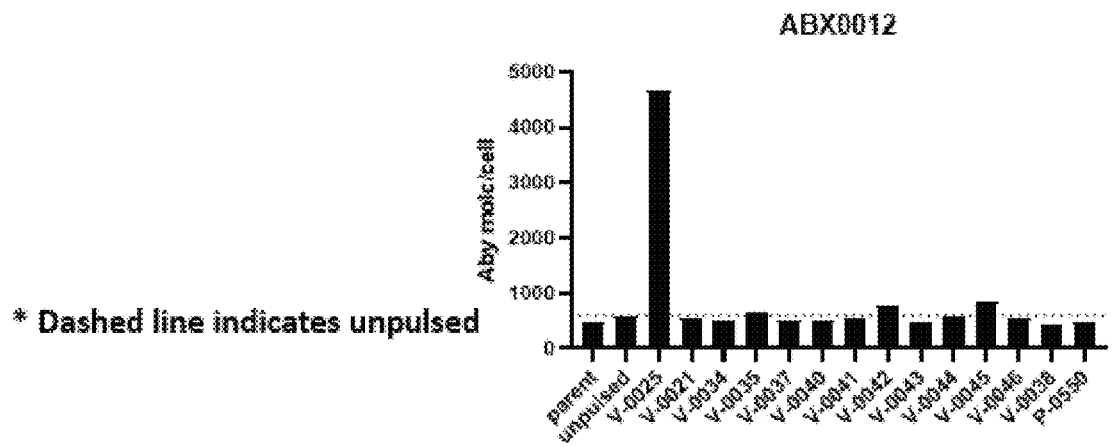
Figure 9J:
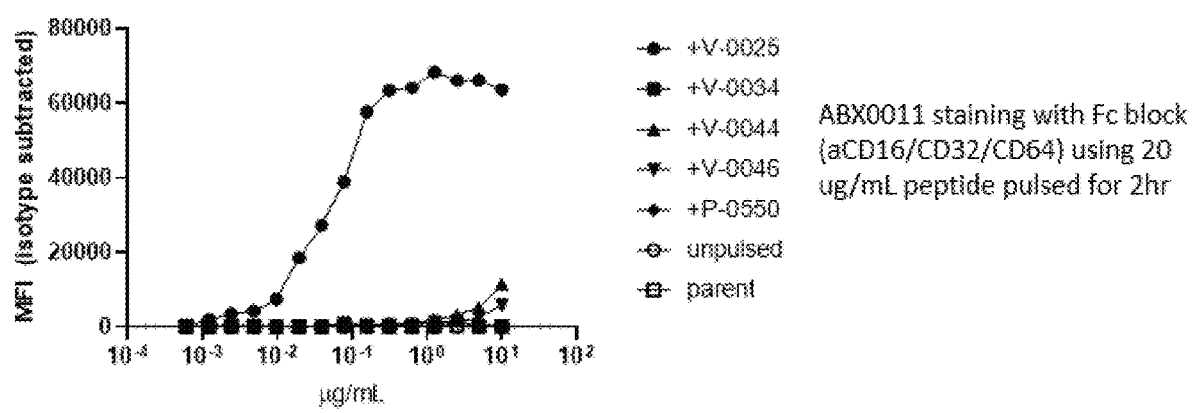

To further characterize specificity, K562 cells transfected to express HLA-E were first peptide-pulsed with the V-0025 peptide, then tested for binding to HLA-E and ABX0011. As shown in FIG. 9G, V-0025 peptide pulsed cells showed loading, based on an increase in HLA-E expression compared with no peptide (unpulsed). ABX0011 showed specificity for HLA-G loaded on HLA-E, with no binding to unpulsed cells (FIG. 9G). K562 cells transfected to express HLA-E were next pulsed with all of the classical HLA signal peptides, the non-classical HLA signal peptide, and two other HLA-E binding peptides namely, V-0038 and P-0550. All peptide pulsed cells showed loading, based on an increase in HLA-E expression compared with no peptide (unpulsed) (FIG. 9H). Again, ABX0011 (as exemplified by ABX0012) recognized only the V-0025 peptide in K562 cells expressing HLA-E (FIG. 9I). Background staining was approximately 500 antibody molecules/cell. To further assess the fine binding specificity of ABX0011, K562 cells expressing HLA-E were peptide pulsed with 20 µg/ml of either V-0025, V-0034, V-0044, V-0046, P-0550 or left unpulsed and then stained with ABX0011 at various concentrations ranging from 10 to <0.001 µg/ml. Again, ABX0011 showed selectivity only for the V-0025 peptide with only minimal detection of two closely related peptides, V-0044 and V-0046 when used at a concentration of 10 ug/ml (FIG. 9J).

Figure 9K:
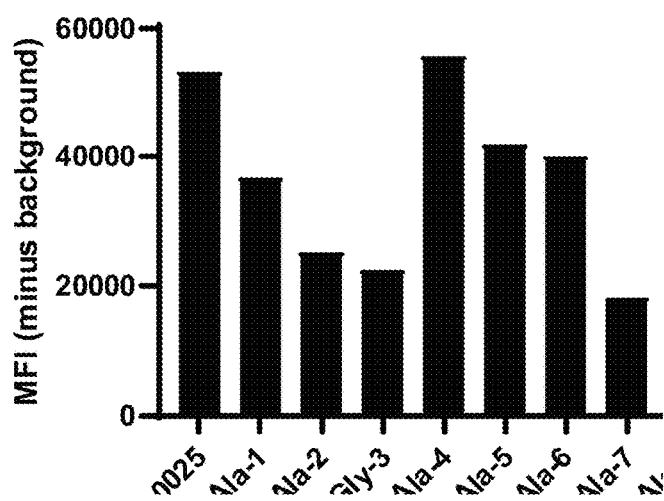

An alanine scan based on the peptide sequence for V-0025 (HLA-G signal peptide) indicated that the binding of ABX0011 to peptide/HLA-E complex is mainly dependent on the amino acid at position 8 with less dependence though still critical contact at amino acid positions 2, 7 and 9 (FIG. 9K). Overall, these results indicate that ABX0011 exhibits selectivity to non-classical HLA-G peptide signal sequence, with high affinity and stability.

Example 3. ABX0011 Binds with Selectivity to Target Positive Cancer Cell Lines

Figure 10A:
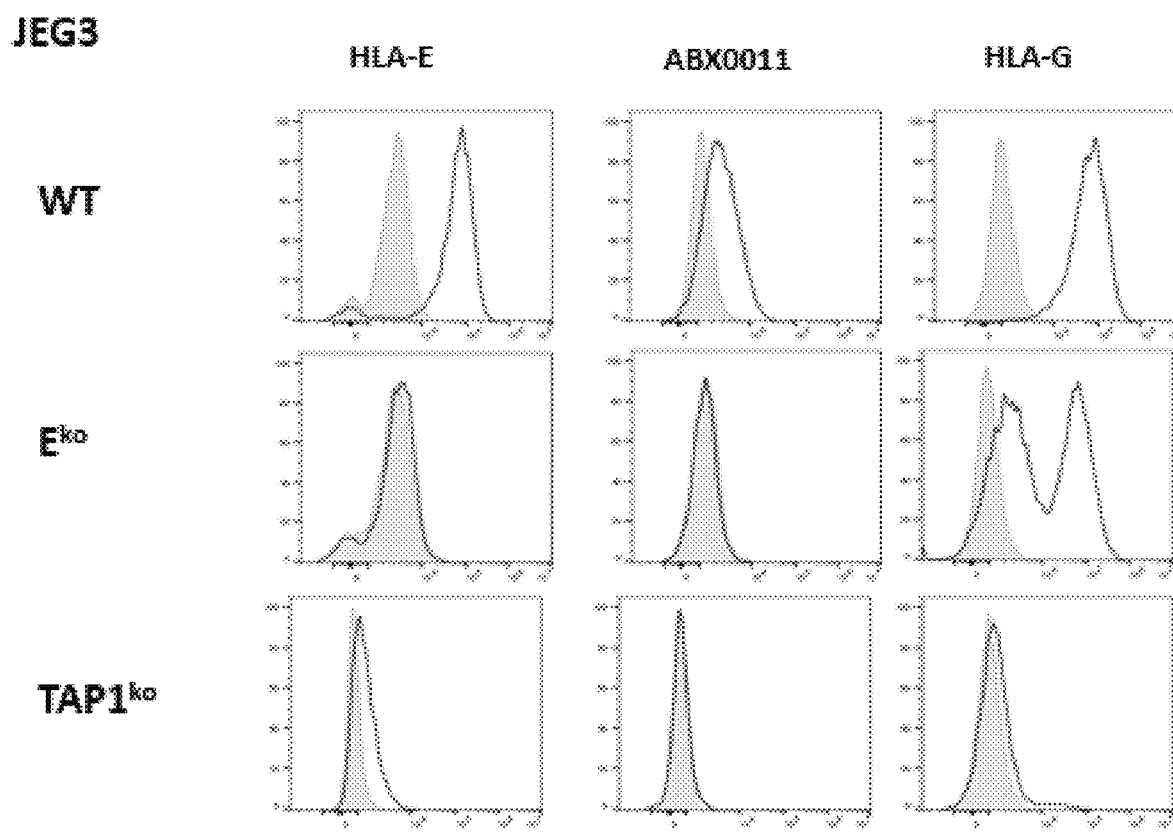
FIG. 10A-FIG. 10C exemplify ABX0011 binding specificity to a cell line that expresses HLA-E and HLA-G (FIG. 10A) and no binding was observed to human peripheral blood mononuclear cells (huPBMC) and primary human umbilical vascular endothelial cells (huVEC) lacking HLA-G (FIG. 10B and FIG. 10C). Antibody binding studies were performed at 1 μg/mL.
Figure 10B:
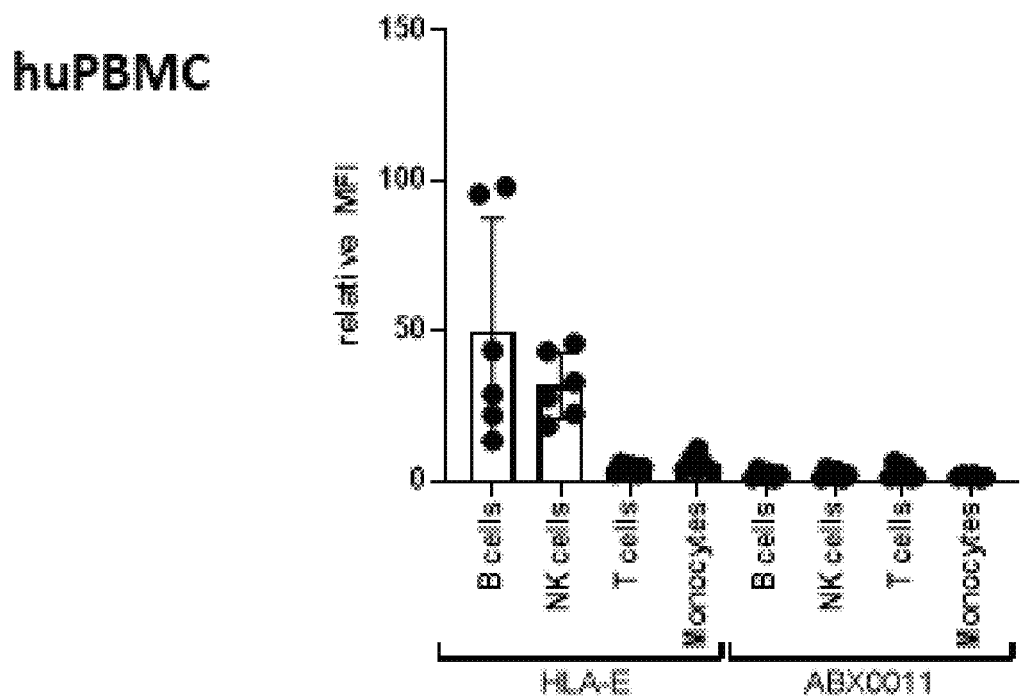
Figure 10C:
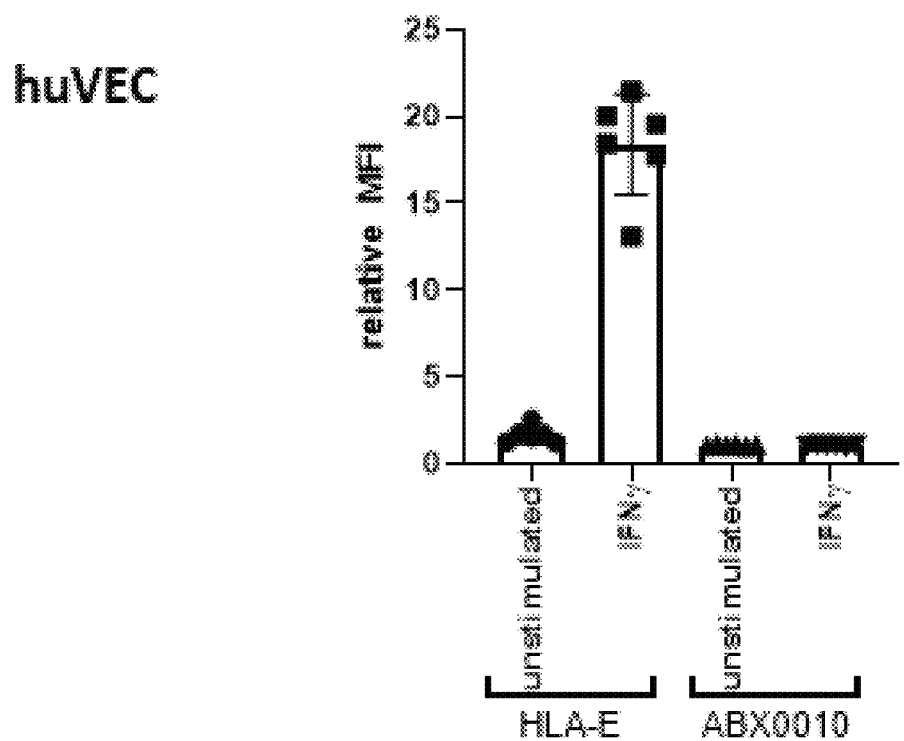

To confirm specificity, binding of ABX0011 was tested in a variety of tumor cell lines, human peripheral blood mononuclear cells (huPBMC) and primary human umbilical vascular endothelial cells (huVEC). Since HLA-E is known to be highly expressed in normal placenta trophoblasts, the choriocarcinoma trophoblastic cell line JEG-3 was used as a positive control for binding by both HLA-E and ABX0011 (FIG. 10A). To confirm the restriction of ABX0011 to HLA-E/peptide complexes, binding was tested in HLA-E-deficient JEG-3 (JEG-3 Eko). As shown in FIG. 10A, middle panel, HLA-E and ABX0011 were unable to bind to JEG-3 Eko cells. To confirm that the HLA-G signal peptide is dependent on Tap1/2 expression, ABX0011 was used to stain Tap-1 knock-out JEG3 cells (JEG-3 Tap-1ko). As shown in FIG. 10A, lower panel, there is still some expression of HLA-E without Tap-1, however, ABX0011 exhibits no binding, indicating that it only recognizes the HLA-G signal peptide processed via the conventional pathway. Specificity was similarly shown using huPBMC and huVEC cells. Human PBMCs, in particular B-cells and NK cells express high levels of HLA-E (FIG. 10B). In contrast, healthy huPBMC do not express HLA-G and therefore huPBMC lack binding with ABX0011 (FIG. 10B). Additionally, huVEC after O/N treatment with IFN-γ express high levels of HLA-E. However, ABX0011 (as exemplified by ABX0010) does not bind to huVECs in the absence or presence of IFN-γ treatment (FIG. 10C).

Figure 11A:
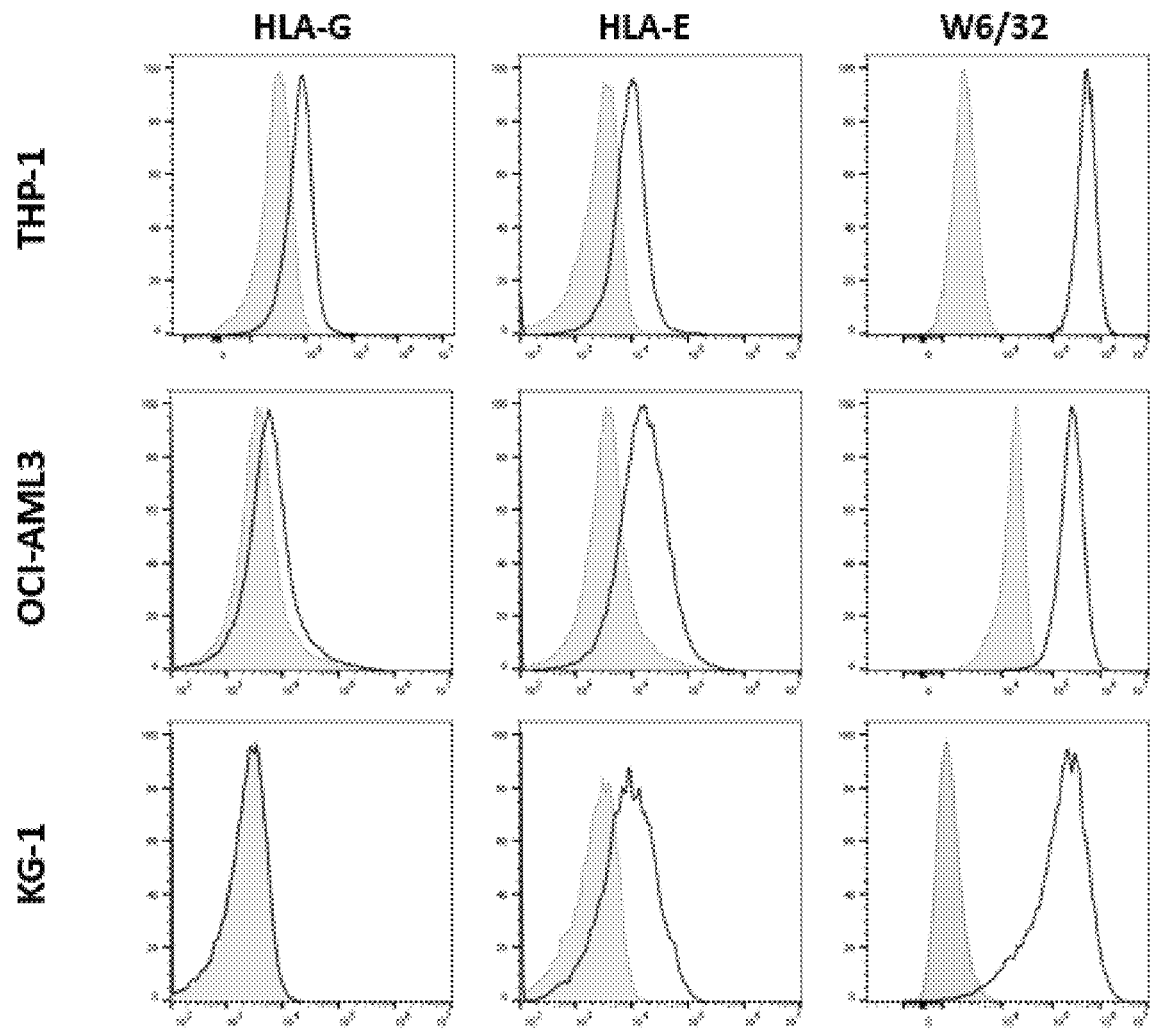
FIG. 11A-FIG. 11B exemplify binding to AML cell lines that express both HLA-E and HLA-G (THP-1 and OCI-AML3) or only express HLA-E (KG-1). AML cells stained at 1 μg/ml of antibody using 3D12 (HLA-E), MEM-G/09 (HLA-G) and W632 (pan HLA I) (FIG. 11A). ABX0012 (ABX0011 with mouse IgG1) was titrated (10 to 0.004 mg/ml) and binding to target positive AML cell lines was observed (FIG. 11B).
Figure 11B:
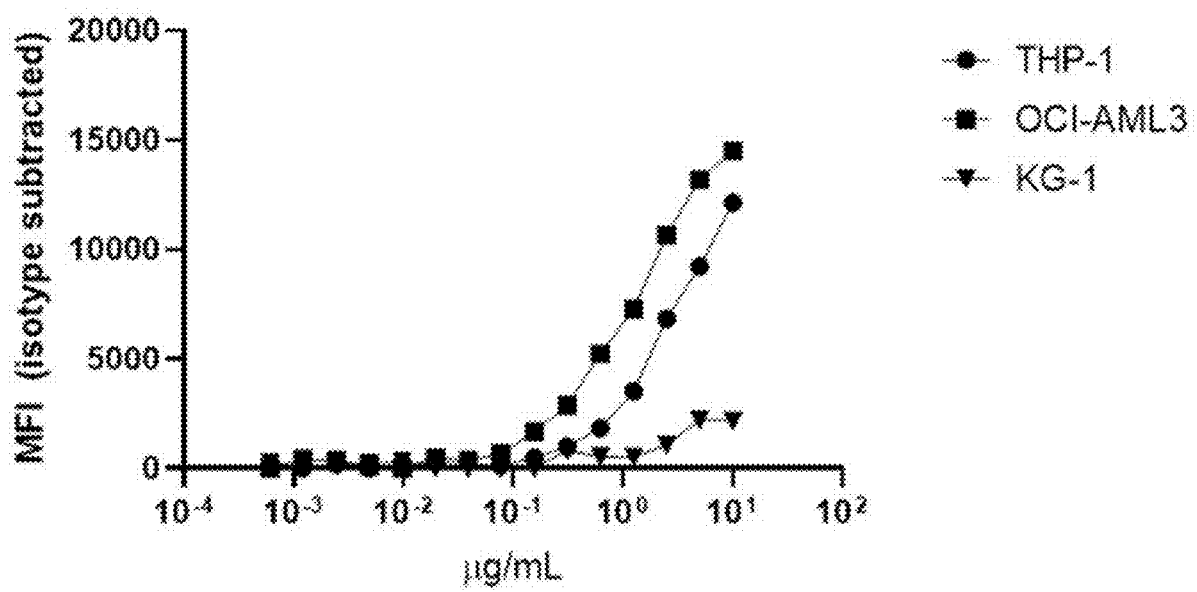

HLA-E is known to be increased in multiple types of cancers. Therefore, several cancer cell lines were analyzed for HLA-E expression and ABX0011 binding. Since HLA-E is upregulated when cells are stressed or stimulated, binding was observed in both unstimulated and IFNγ-stimulated cells. FIG. 11A illustrates two cell lines (THP-1 and OCI-AML3) that express HLA-E and HLA-G and bind ABX0011 without stimulation, and one cell line (KG-1) that express HLA-E and not HLA-G and do not bind ABX0011. Further, binding to AML cell lines with ABX0011 (as exemplified by ABX-0012) using a range of concentrations (10 to <0.001 µg/ml) revealed good selectivity for ABX0011 (FIG. 11B). These results indicate that ABX0011 may be used to target AML cancers as well as other cancers that express both HLA-E and HLA-G. K562 cells expressing HLA-E and mutated JEG3 cells were acquired from (Thorbald van Hall; Leiden University Medical Center). In some instances, cells required stimulation overnight with IFNγ (10 ng/ml) to induce HLA-E expression.

For all cell binding studies (with exception ABX0012, the ABX0011 with mouse IgG1), cells were blocked with anti-human CD16 (clone KD1), anti-human CD32 (clone AT10), and anti-human CD64 (clone 10.1) (Bio-Rad) or with Human TruStain FcX (BioLegend) at room temperature for 5-10 min before surface staining with ABX0011 or hIgG1 (clone QA16A12, BioLegend) at 1 µg/mL or with AF647-labeled ABX0011 or hIgG1, and with HLA-E in PE or PE-Cy7 (clone 3D12, BioLegend) at 4° C. for 30 min in 100 µL. Cells were then washed with staining buffer (PBS with 2 mM EDTA) followed by secondary staining cocktail including Goat-anti-human/AF647 (Jackson ImmunoResearch) and zombie/aqua viability stain (BioLegend). Cells were incubated at 4° C. for 30 min in 100 μL. Cells were washed twice with staining buffer and fixed using fluorofix (BioLegend). Samples were acquired using an LSR II flow cytometer (BD Biosciences) or a CytoFLEX S (Beckmen Coulter). Data was prepared using Flowjo Software version 10 (BD Biosciences).

Example 4. ABX0011 Induces NK Mediated Antibody-Dependent Cellular Cytotoxicity (ADCC) of Target Cells The primary objective of these studies was to determine the ability of ABX0011 and to induce NK cell mediated ADCC of target cells. To test the ability of ABX0011 to induce ADCC, primary human NK cells were co-cultured with various tumor target cells in the presence of ABX0011. Blood from healthy volunteers was acquired from Carter BloodCare. PBMCs were isolated by density-gradient centrifugation using Ficoll-Paque PLUS (GE Healthcare) or Lymphoprep (StemCell Technologies). Natural Killer (NK) cells were purified using EasySep human NK cell enrichment kit (StemCell Technologies).

Figure 12A:
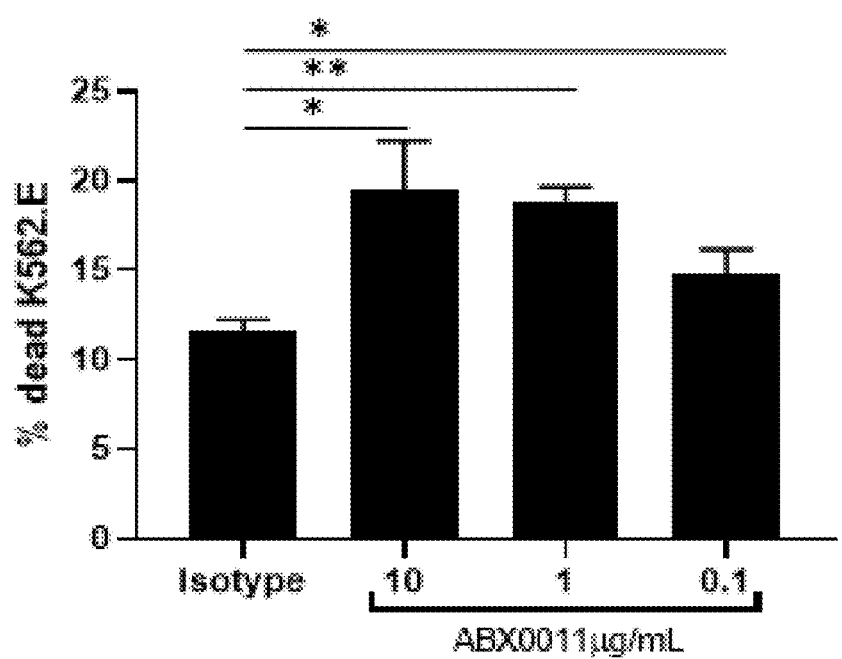
FIG. 12A-FIG. 12D exemplify ABX0011 mediated NK cytotoxicity against tumor cell lines expressing target. NK cells were co-cultured with V-0025 peptide-pulsed K562.E cells or with THP-1 cells with an isotype control (hIgG1). The frequency of CD107a-positive NK cells and CD107a-positive NKG2A+ NK cells are shown (FIG. 12 A and FIG. 12B). The frequency of dead target cells (K562.E) and THP-1 cells is shown in FIG. 12C and FIG. 12D, respectively.
Figure 12B:
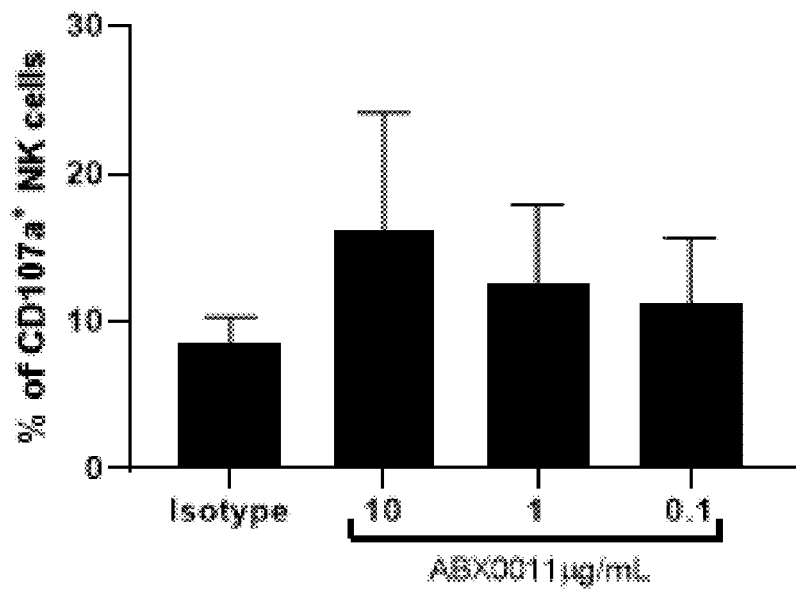
Figure 12C:
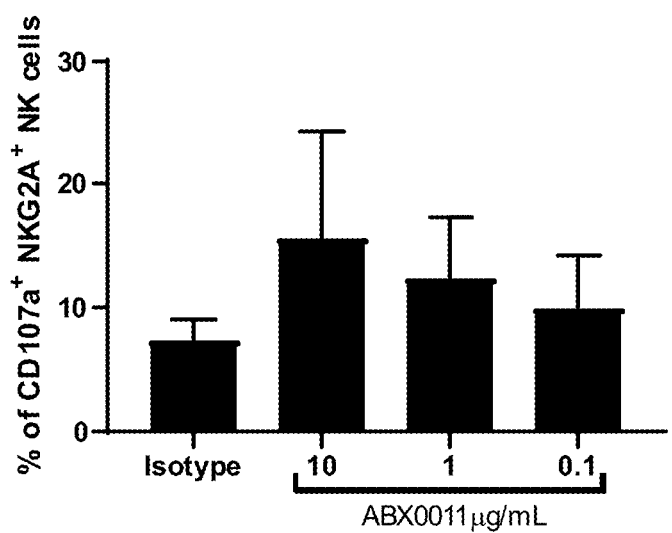
Figure 12D:
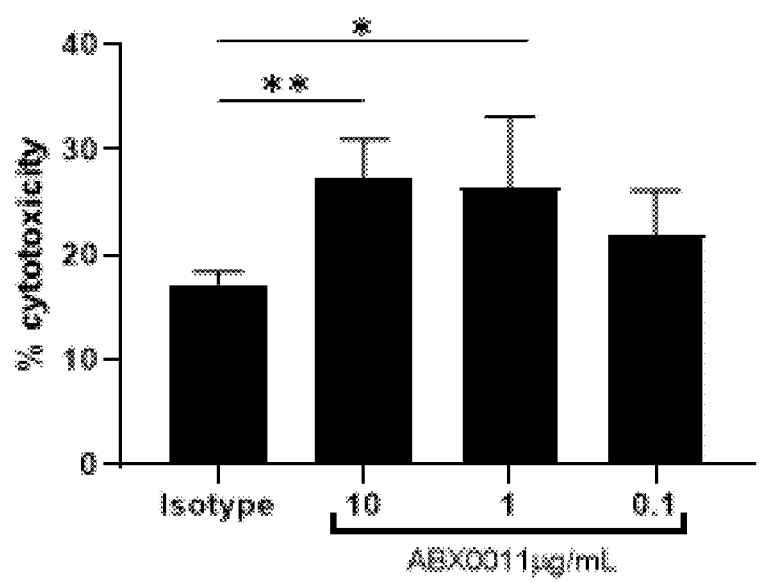

As shown in FIG. 12A, after four-hour co-culture of NK cells with peptide-pulsed K562.E cells, ABX0011 was able to significantly increase killing of K562.E cells in a dose-dependent manner compared to isotype control (FIG. 12A) and upregulate NK CD107a expression (FIG. 12B) and more specifically induce an increase of CD107a expression on NKG2A+ NK cells (FIG. 12C). Similar results were also found when using THP-1 cells (FIG. 12D). These results indicate that ABX0011 can be used to promote tumor cytotoxicity by inducing NK cell ADCC activity.

Figure 13A:
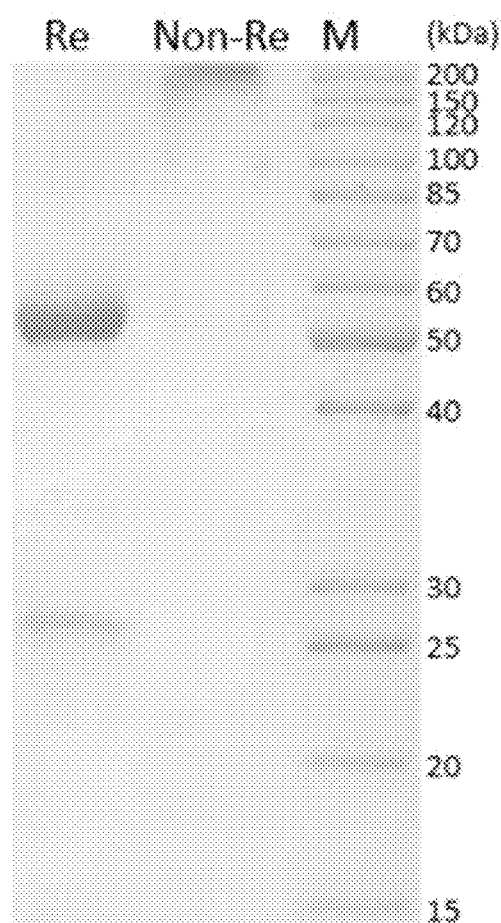
FIG. 13A-FIG. 13B exemplify QC data for the production of ABX0030, a bispecific T cell engager that contains the VL and VH domains of ABX0011 linked covalently to an anti-CD3 scFv fragment.
Figure 13B:
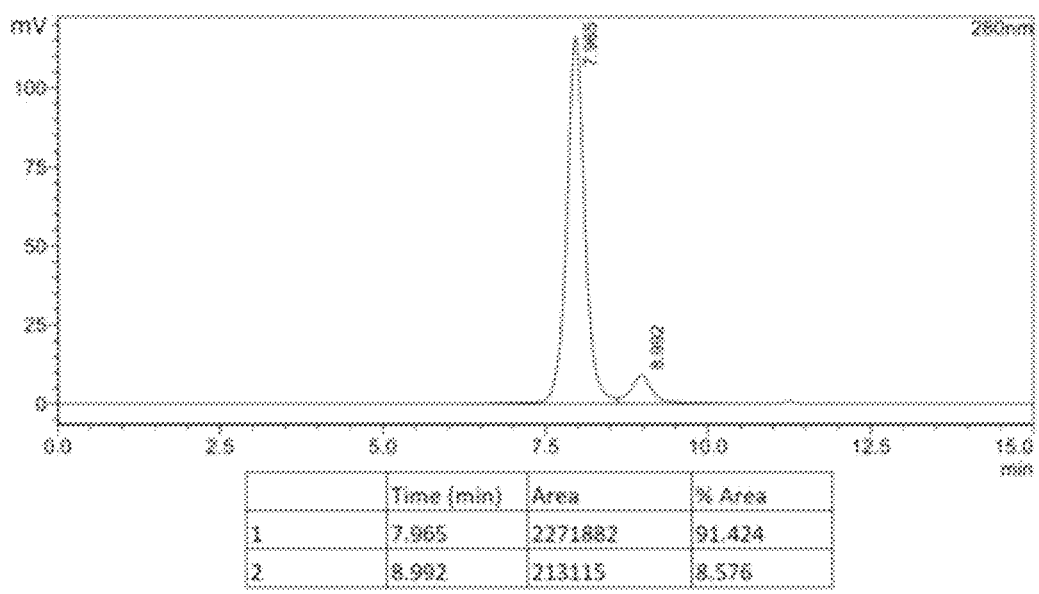

Example 5. Creating a Bispecific Antibody Capable of Retargeting T-Cells to Lyse Tumor Target Cells ABX0030 was constructed as a bispecific antibody to be able to activate CD3+ T-cells to kill tumor cells. ABX0030 was made as an Fab-Fc-scFv construct containing ABX0011 (Fab) coupled to a single-chain (scFv) of clone SP34 (mouse anti-human CD3e) on an non-glycosylated (N297D mutation) human IgG1 scaffold. A_20 amino acid linker (GKPGSGKPGSGKPGSGKPGS (SEQ ID NO: 20)) was used to covalently join the ABX0011 Fab with the SP34 scFv. ABX0030 was produced in a transiently transfected CHO cell and purified on a Protein-A affinity column. ABX0030 was run on a reducing SDS-PAGE gel and shows the expected two bands at the anticipated MW (25 kD for the ABX0011 light chain and ~55 kD for ABX0030 without light chain) (FIG. 13A). Greater than 91% of ABX0030 migrates as a single peak on an analytical SEC-HPLC column (FIG. 13B).

Figure 14:
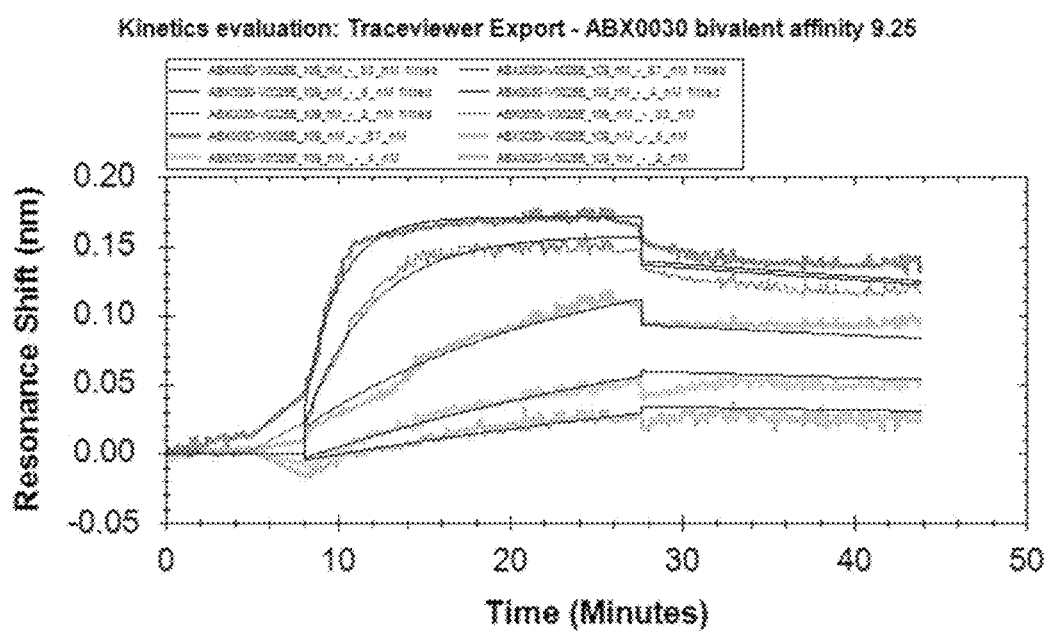
FIG. 14 exemplifies affinity analysis for ABX0030.

The binding affinity of ABX0030 was determined using a label-free assay (ResoSens instrument, Resonant Sensors, Inc). Briefly, V-0025 HLA-E 01:03 monomer complex (diluted in 0.1% BSA, 0.1% Tween20, PBS buffer) was immobilized on neutravidin coated Bionetic label-free microarray plate at 5 μg/ml until binding reached equilibrium. Plate was subsequently washed in dilution/wash buffer 3x. The ABX0030 (serial dilutions starting at 10 μg/ml in dilution/wash buffer) binding association was evaluated for approximately 20 minutes and immediately followed by dissociation (dilution/wash buffer) for approximately 15 minutes. Binding affinity calculated using Tracedrawer kinetic analysis software. The findings revealed a dissociation equilibrium constant of 8.97 nM (FIG. 14).

Figure 15:
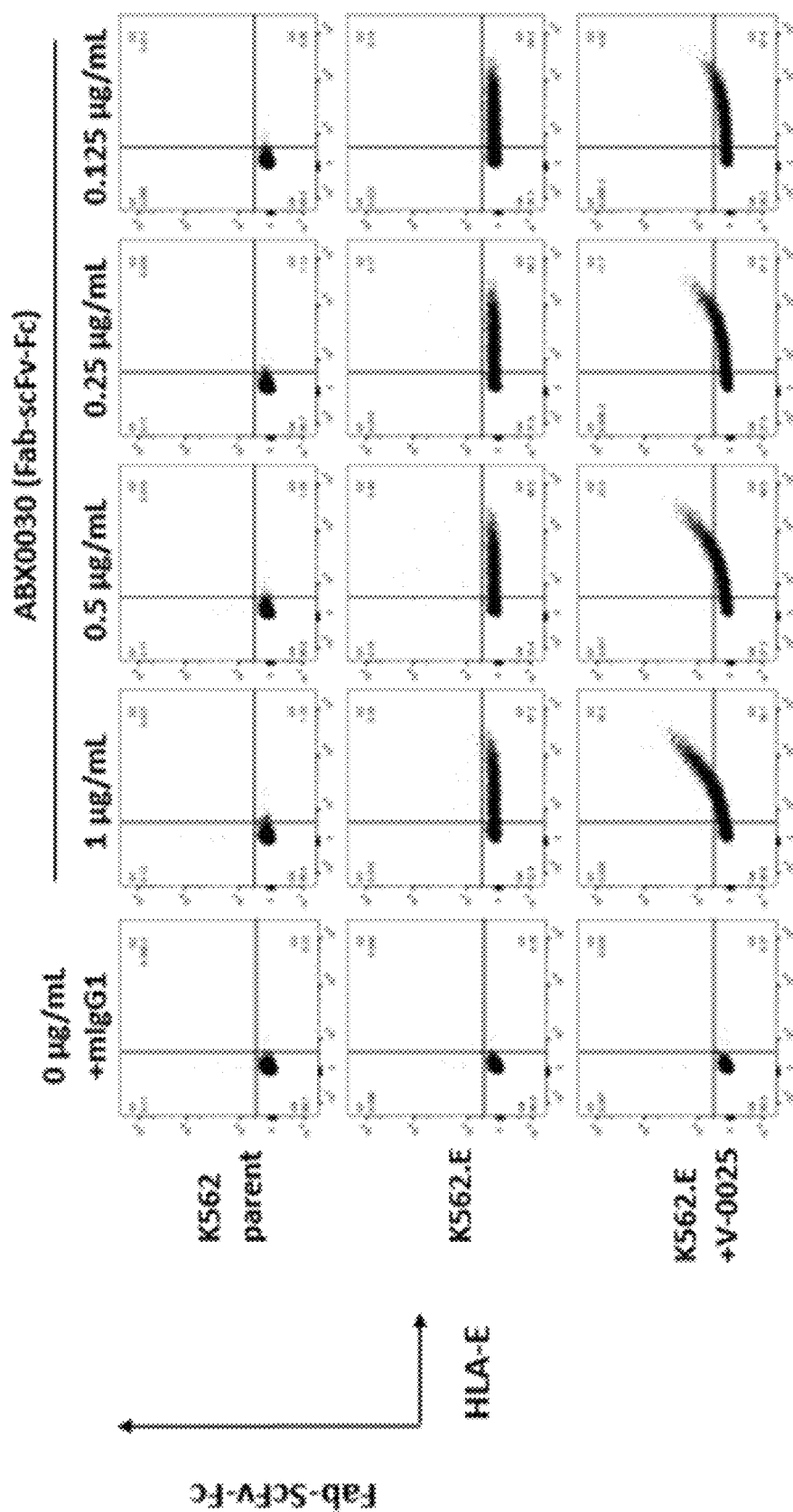
FIG. 15 exemplifies that ABX0030 binding to K562.E cells is peptide specific. Only K562.E cells pulsed with V-0025 target peptide were stained with ABX0030 in a dose dependent manner. Control cells, parent K562 and K562.E without peptide were not stained with ABX0030.
Figure 16:
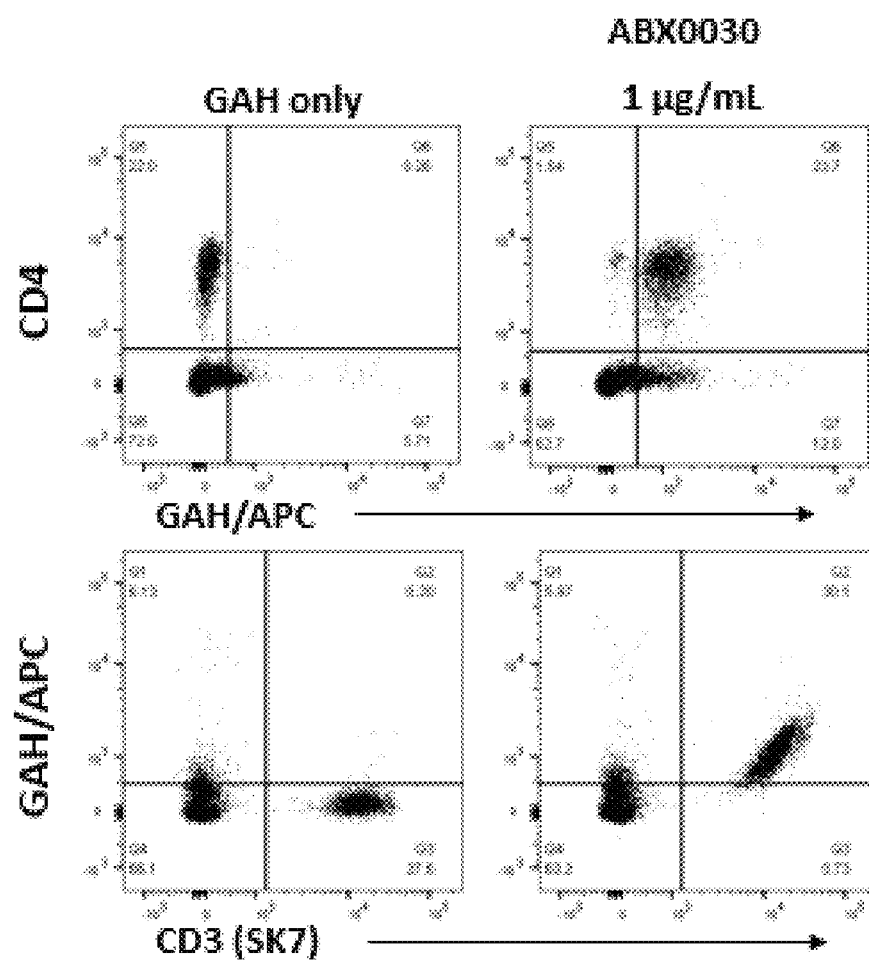
FIG. 16 are exemplary histograms to illustrate that ABX0030 stains human CD3+ cells and not CD3neg cells. PBMCs stained with GAH-APC conjugate and anti-CD3 (clone SK7) (bottom left histogram). PBMCs stained with anti-CD4 and GAH-APC conjugate (upper left histogram). CD3+ cell staining with ABX0030+GAH-APC conjugate (no SK7 Ab) (upper right histogram). Double staining with anti-CD-4-PE and ABX0030+GAH-APC conjugate (upper right histogram). Notice in this panel the two populations of CD3+ cells representing CD4+ and CD8+ T-cells. Doubling staining of CD3+ cells using ABX0030 and clone SK7-PE (bottom right histogram).

Binding properties of ABX0030: ABX0030 binding to target tumor cells was first confirmed. As shown in FIG. 15, ABX0030 binds to V-0025 peptide pulsed K562 cells expressing HLA-E similarly to the parent clone (ABX0011). This binding is HLA-E restricted, as HLA-E negative parent K562 cells do not exhibit binding to ABX0030 (FIG. 15). Binding to T cells in peripheral blood mononuclear cells (PBMCs) was used to confirm the anti-CD3 arm (FIG. 16). The K562 cell line was acquired from ATCC. K562 cells expressing HLA-E cells were acquired from (Dr. Thorbald van Hall, Leiden University Medical Center, Netherlands). Cells were cultured per the supplier's recommendation. For cell binding, cells were blocked with anti-human CD16 (clone KD1), anti-human CD32 (clone AT10), and anti-human CD64 (clone 10.1) (Bio-Rad) or with Human TruStain FcX (BioLegend) at room temperature for 5-10 min before surface staining with unlabeled antibody at 1 μg/mL or with AF647-labeled antibody, and with HLA-E/PE-Cy7 (clone 3D12, BioLegend) at 4° C. for 30 min in 50-100 μL. Cells were then washed with staining buffer (PBS with 2 mM EDTA) followed by secondary staining cocktail including Goat-anti-human or Goat-anti-mouse/AF647 (if using unlabeled antibody, Jackson ImmunoResearch) and zombie/aqua viability stain (BioLegend). Cells were incubated at 4° C. for 30 min in 50 μL. Cells were washed twice with staining buffer and fixed using fluorofix (BioLegend). Samples were acquired using a CytoFLEX S (Beckmen Coulter). Data was prepared using FlowJo Software version 10 (BD Biosciences).

Figure 17A:
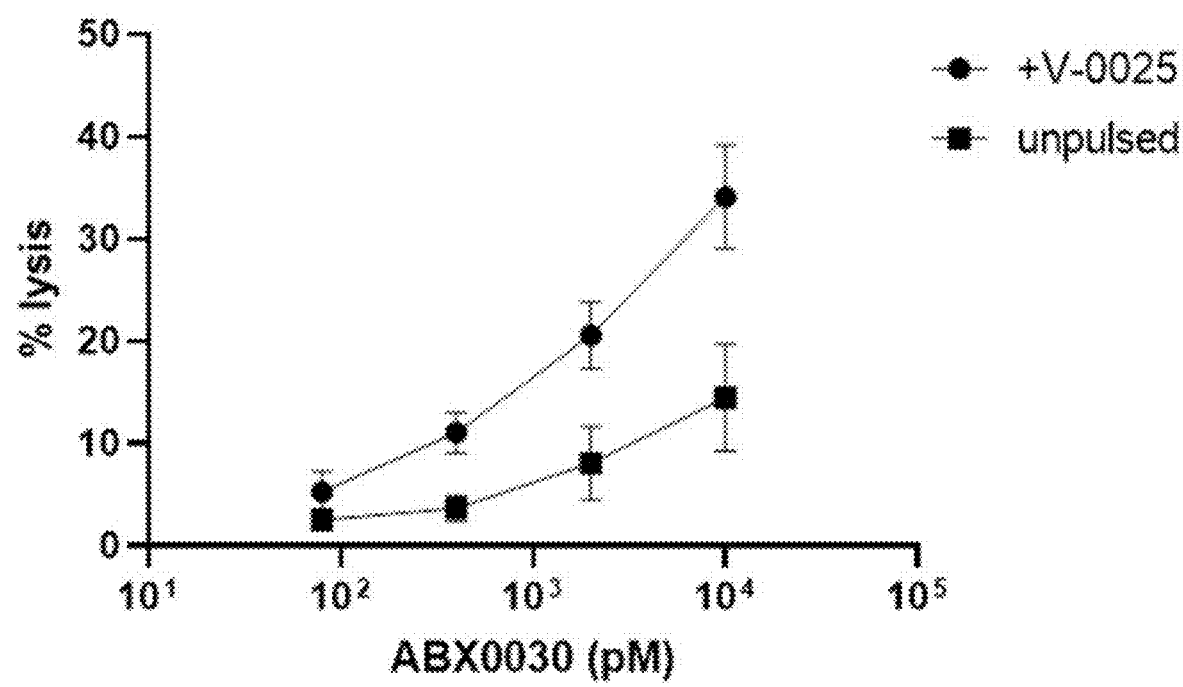
FIG. 17A-FIG. 17C exemplify ABX0030 performance to specifically activate CD8+ T-cells and to redirect T-cell lysis of target positive cells.
Figure 17B:
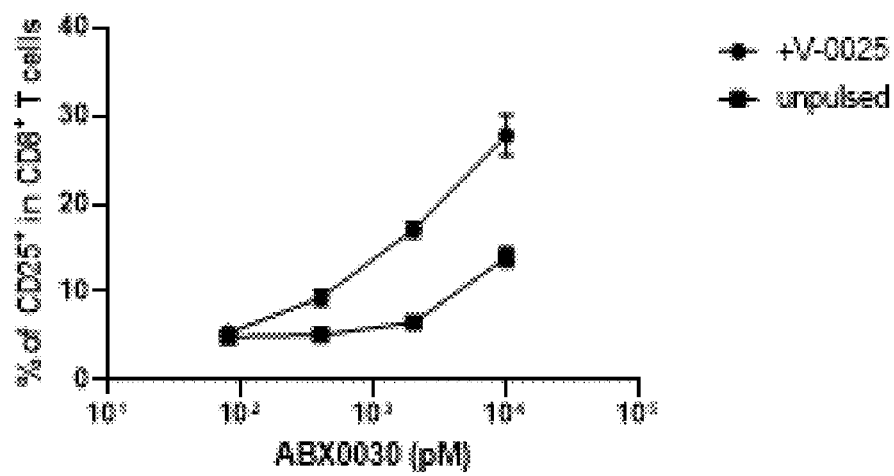
Figure 17C:
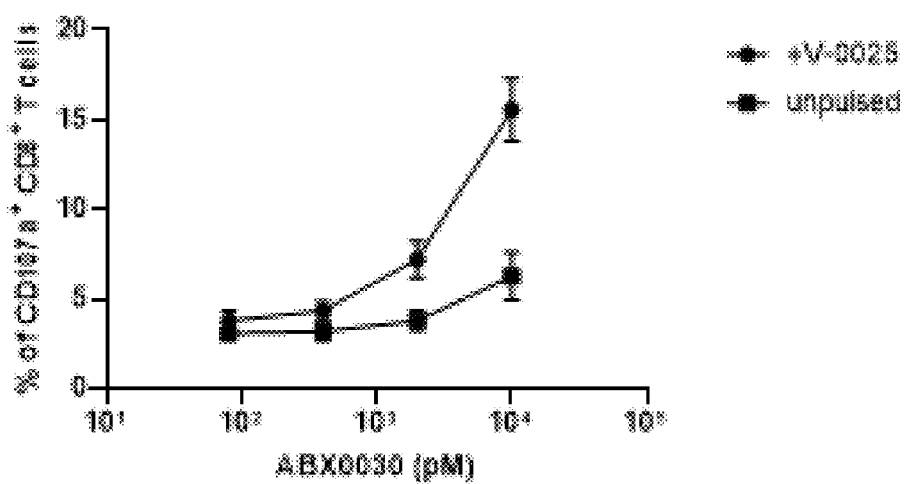

ABX0030 Enhances Target-Specific Cytotoxicity of Primary CTLs:

To assess the activity of ABX0030, primary human CTLs were co-cultured with either K562 (HLA-E positive) or K562.E pulsed with V-0025 peptide and tested with a titration of ABX0030. As shown in FIG. 17A, ABX0030 induced dose-dependent cytotoxicity in a target-specific manner; unpulsed K562.E cells were not affected. Further, ABX0030 does not induce expression of CD25 (48 hrs) (FIG. 17B) and IFNγ (48 hrs) (FIG. 17C) in CD8+ T cells cultured with target negative K562.E cells.

Figure 18A:
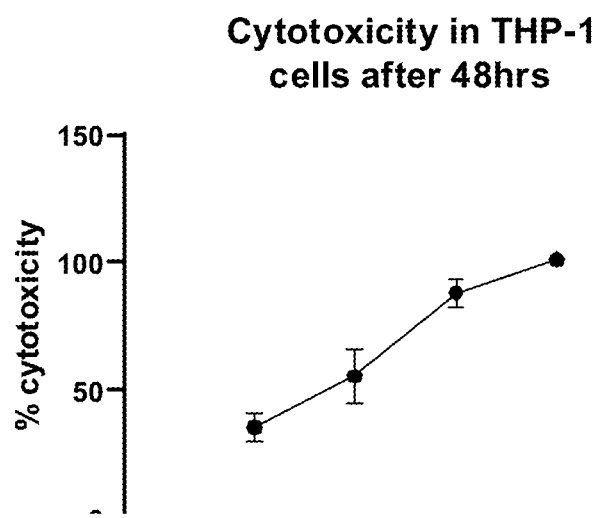
FIG. 18A-FIG. 18E exemplify potent activity of ABX0030 to redirect CD8+ T-cell lysis of THP-1 cells.
Figure 18B:
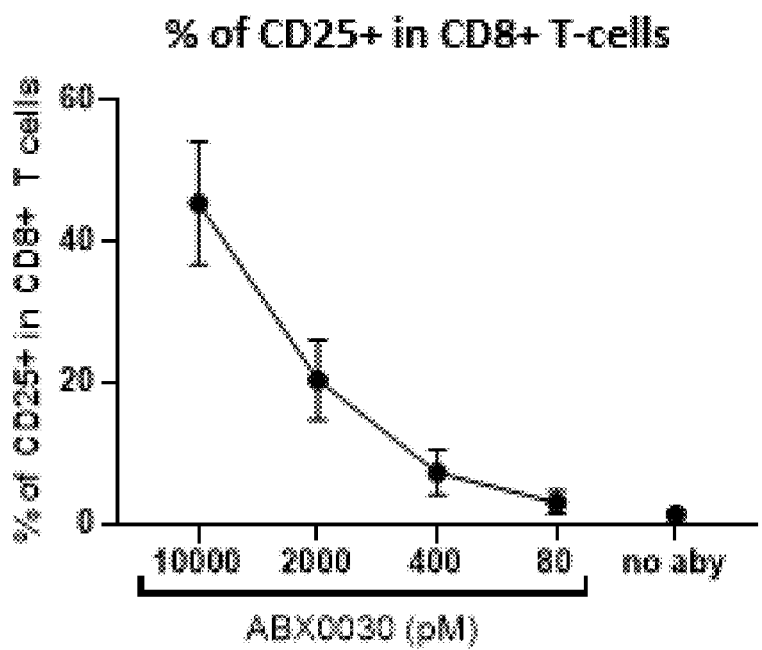
Figure 18C:
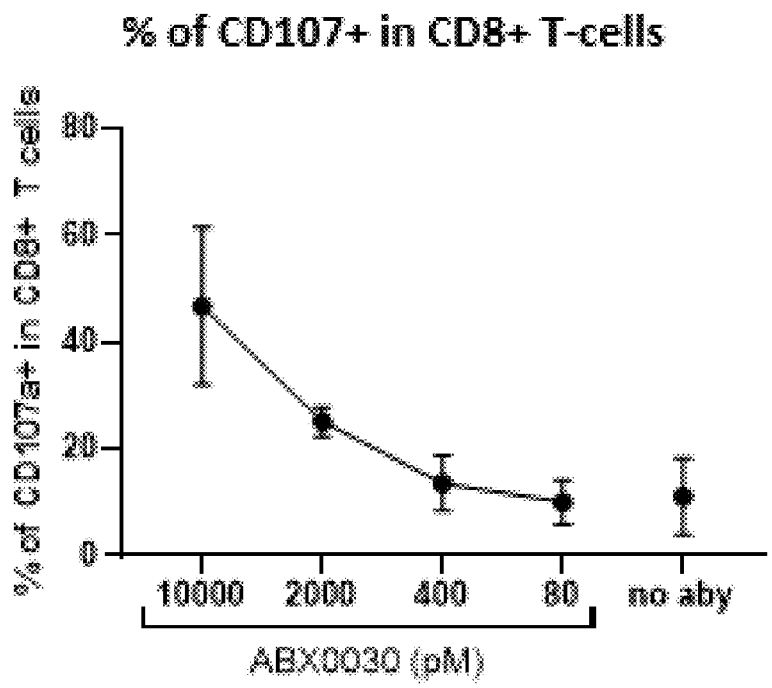
Figure 18D:
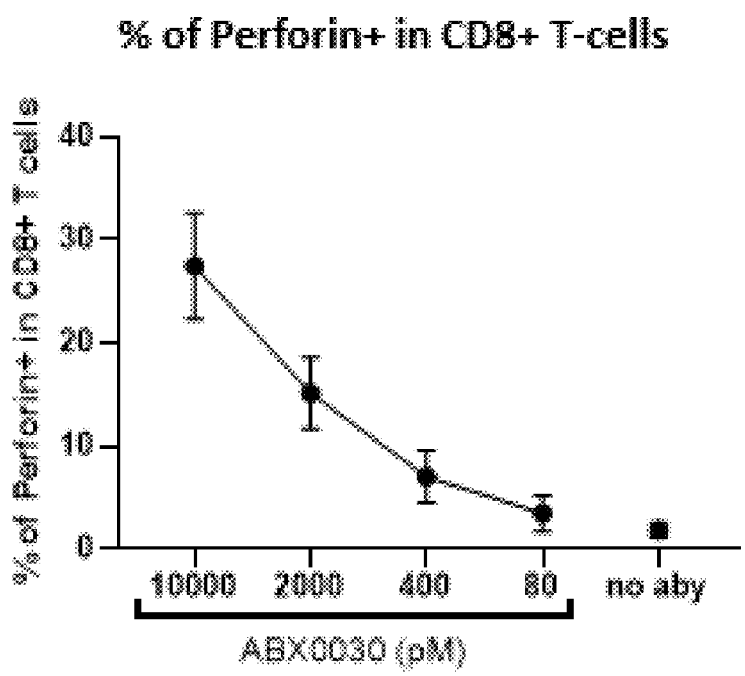
Figure 18E:
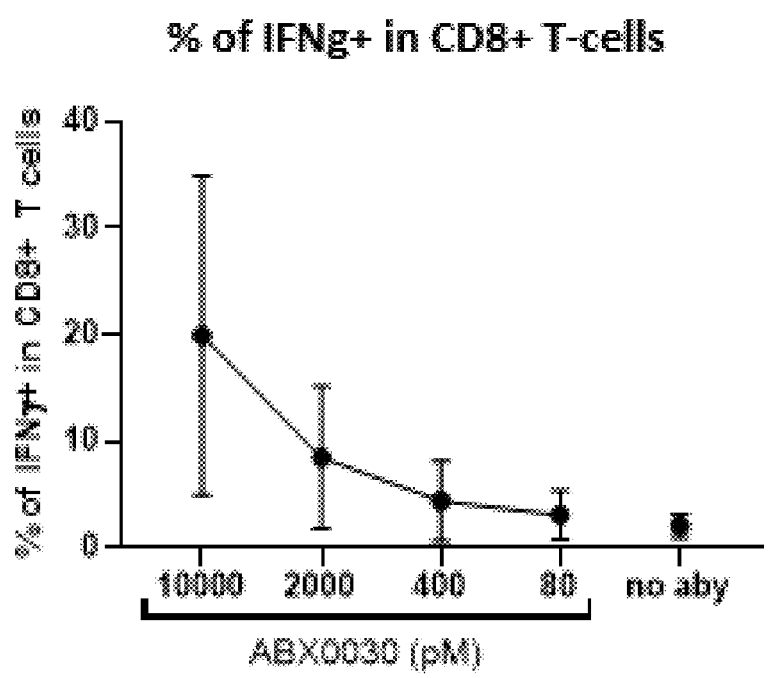

These results were confirmed using THP-1 cells (ABX0011 binding data shown in FIG. 11A). After 48 hr co-culture, ABX030 induced cytotoxicity in a dose-dependent manner (FIG. 18A). ABX0030 was also able to induce CD8+ T cell activation, as shown by the dose-dependent induction of CD25, CD107a, perforin and IFNγ (FIG. 18B-FIG. 18E). These results indicate that ABX0030 enhances lysis of tumor cells by CD8+ T cells in a target-specific manner.

To perform in vitro T-cell activation assays, blood from healthy volunteers was acquired from Carter BloodCare (Arlington, Tex.). PBMCs were isolated by density-gradient centrifugation using Ficoll-Paque PLUS (GE Healthcare) or Lymphoprep (StemCell Technologies). CD8+ T cells were purified using EasySep human CD8+ T cell enrichment kit (StemCell Technologies). The enriched human CD8+ T cells (CTLs) were rested overnight at 1×10$^6$/mL. Target cells were labeled with CFSE (ThemoFisher) and added to the rested CTLs at a ratio of 10:1 (E:T). CD3/CD28 stimulation (ImmunoCult human CD3/CD28 T cell activator, StemCell Technologies) was used as a positive control. In the last 4 hr of culture, monensin and anti-human CD107a/BV421 (BioLegend) was added to all wells. Cells were harvested after 24 to 48 hrs. Cells were stained with anti-human CD8/APC (BioLegend), anti-human CD25/PE-Cy7 (Tonbo) and Zombie/Aqua viability marker (BioLegend). For intracellular staining, cells were fixed and permeabilized using BD cytofix/cytoperm solution (BD) and were stained with anti-human Perforin/PerCP-Cy5.5 (BioLEgend) and anti-human IFNγ/PE-Dazzle 594 (BioLegend). Samples were acquired using a CytoFLEX S (Beckmen Coulter). Data was prepared using FlowJo Software version 10 (BD Biosciences).

TABLE 4

List of peptide/HLA complexes

| Peptide family | Peptide ID | Sequence | SEQ ID NO: | HLA complex | Gene Origin |
|---|---|---|---|---|---|
| Classical HLA | V-0021 | VMAPRTLIL | 21 | HLA-E | HLA-C HLA-Cw*01, -Cw*03, -Cw*04, -Cw*05, -Cw*06, -Cw*08, -Cw*12, -Cw*14, -Cw*16 and -Cw*17:02 |
|  | V-0034 | VMAPRTLVL | 22 | HLA-E | HLA-A*02, -A*23, -A*24, -A*25, -A*26, -A*34:02, -A*34:06, -A*43, -A*66 and -A*69 |
|  | V-0035 | VTAPRTLLL | 23 | HLA-E | HLA-B*13, -B*18, -B*27, -B*37, -B*40, -B*44, -B*47, -B*54, B*55 -B*56, -B*59, -B*82 and B*83 |
|  | V-0037 | IMAPRTLVL | 24 | HLA-E | HLA-A*34:01 |
|  | V-0040 | VMAPQALLL | 25 | HLA-E | HLA-Cw*17:01, Cw*17:03 and -Cw*17:05 |
|  | V-0041 | VMAPRALLL | 26 | HLA-E | HLA-Cw*06:17, -Cw*07 and -Cw*18 |
|  | V-0042 | VMAPRTLLL | 27 | HLA-E | HLA-A*01, -A*03, -A*11, -A*29, -A*30, A*31, -A*32, -A*33, -A*36, and A*74, HLA-Cw02 and Cw*15 |
|  | V-0043 | VMAPRTLTL | 28 | HLA-E | HLA-Cw*08:09 |
|  | V-0044 | VMAPRTVLL | 29 | HLA-E | HLA-B*07, -B*08, -B*14, -B*38, -B*39, -B*42, -B*48, -B*67, -B*73 and -B*81 |
|  | V-0045 | VMPPRTLLL | 30 | HLA-E | HLA-A*80 |
|  | V-0046 | VTAPRTVLL | 31 | HLA-E | HLA-B*15, -B35, -B*40, -B*41, -B*44:18, -B*45, -B*46 -B*49, -B*50, -B*51, -B*52, -B*53, -B*57, -B*58 and -B*78 |
| Non-classical HLA | V-0025 | VMAPRTLFL | 18 | HLA-E | HLA-G |
| Additional | V-0038 | QMRPVSRVL | 32 | HLA-E | Hsp60 |
|  | P-0550 | RAARLPPLL | 33 | HLA-E | PODXL2 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. A monoclonal antibody, or an antigen-binding fragment thereof, that selectively binds to a complex comprising an HLA-E and a peptide that comprises, consists essentially of, or consists of a sequence according to SEQ ID NO: 18 (VMAPRTLFL), comprising:
   (i) a light chain CDR1 having the amino acid sequence set forth as SEQ ID NO: 1, a light chain CDR2 having the amino acid sequence set forth as SEQ ID NO: 2, a light chain CDR3 having the amino acid sequence set forth as SEQ ID NO: 3; and
   (ii) a heavy chain CDR1 having the amino acid sequence set forth as SEQ ID NO: 4, a heavy chain CDR2 having the amino acid sequence set forth as SEQ ID NO: 5, and a heavy chain CDR3 having the amino acid sequence set forth as SEQ ID NO: 6.

2. The monoclonal antibody of claim 1, wherein the monoclonal antibody or antigen-binding fragment thereof does not have a binding affinity to (i) the HLA-E alone; or (ii) the peptide alone.

3. The monoclonal antibody of claim 2, wherein the peptide consists of a sequence according to SEQ ID NO: 18 (VMAPRTLFL).

4. A bispecific T cell engager, comprising the monoclonal antibody of claim 1 or an antigen binding-fragment thereof.

5. The bispecific T cell engager of claim 4, wherein the bispecific T cell engager binds to a CD3 protein associated with a T cell receptor.

6. A monoclonal antibody, or an antigen-binding fragment thereof, that selectively binds to a complex comprising an HLA-E and a peptide that comprises, consists essentially of, or consists of a sequence according to SEQ ID NO: 18 (VMAPRTLFL), comprising:
   (i) a light chain variable domain (VL) comprising the amino acid sequence set forth as SEQ ID NO: 7; and
   (ii) a heavy chain variable domain (VH) comprising the amino acid sequence set forth as SEQ ID NO: 8.

7. The monoclonal antibody of claim 6, wherein the monoclonal antibody or antigen-binding fragment thereof does not have a binding affinity to (i) the HLA-E alone; or (ii) the peptide alone.

8. The monoclonal antibody of claim 7, wherein the peptide consists of a sequence according to SEQ ID NO: 18 (VMAPRTLFL).

9. A bispecific T cell engager, comprising the monoclonal antibody of claim 6 or an antigen-binding fragment thereof.

10. The bispecific T cell engager of claim 9, wherein the bispecific T cell engager binds to a CD3 protein associated with a T cell receptor.

11. A method at treating a cancer that expresses both HLA-E and HLA-G in an individual in need thereof, comprising administering to the individual an effective amount of a monoclonal antibody of claim 1 or an antigen-binding fragment thereof, to thereby treat the cancer.

12. The method of claim 11, wherein the cancer is breast cancer, kidney cancer, lung cancer, ovarian cancer, colorectal cancer, pancreatic cancer, choriocarcinoma, non-small cell lung carcinoma (NSCLC), gastric cancer, cervical cancer, head and neck cancer, leukemia, lymphoma, myeloma, multiple myeloma (MM), acute myeloid leukemia (AML), myelodysplastic syndrome, a B-cell malignancy, or mantel cell lymphoma.

13. A method of treating a cancer that expresses both HLA-E and HLA-G in an individual in need thereof, comprising administering to the individual an effective amount of a monoclonal antibody of claim 6 or an antigen-binding fragment thereof, to thereby treat the cancer.

* * * * *

UNITED STATES PATENT AND TRADEMARK OFFICE
CERTIFICATE OF CORRECTION

Page 1 of 1

PATENT NO. : 10,981,997 B1
APPLICATION NO. : 16/926355
DATED : April 20, 2021
INVENTOR(S) : Jon Weidanz et al.

It is certified that error appears in the above-identified patent and that said Letters Patent is hereby corrected as shown below:

In the Claims

At Column 68, Line number 47, in Claim 11, please delete "A method at treating" and replace with --A method of treating--.

Signed and Sealed this
Thirtieth Day of November, 2021

Drew Hirshfeld
*Performing the Functions and Duties of the
Under Secretary of Commerce for Intellectual Property and
Director of the United States Patent and Trademark Office*